(12) United States Patent
Ohmiya et al.

(10) Patent No.: US 7,572,629 B2
(45) Date of Patent: Aug. 11, 2009

(54) MULTIPLE GENE TRANSCRIPTION ACTIVITY ASSAY SYSTEM

(75) Inventors: Yoshihiro Ohmiya, Osaka (JP); Yoshihiro Nakajima, Osaka (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 217 days.

(21) Appl. No.: 10/555,544

(22) PCT Filed: Apr. 30, 2004

(86) PCT No.: PCT/JP2004/006362

§ 371 (c)(1), (2), (4) Date: Nov. 4, 2005

(87) PCT Pub. No.: WO2004/099421

PCT Pub. Date: Nov. 18, 2004

(65) Prior Publication Data

US 2007/0105172 A1   May 10, 2007

(30) Foreign Application Priority Data

May 6, 2003 (JP) ............................. 2003-127629
Dec. 5, 2003 (JP) ............................. 2003-407564

(51) Int. Cl.
 *C12N 15/53* (2006.01)
(52) U.S. Cl. .................... 435/325; 435/320.1; 536/23.2
(58) Field of Classification Search ....................... None
See application file for complete search history.

(56) References Cited

U.S. PATENT DOCUMENTS

| 6,387,675 | B1 | 5/2002 | Wood et al. | |
| 6,495,355 | B1 * | 12/2002 | Contag et al. | 435/189 |
| 7,276,363 | B2 * | 10/2007 | Viviani et al. | 435/189 |
| 2002/0119542 | A1 | 8/2002 | Viviani et al. | |
| 2006/0265137 | A1 * | 11/2006 | Zock et al. | 702/19 |
| 2008/0090291 | A1 * | 4/2008 | Wood et al. | 435/325 |

FOREIGN PATENT DOCUMENTS

| JP | 2002-542791 | | 12/2002 |
| WO | WO 97/24460 | | 7/1997 |
| WO | WO 97/24490 | | 7/1997 |
| WO | WO 98/10059 | | 3/1998 |
| WO | WO 00/65076 | | 11/2000 |
| WO | WO 00/79264 | A1 | 12/2000 |
| WO | WO 03/016839 | A2 | 2/2003 |

OTHER PUBLICATIONS

Viviani, V.R. et al. (1999) "Cloning, sequence analysis, and expression of active phrixotrix railroad-worms luciferases: relationship between bioluminescence spectra and primary structures" Biochemistry 38:8271-8279.
Ohmiya, Y. et al. (2000) "Comparative aspects of a luciferase molecule from the Japanese luminous beetle, Rhagophthalmus ohbai" Sci. Rept. Yokosuka City Mus., 47:31-38.
Sumiya, M et al. (1999) "Cloning and expression of a luciferase from the Japanese luminous beetle Rhagophthalmus ohbai" Biolumin. Chemilumin., Proc. Int. Symp., pp. 433-436.
Grentzmann, G. et al., (1998) "A dual-luciferase reporter system for studying recoding signals" RNA 4:479-486.
Omiha K. et al. (2004) "Basic and application principle on the bioluminescence system of insect luciferases" The Japanese Biochemical Society, Tokyo, 76:5-15.
Nieuwehnuijsen, B.W. et al. (2003) "A dual luciferase multiplexed high-throughput screening platform for protein-protein interactions" J. Biomol. Screen. 8:676-684.
Viviani, V. (2001) "Thr226 is a key residue for bioluminescence spectra determination in beetle luciferases" Biochemical and Biophysical Research Communications 280:1286-1291.
Contag, P.R. et al. (1998) "Bioluminescent indicators in living mammals" Nature Medicine 4:245-247.
Thompson, E.M. et al. (1995) "Real time imaging of transcriptional activity in live mouse preimplantation embryos using a secreted luciferase" PNAS USA 92:1317-1321.
Dilella, A.G. et al. (1988) "Utility of firefly luciferase as a reporter gene for promoter activity in transgenic mice" Nucleic Acids Research 16:4159.
Supplemental Partial European Search Report from corresponding European patent application No. EP 04 73 0717, dated Oct. 10, 2007.
EBI Accession No. ABK90990, "*Phrixotrix hirtus* red light emitting luciferase, phRE, cDNA", Nov. 2002.
EBI Accession No. Q9U4U7, "*Phrixotrix hirtus* red bioluminescence eliciting luciferase", May 2000.
EBI Accession No. ABG31952, "*Phrixotrix hirtus* red light emitting luciferase, phRE, protein", Nov. 2002.
Barry, J.K. and Miller, W.A. 2002 "A-1 ribosomal frameshift element that requires base pairing across four kilobases suggests a mechanism of regulating ribosome and replicase traffic on a viral RNA" *Proc Natl Acad Sci USA* 99:11133-11138.
Kitayama, A. et al. 2003 "Creation of thermostable firefly luciferase with pH-insensitive luminescent color" *Phytochemistry and Photobiology* 77:333-338.
Sohaskey, C.D. et al. 1992 "Construction and application of plasmid- and transposon-based promoter-probe vectors for *Streptomyces spp.* that employ a *Vibrio harveyi* luciferase reporter cassette" *J Bacteriol* 174:367-376.
Viviani, V.R. et al. 2002 "The influence of Ala243 (Gly247), Arg215 and Thr226 (Asn230) on the bioluminescence spectra and pH-sensitivity of railroad worm, click beetle and firefly luciferases" *Phytochemistry and Photobiology* 76:538-544.
Wood, K.V. et al. 1989 "Introduction to beetle luciferases and their applications" *J Bioluminescence and Chemiluminescence* 4:289-301.
Wood, K.V. et al. 1989 "Complementary DNA coding click beetle luciferases can elicit bioluminescence of different colors" *Science* 244:700-702.
Zhang, J. et al. 2002 "Identification of human uroplakin II promoter and its use in the construction of CG8840, a urothelium-specific adenovirus variant that eliminates established bladder tumors in combination with docetaxel" *Cancer Res* 62:3743-3750.

* cited by examiner

*Primary Examiner*—Rebecca Prouty
(74) *Attorney, Agent, or Firm*—Wenderoth, Lind & Ponack, L.L.P.

(57) ABSTRACT

A gene construct incorporating any of at least two luciferase genes which emit lights with different colors using an identical substrate such that the gene can be stably expressed in mammalian cells.

6 Claims, 22 Drawing Sheets

Fig. 11

Many specimens are exhaustively analyzed in a primary screening.

Example 1: Screening for drugs which induce a gene expression corresponding to a disease

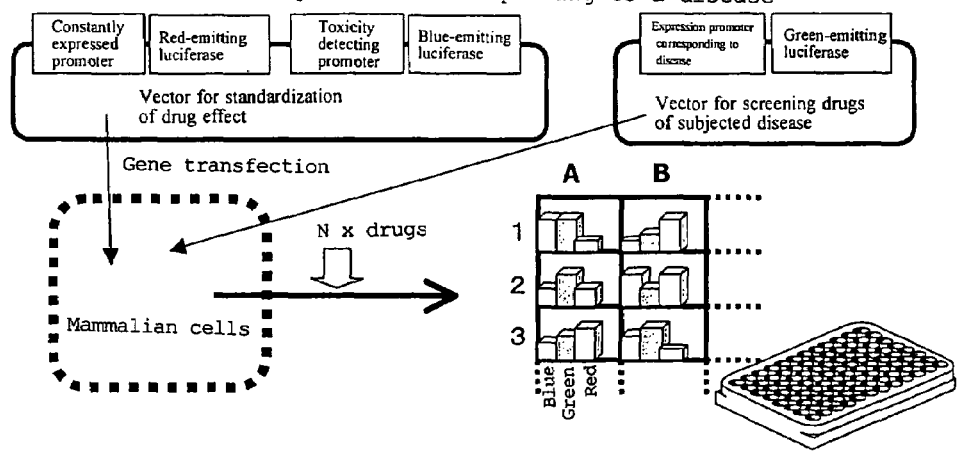

For example, in this primary screening, the red-emitting luciferase is a control, the blue-emitting luciferase detects the toxicity, and the green-emitting luciferase detects the drug effect. Therefore, it can be evaluated that the drug in an A1 column has the effect for the disease but works lethally and the drug in an A2 column has the similar effect to the A1 and is safer than the A1.

Example 2: Screening for gene expression regions which a certain drug affects

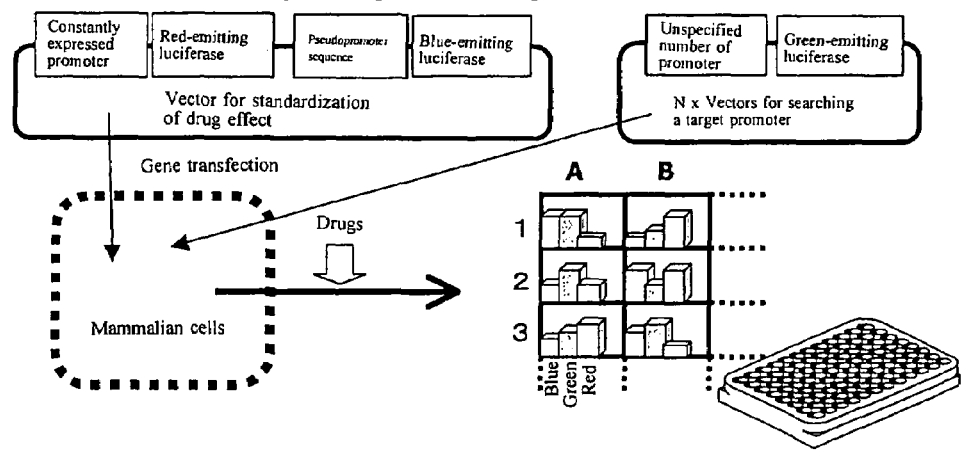

For example, in this primary screening, the red-emitting luciferase is a control, a pseudopromoter sequence is inserted in the blue-emitting luciferase, and the green-emitting luciferase reports a promoter with unknown function obtained from a promoter sequence library and evaluates a non-specific effect. A target site of the drug whose promoter target is not determined is screened. Therefore, for a certain drug, the promoter selected in an A1 column has the effect at first glance but is likely to be non-specific when determined by the blue, whereas the promoter in an A2 column has the same effect as that in the A1 column and is not non-specific so long as determined by the blue.

Fig. 13

[Sequence alignment of RedWT and REDm nucleotide sequences, positions 1–1641]

Fig. 14

[Sequence alignment figure comparing REDm and WO2003-016839 nucleotide sequences from position 1 to 1641]

Fig. 17

MULTIPLE GENE TRANSCRIPTION ACTIVITY ASSAY SYSTEM

This application is the U.S. National Phase under 35 U.S.C. §371 of International Application PCT/JP2004/006362, filed Apr. 30, 2004, which claims priority to Japanese Patent Application No. 2003-407564, filed Dec. 5, 2003, and Japanese Patent Application No. 2003-127629, filed on May 6, 2003. The International Application was published under PCT Article 21(2) in a language other than English.

TECHNICAL FIELD

The present invention relates to a gene construct for multiply detecting gene transcription activities in living cells by the use of luciferases which emit different color lights, an expression vector containing the construct, transformed mammalian cells containing the construct or the expression vector, a screening method of drugs using the mammalian cells, and a system for multiply determining the transcription activities of respective promoters.

The invention also relates to a gene and a polypeptide used for a system where the transcription activity in the living cells is detected by the use of the luciferase which emits red, orange or blue color light.

BACKGROUND ART

In the life science field, a transcription activity of an intracellular gene has been generally determined, and used for evaluation of exogenous factors given to cells, and analyses of intracellular signal transduction or expression of an individual protein group. The gene transcription activity has been directly determined by Western blotting and the like, or indirectly determined using a luciferase gene or a light-emitting enzyme gene as a reporter gene. In particular, it has been generalized to quantify the transcription activity based on an emitted light intensity using a firefly light-emitting enzyme gene. A fluorescent protein exhibits a fluorescent activity without need of a cofactor almost simultaneously with its intracellular expression. The fluorescent protein has been used as a monitor protein for examining a localization of a protein by the use of the fluorescent activity in the cell as an indicator, but it is difficult to quantify it, and it is unlikely to use it as the reporter gene for the gene expression.

It is important to analyze a quantitative and temporal dynamic change of the protein gene expression, but the transcription activity one gene has been primarily analyzed in conventional reporter techniques. However recently, a system (dual assay system, Promega) for determining two transcription activities by introducing two gene constructs into the cell, i.e., A transcription active region being inserted in a firefly light-emitting enzyme gene and B transcription active region being inserted in a *Renilla* light-emitting enzyme gene has been commercially available. However, this method is a system for determining the transcription activity by adding different luminescent substrates, respectively, two activities can not be determined simultaneously, and only two transcription activities can be determined. Furthermore, since a firefly luciferase is used, a wavelength thereof is changed due to pH and accurate determination is difficult.

Multiple signals are trafficked in a cell, and it is essential to construct a technique to quantitatively determine the multiple transcription activities. For example, in a human biological clock, a Per gene which gives a 24 hour rhythm is controlled by Clock and BMAL gene products. Thus, to precisely evaluate the biological clock, it is essential to determine multiple, at least three transcription activities. Until now, the transcription activity of an individual gene has been determined by the use of a firefly luciferase reporter gene, but a dynamic of only one gene transcription has been observed at a time, and an interaction of biological clock-related gene expressions has remained unclear.

Canceration progresses by abnormal growth of cells caused with activation of an oncogene or by the abnormal growth of the cells due to the control release caused along with inactivation of a tumor suppressing gene. Thus, to evaluate canceration factors and intracellular signal transduction of the canceration, it is desirable to determine the gene transcription activity of the oncogene, the tumor suppressing gene and a mitotic marker gene. However, in the conventional method, the dynamic of only one gene transcription has been observed at a time, the transcription activities of the three gene can not be evaluated at a time, and thus the interaction of the three genes involved in the canceration has not been sufficiently understood.

The transcription of a gene is caused by binding a substance which suppresses or promotes the gene expression to a particular sequence present on a gene sequence referred to as a promoter region upstream of a gene product. An E-box and a cAMP-binding site are representatives thereof. The gene transcription activity is determined by inserting a certain length of the promoter region into an upstream of a reporter gene. Furthermore, a particular sequence believed to be effective is then synthesized, and inserted into the upstream of the reporter gene to examine an effect of the particular sequence. To examine a transcription controlling effect of the particular sequence, it is necessary to simultaneously evaluate the transcription activity of the original promoter region and the transcription activity capable of standardizing the effect in combination. However, in the conventional method, the transcription dynamic of only one gene has been observed, and the particular sequence for the control of the transcription activity can not be sufficiently evaluated.

A luciferase is useful as a means to directly observe the gene transcription activity in the cells, and has been used as a detection monitor protein of the gene expression. There are a wide variety of luciferases, but no reporter gene for determining the transcription activity based on their diversity is available. If using luciferase genes which emit different color lights as the reporter genes and different transcriptional active regions are inserted into mammalian cells, then multiple transcription activities can be determined. A red-emitting luciferase derived from a rail road worm has the longest wavelength of luminescence, is easily discriminated compared to the luciferases derived from a firefly and a click beetle, and is highly permeable into the cell due to the red-emitting color. However, the expression of the red and green-emitting luciferases from the rail road worm has been successfully done only in *Escherichia coli* (US 2002/0119542-A1), and there is no successful example as the system in the mammalian cells including human cells.

There is also an example in which the expression of a luciferase gene from the rail road worm in the mammalian cells was enabled by modifying a structure of the gene (WO 2003/016839).

As the luciferase, a luciferase derived from *Rhagophthalmus ohba* has been also known.

The expression of a green-emitting luciferase derived from *Rhagophthalmus ohba* has been successfully done in only *Escherichia coli* (Ohmiya, Y. Sumiya, M. Viviani, V R. and Ohba N.; Comparative aspects of a luciferase molecule from the Japanese luminous beetle *Rhagophthalmus ohba*. Sci. Rept. Yokosuka City Mus. .47, 31-38, 2000). Based on this sequence, an orange-emitting luciferase derived from *Rhagophthalmus ohba* was created and the expression thereof was also successfully done in *Escherichia coli* (Viviani, V R., Uchida, A., Suenaga, N., Ryufuku M. and Ohmiya Y.: Thr-226 is a key-residue for bioluminescence spectra determination in beetle luciferases. Biochem. Biophys. Res. Commun., 280, 1286-1291, 2001). Additionally, as the luciferase, blue-emitting luciferases derived from a dinoflagellate and *Renilla* have been also known.

It is an object of the present invention to construct and optimize a reporter gene capable of determining or quantifying multiple transcription activities in a cell simultaneously or at the same phase, further develop a multiple gene transcription activity determining system using the reporter gene group, and utilize the same for cell functional analyses in life science, further the treatment/examination of pathology and new drug development.

It is also another object to make a gene construct by which a red- or a green-emitting luciferase from a rail road worm is stably transcribed and stably translated in mammalian cells or in animals.

It is also another object to make a gene construct by which an orange or a green-emitting luciferase from a *Rhagophthalmus ohba* is stably transcribed and stably translated in mammalian cells or in animals.

This enables to stably determine and visualize a change of the gene transcription activity in the mammalian cells or in the animals.

BRIEF DESCRIPTION OF THE DRAWINGS

FIG. 11 shows an example in which many specimens are exhaustively analyzed by a primary screening.

FIG. 13 shows homology of a DNA sequence of a rail road worm red-emitting luciferase gene mutant (SEQ ID NO:7) of the present invention with that of a rail road worm wild-type red-emitting luciferase gene (SEQ ID NO:3).

FIG. 14 shows homology of a DNA sequence of a rail road worm red-emitting luciferase gene mutant (SEQ ID NO:7) having a maximum luminescence wavelength of 630 nm with that of a rail road worm red-emitting luciferase gene mutant of WO 2003/016839 (SEQ ID NO:6) having a maximum luminescence wavelength of 622 nm.

FIG. 17 shows homology of a DNA sequence of a *Rhagophthalmus ohba* green-emitting luciferase mutant (SEQ ID NO:10) with that of a wild-type (SEQ ID NO:8).

DISCLOSURE OF THE INVENTION

Figure 1:
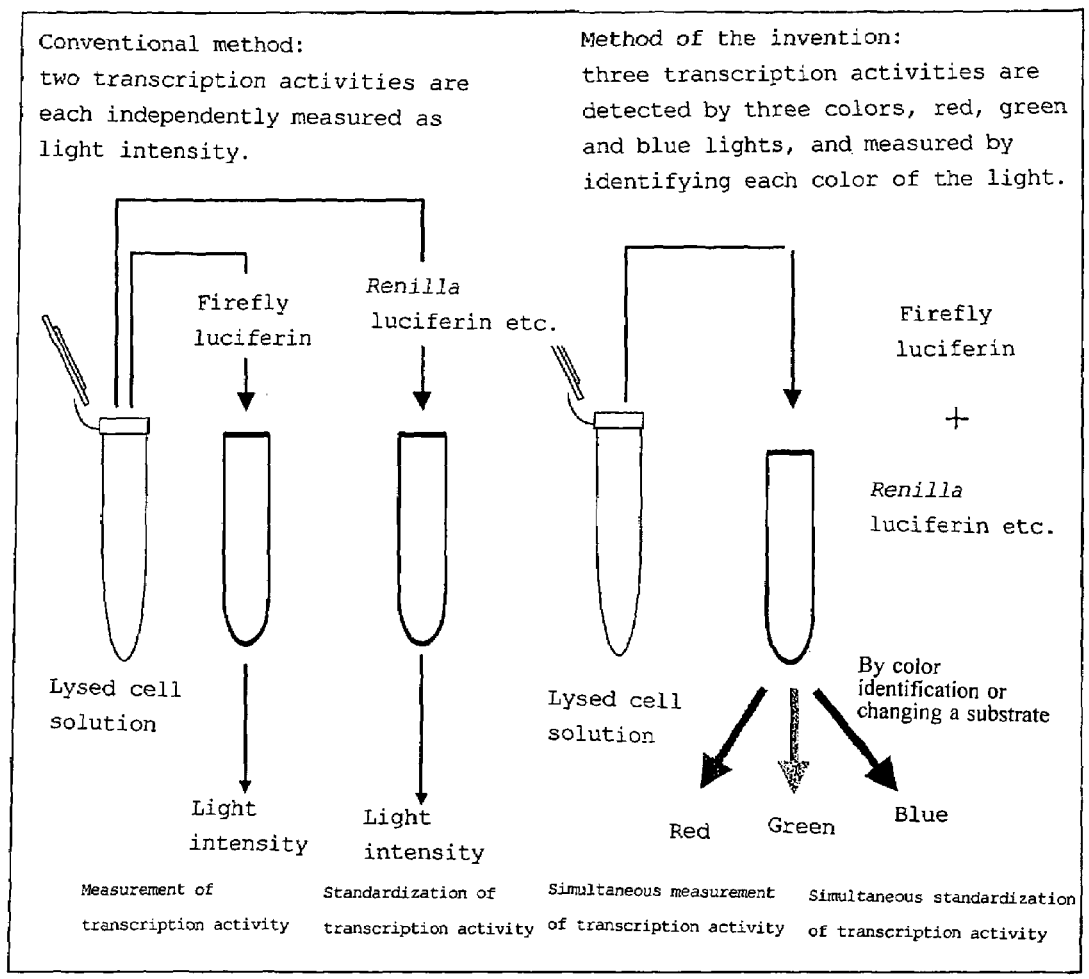
FIG. 1 shows an outline of determination for multiple gene transcription activities and differences from a conventional method.

As a result of an intensive study for solving the above subjects, the present inventor has made a reporter gene construct capable of distinctively quantifying lights derived from 2 or more, preferably 3 or more and more preferably 4 or more luciferases (red-, orange-, green- and blue-emitting) based on the luciferases which emits different color lights (including red, orange, green and blue) or various luminescent substrates. According to the present invention, 2 or more, preferably 3 or more and more preferably 4 or more gene activities can be determined preferably simultaneously or at the same phase because an emitted light intensity derived from each luciferase corresponds to a transcription activity of each promoter, i.e., the activity of the gene to which each promoter is originally linked. It is also possible to precisely determined because a luminescence wavelength is not changed due to a determining condition (pH, etc). For example, in one preferable embodiment of the present invention, a system for determining the transcription activities of multiple genes simply and highly quantitatively was made by making reporter gene constructs of a red-emitting luciferase and a green-emitting luciferase from a railroad worm and a green-emitting luciferase and an orange-emitting luciferase from *Rhagophthalmus ohba*, and simultaneously using luciferase reporter genes of *Renilla*, a marine ostracod, a luminescent dinoflagellate, a click beetle, aequorin and the like.

Furthermore, the present inventor has found that the transcription can be easily performed in mammalian cells for a luciferase which is scarcely expressed or is not expressed at all in the mammalian cells by (1) altering a cDNA sequence such that no additional transcription factor is bound and (2) changing a codon usage (bias of codon use frequencies) for insects to the codon usage for mammals in the cDNA sequence and further reducing restriction enzyme sites in the cDNA sequence because the many restriction enzyme sites limit an application of the cDNA.

The present invention provides the following polypeptide, gene, gene construct, mammalian cell, a method for screening drugs and a system for multiply determining the transcription activities of the promoters using the mammalian cells.

1. DNA encoding at least one luciferase selected from the group consisting a red-emitting luciferase and a green-emitting luciferase derived from a rail road worm and a green-emitting luciferase and an orange-emitting luciferase derived from *Rhagophthalmus ohba* stably expressed in mammalian cells, characterized in that (1) the DNA has no binding sequence for an additional transcription factor in the mammalian cells and has a codon usage for the mammal.

2. The DNA according to the above 1, characterized in that the mammal is human and the DNA has at least one nucleotide sequence selected from the group consisting of SEQ ID NOS:7, 10, 11 and 16.

3. A method for enabling the expression of DNA encoding a luciferase derived from a rail road worm or *Rhagophthalmus ohba* in mammalian cells, characterized by having 1) a step of altering a cDNA sequence such that no additional transcription factor is bound;

2) a step of changing a codon usage for insects to that for mammals in the cDNA sequence; and optionally 3) a step of altering the cDNA sequence with many restriction enzyme sites due to limited application at the use.

4. The method according to the above 3, characterized in that an amino acid sequence of the luciferase is not altered.

5. A polypeptide which is a luciferase with a maximum luminescence wavelength of 630 nm, represented by any of the followings:

(1) a polypeptide having an amino acid sequence of SEQ ID NO:4; and (2) a polypeptide having one or more amino acid substitutions, additions or deletions in the sequence of SEQ ID NO:4.

6. The polypeptide according to the above 5, expressed in mammalian cells.

7. A gene construct incorporating one or two or more genes of luciferases which emit light whose wavelength does not substantially depend on a determining condition and maximum luminescence wavelength is 535 to 635 nm, to be stably expressible in mammalian cells.

8. The gene construct according to the above 7 incorporating 3 or more luciferase genes stably expressibly in mammalian cells by incorporating one or two or more genes of luciferases with a maximum luminescence wavelength of 460 to 520 nm together with one or two or more genes of luciferases which emit light whose wavelength does not substantially depend on a determining condition and maximum luminescence wavelength is 535 to 635 nm.

9. The gene construct according to the above 7 wherein the above luciferase gene is a gene encoding at least one luciferase selected from the group consisting of a red-emitting luciferase and a green-emitting luciferase derived from a rail road worm and a green-emitting luciferase and an orange-emitting luciferase derived from *Rhagophthalmus ohba* stably expressed in mammalian cells.

10. The gene construct according to the above 7 comprising an element for promoting efficiency of translation and/or an element for stabilizing mRNA.

11. A gene construct capable of distinctively determining each light emitted from two or more luciferases, by incorporating one or two or more genes of the luciferases which emit light whose wavelength does not substantially depend on a determining condition and if necessary a gene of the luciferase which emits light whose wavelength is different and does not substantially depend on the determining condition under the control of different promoters.

12. An expression vector containing the gene construct according to any of the above 7 to 11.

13. Mammalian cells transformed with the gene construct according to any of the above 7 to 11 or the expression vector according to the above 12.

14. Mammalian cells stably expressibly incorporating two or more genes of luciferases which emit mutually distinct light whose luminescence wavelength does not substantially depend on a determining condition under the control of different promoters in the mammalian cells.

15. The mammalian cells according to the above 13 or 14 wherein two or more of the above luciferases have maximum luminescence wavelength of 535 to 635 nm and can emit with one substrate.

16. The mammalian cells according to the above 15 comprising a red-emitting luciferase gene from a rail road worm and further comprising at least two or more selected from the group consisting of a green-emitting luciferase gene from the rail road worm, a green-emitting luciferase gene from *Rhagophthalmus ohba*, an orange-emitting luciferase from *Rhagophthalmus ohba*, and a blue-emitting luciferase gene under the control of different promoters.

17. The mammalian cells according to the above 14 stably expressibly incorporating genes of three or more luciferases which emit mutually distinct light whose luminescence wavelength does not substantially depend on a determining condition under the control of different promoters in the mammalian cells.

18. The mammalian cells according to the above 14 having three or more luciferase genes under the control of different promoters wherein a first luciferase gene is under the control of a constantly expressed promoter, a second luciferase gene is under the control of a toxicity assessing promoter, and remaining one or more luciferase genes are under the control of a promoter subjected to assessment.

19. The mammalian cells according to the above 14 having three or more luciferase genes under the control of different promoters wherein a first luciferase gene is under the control of a constantly expressed promoter, a second luciferase gene is under the control of a pseudopromoter, and remaining one or more luciferase genes are under the control of a promoter subjected to assessment.

20. The mammalian cells according to the above 14 having 4 or more luciferase genes under the control of different promoters, wherein a first luciferase gene is under the control of a constantly expressed promoter, a second luciferase gene is under the control of a toxicity assessing promoter, a third luciferase gene is under the control of a promoter of a protein which accepts an external factor, and remaining one or more luciferase genes are under the control of a promoter subjected to assessment.

21. The mammalian cells according to the above 14 having 4 or more luciferase genes under the control of different promoters, wherein a first luciferase gene is under the control of a constantly expressed promoter, a second luciferase gene is under the control of a pseudopromoter, a third luciferase gene is under the control of a promoter of a protein which accepts an exogenous factor, and remaining one or more luciferase genes are under the control of a promoter subjected to assessment.

22. The mammalian cells according to the above 14 having two luciferase genes under the control of different promoters, wherein a first luciferase gene is under the control of a constantly expressed promoter, and a second luciferase gene is under the control of a toxicity assessing promoter.

23. The mammalian cells according to the above 14 having two luciferase genes under the control of different promoters, wherein a first luciferase gene is under the control of a constantly expressed promoter, and a second luciferase gene is under the control of a pseudopromoter.

24. A method for screening drugs including a step of culturing the mammalian cells according to any of the above 18 to 21 in the presence of a drug candidate compound in a medium of the mammalian cells, a step of quantifying an amount of the above luciferase in the presence or absence of the candidate compound, and a step of assessing an effect of the candidate compound on a promoter subjected to assessment, which is linked to at least one luciferase.

25. A system for multiply determining transcription activity of each promoter linked to each luciferase before and after a change of a culture environment by changing the culture environment of the mammalian cells according to any of the above 13 to 23, and assessing expressed amounts of two or more luciferases which emit mutually distinct light whose luminescence wavelength does not depend on a determining condition.

26. The system according to the above 23 for simultaneously determining expressed amounts of two or more luciferases.

27. The system according to the above 23 capable of determining expressed amounts of three or more luciferases.

The present invention will be illustrated in detail below.

Two or more luciferases in the present invention are required to emit light whose luminescence wavelength does not substantially depend on a determining condition (e.g., pH) because it is important to determine an emitted light intensity from two or more luciferases and calculate a relative ratio thereof.

As used herein, "the luminescence wavelength does not substantially depend on the determining condition" is that even if a pH, temperature, concentration or the like is changed, a variation of the maximum luminescence wavelength is 3 nm or less, preferably 2 nm or less, more preferably 1 nm or less, and in particular, preferably 0.5 nm or less. If a changed amount of the maximum luminescence wavelength is within this range, when the expressed amounts of multiple luciferases are quantified by separating with a filter(s), it is preferable because a mutual ratio of the luciferases is scarcely changed.

As used herein, "two or more luciferases which emit mutually distinct light" means that it is possible to determine the ratio of emitted light intensities of the mutual lights using a filter (color filter, band pass filter, etc.). For example, for a red-emitting luciferase, a green-emitting luciferase from the rail road worm and an orange-emitting luciferase, a green-emitting luciferase from *Rhagophthalmus ohba*, it is possible to determine the ratio of emitted light intensities of mutual lights by using the filter to remove the green. To be capable of determining the ratio of emitted light intensities of the mutual lights, it is preferable to mutually separate the maximum luminescence wavelengths by usually 20 nm or more, preferably 30 nm or more, more preferably 40 nm or more and in particular, preferably 50 nm or more.

Preferable luciferases used in the invention include green-to-red-emitting (including mutants thereof, maximum luminescence wavelength: 535 to 635 nm, e.g., 540 to 630 nm) luciferases from the rail road worm, orange- to green-emitting (including mutants thereof, maximum luminescence wavelength: 530 to 600 nm) luciferases from the click beetle, and orange- to green-emitting (including mutants thereof, maximum luminescence wavelength: 550 to 590 nm) luciferases from *Rhagophthalmus ohba*, and the like. For example, in the case of the luciferases of the rail road worm, the red-emitting luciferase with a maximum luminescence wavelength of 622 nm and the green-emitting luciferase with a maximum luminescence wavelength of 545 nm have been known (US 2002/0119542), but the present inventor has identified that there exist many luciferases which emit lights with 540 to 635 nm in addition to these two. These luciferases can be all used. For example, the present inventor has confirmed that the red-emitting luciferase with a maximum luminescence wavelength of 622 nm (expressed in insects or *Escherichia coli*) from the rail road worm shifts the maximum luminescence wavelength to 630 nm when expressed in mammalian cells. This red-emitting luciferase with a maximum luminescence wavelength of 630 nm from the rail road worm was discovered for the first time by the present inventor.

When multiple luciferases are used, to distinctively determine each emitted light using the filter, it is desirable to mutually separate the maximum luminescence wavelength by 20 nm or more, preferably 30 nm or more, more preferably 40 nm or more and in particular, preferably 50 nm. By separating the maximum luminescence wavelength to this extent, the emitted light intensities of respective lights can be quantified simultaneously by using the filter between the maximum luminescence wavelengths, measuring a transmittance of each light before and after the filter, and converting.

Figure 20:
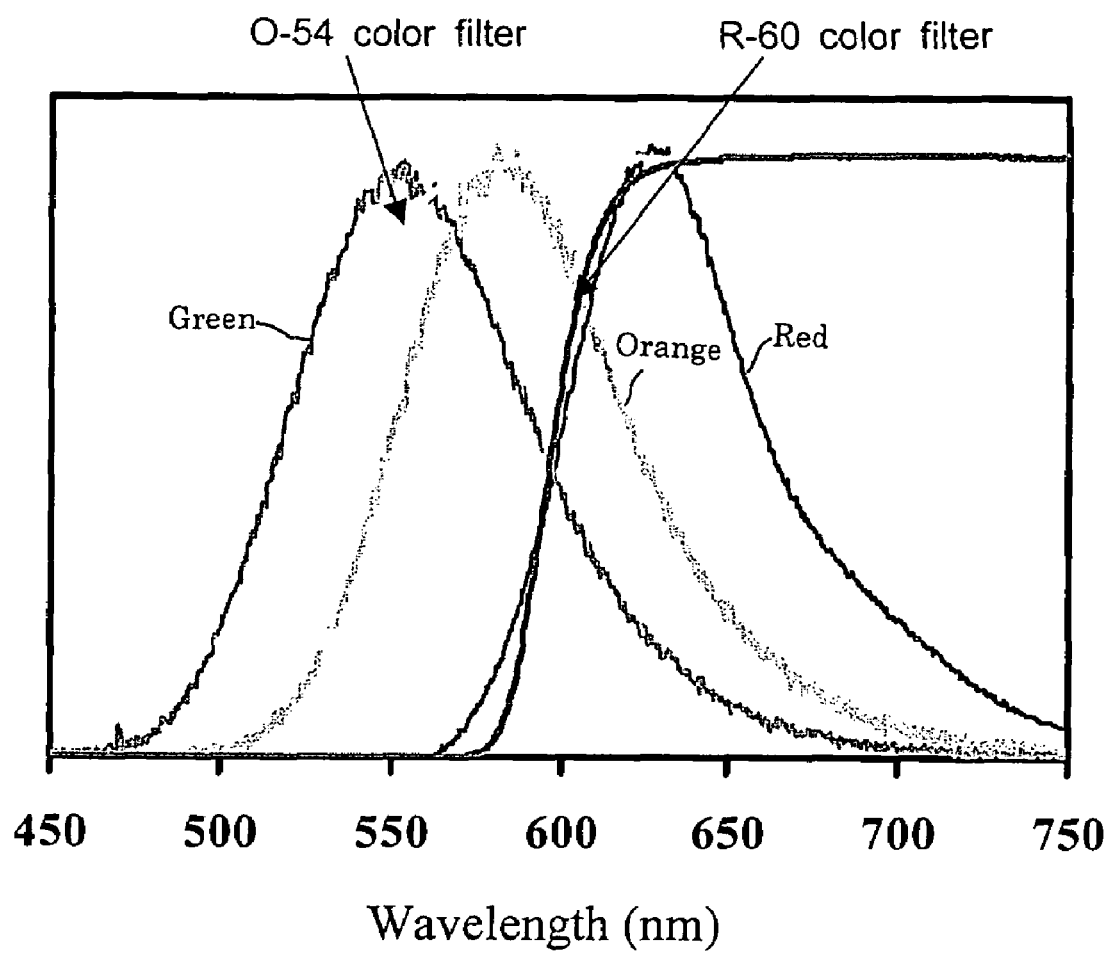
FIG. 20 shows luminescence spectra of a mixture of *Rhagophthalmus ohba* green and orange-emitting, rail road worm red-emitting luciferases and a transmittance curve of a set split filter.

For example, the maximum luminescence wavelengths of the luciferases in FIG. 20 are a red-emitting (630 nm), an orange (580 nm) and a green (550 nm), and these can be sufficiently separated.

In particular, when using the luciferases from the rail road worm and *Rhagophthalmus ohba* having the multiple luciferases whose maximum luminescence wavelengths are separated to some extent, it is possible to simultaneously quantify the emitted light intensities from the co-expressed multiple luciferases by the use of one luminescent substrate (e.g., a firefly luciferin can be used for the luciferases from the rail road worm, *Rhagophthalmus ohba* and the click beetle), and the ratio of the expressed amounts of promoters can be determined precisely. As the luciferase which emits the light whose luminescence wavelength does not depend on the determining condition (e.g., pH), it is possible to use *Renilla* luciferase, various luciferases of dinoflagellate (including a total sequence or luminescent domains such as Domains 1, 2 and 3; JP-2002-335961; Li L., Hong R., Hasting J W., Proc. Natl. Acad. Sci. USA (1997) 94, 8954), and marine ostracod luciferase by further combining. When the luciferases from the rail road worm, *Rhagophthalmus ohba* and the click beetle are used, the firefly luciferin can be used, and thus it is possible to reduce the background. The combination of the dinoflagellate luciferase with the luciferin is preferable because the background is low.

In one preferable embodiment of the present invention, it is possible to quantify the expressed amounts of at least three promoters with one luciferin by the use of the luciferases from the rail road worm, *Rhagophthalmus ohba* (e.g., the red-emitting luciferase from the rail road worm, the orange-emitting luciferase and the green-emitting luciferase from *Rhagophthalmus ohba*) (VR. Viviani, A. Uchida, N. Suenaga, M. Ryufuku & Y. Ohmiya: Thr-226 is a key-residue for bioluminescence spectra determination in beetle luciferases (2001) Biochem. Biophys. Res. Communi. 280, 1286-1291). It is also possible to quantify four or more by combining the blue-emitting luciferase (each luciferase of *Renilla*, the dinoflagellate or the marine ostracod). By successfully setting the filters, it is possible to analyze multiple expressions between 540 to 635 nm (green to red-emitting), and preferably between 540 to 630 nm. Further, one more can be added by a blue-emitting luciferase whose substrate is different. Therefore, as the simultaneous determination of the luciferases, it is possible to simultaneously quantify three or more when the same luciferin is used, and four or more when the different luciferins are used.

Conventionally, as the luciferases expressible in the mammalian cells, the *Renilla* luciferase and the firefly luciferase have been known. However, the color of the light emitted from the firefly luciferase varies from green to yellow depending on the pH of a cell lysed solution. Therefore, when the expressed amounts of two or more luciferases are compared, there has been a drawback that an accuracy is lacked. The blue luminescence derived from the *Renilla* luciferase is desirable in that its luminescence wavelength does not substantially depend on the determining condition, but in the determination system in which the firefly luciferase is combined, it is necessary to separately perform both the quantification using the firefly luciferin and the quantification using the *Renilla* luciferin. Thus, there has been a drawback that simplicity and accuracy are lacked.

The present inventor focused on the luciferase from the rail road worm as the luciferase other than *Renilla* luciferase and the firefly luciferase, and attempted to express this protein in the mammalian cells, but could not express the luciferase from the rail road worm in the mammalian cells using usual expression systems. This is believed to be a reason why no luciferase other than *Renilla* luciferase and the firefly luciferase has been expressed in the mammalian cells, particularly human cells.

According to findings until now of the present inventor, in one preferable embodiment of the invention, what really matters upon practical application of the rail road worm luciferase, the *Rhagophthalmus ohba* luciferase and the marine ostracod luciferase is that a rail road worm luciferase gene, the *Rhagophthalmus ohba* luciferase gene and the marine ostracod luciferase gene are stably transcribed and stably translated. In a technique used in Example of the present invention, it has been proven that the practical application becomes possible by stabilizing transcribed mRNA and increasing a number of translation frequency. That is, in this case, it has become possible for the first time that the luciferase gene from the rail road worm is expressed in the mammalian cells by inserting a globulin intron to prolong a lifespan of mRNA and inserting a Kozak sequence to increase the translation frequency.

Further techniques in the preferable other embodiments of the invention include, for example, changing the cDNA sequence from the codon usage (bias of codon use frequency) for insects to that for mammals for increasing copy numbers of mRNA, changing the cDNA sequence such that no additional transcription factor is bound, and changing the cDNA sequence with many restriction enzyme sites because the application of such a sequence is limited. Such techniques were useful for the expression of the luciferase from the rail road worm and the *Rhagophthalmus ohba* luciferase in the mammalian cells. In particular, the change to the codon usage (bias of codon use frequency) for the mammals and the change of cDNA sequence such that no additional transcription factor is bound are more useful.

The change of the cDNA sequence can be performed by considering the following order 1) to 4) sequentially:

1) the amino acid sequence of the luciferase is not changed as possible (preferably not changed at all);

2) subsequently, the cDNA sequence is changed such that no additional transcription factor is bound;

3) further, the codon usage for the insects is changed to that for the mammals in the cDNA sequence; and 4) if necessary, the cDNA sequence is changed to reduce the restriction enzyme sites.

In the above, the expression of the luciferase from the rail road worm and the *Rhagophthalmus ohba* luciferase was described, but the luciferases from other organisms such as a click beetle are believed to similarly express.

As used herein, the "luciferase" encompasses a light-emitting enzyme group such as luciferase which catalyzes a luciferin photochemical reaction, and also includes those such as aequorin. A protein having a luminescence action obtained by changing a luciferin structure, whose catalysis (action where the luciferin is oxidized to convert a light-emitting substance) is weak can be included in the luciferase of the present invention as long as its luminescence wavelength does not substantially depend on the determining condition (e.g., pH).

As the luciferases, it is desirable to combine two or more luciferases which emit the light with the same luminescent substrate. As preferable luciferases whose luminescence wavelength is not substantially changed by the determining condition and which emit the light with the same substrate, a red-emitting luciferase from the rail road worm and a green-emitting luciferase from the rail road worm or other luciferases from the rail road worm having the luminescence wavelength in the range of about 540 to 635 nm, preferably about 540 to 630 nm, further a green-emitting luciferase from *Rhagophthalmus ohba* and an orange-emitting luciferase from *Rhagophthalmus ohba* are preferably exemplified. In addition to them, the luciferases (about 530 to 600 nm) from the click beetle are also exemplified. In particular, the red-/green-emitting luciferases from the rail road worm and the orange-/green-emitting luciferases from *Rhagophthalmus ohba* are convenient for multiply quantify the transcription activities of promoters because emitted light intensities are almost the same when amounts of the luciferases are the same.

In the present invention, the mammals include human, cattle, horse, sheep, monkey, swine, mouse, rat, hamster, guinea pig, rabbit and dog, and is preferably the human.

It is preferable that at least two luciferase genes emit different color lights with the same substrate and their intracellular lifespan be similar. In this respect, the red-/green-emitting luciferases from the rail road worm and the orange-/green-emitting luciferases from *Rhagophthalmus ohba* are preferable. In particular, the red-emitting luciferases from the rail road worm and the orange-/green-emitting luciferases from *Rhagophthalmus ohba* are preferable.

Figure 5:
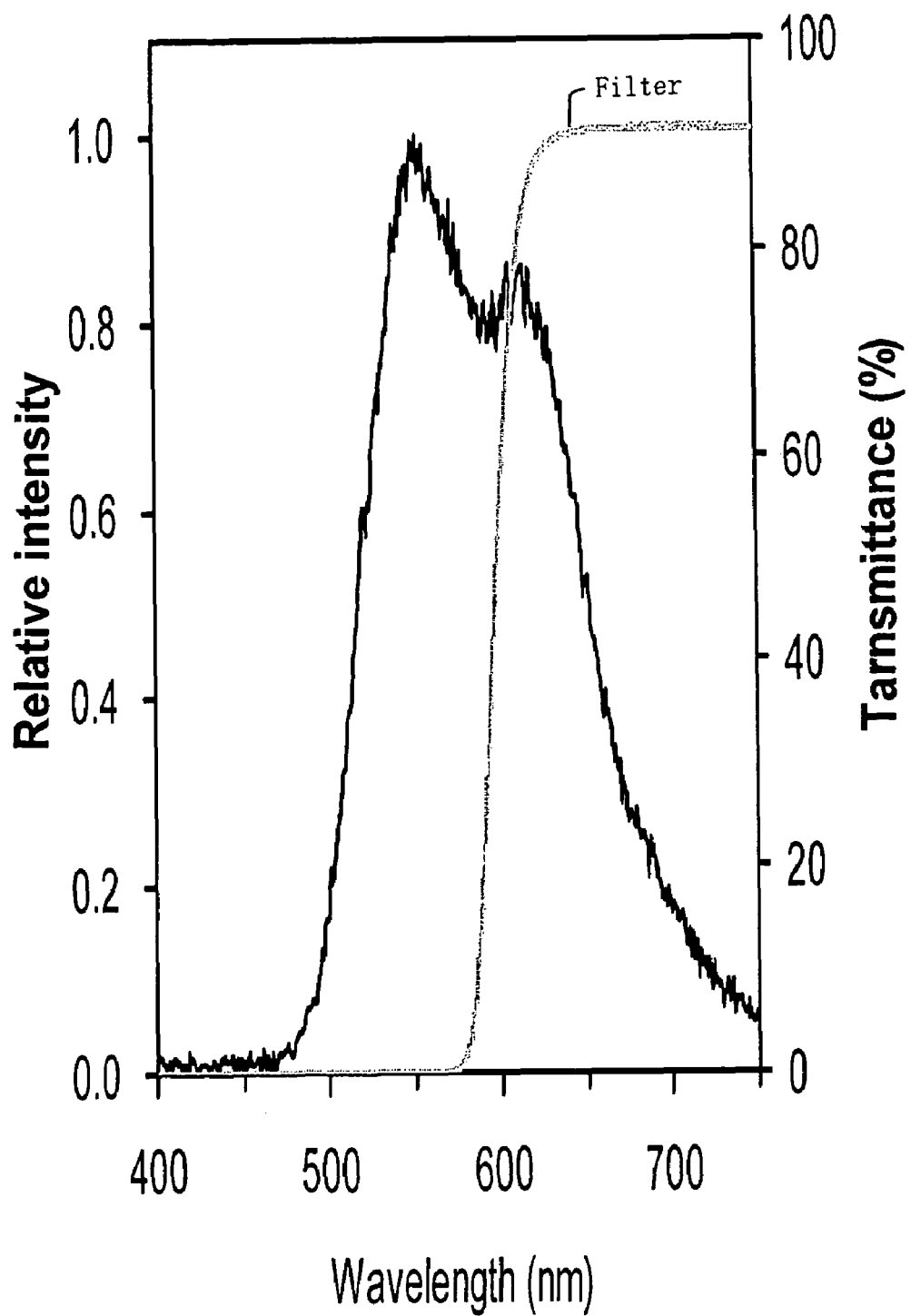
FIG. 5 shows a simultaneous luminescence spectrum of a red-emitting luciferase and a green-emitting luciferase produced in cultured mammalian cells and property of a filter used for color identification (transmittance of lights).
Figure 10:
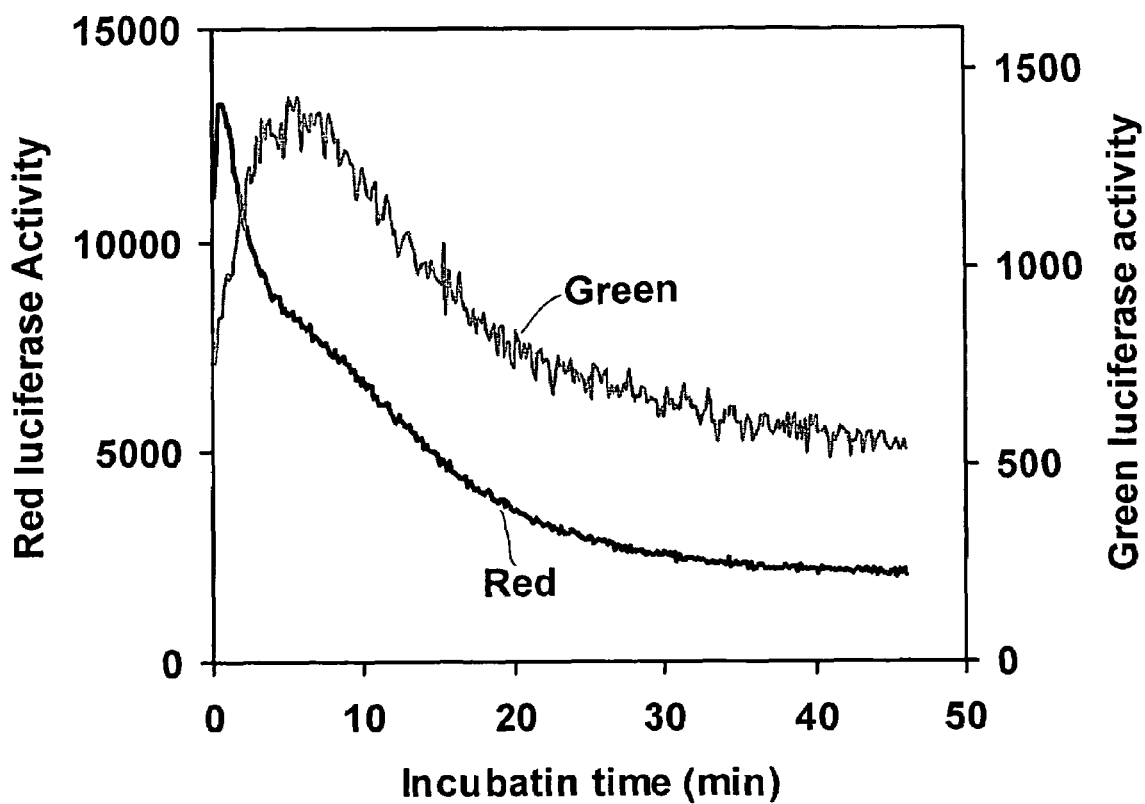
FIG. 10. shows a result indicating that transcription activities shown by a red-emitting luciferase and a green-emitting luciferase were obtained from continuous monitoring of the two transcription activities.
Figure 19:
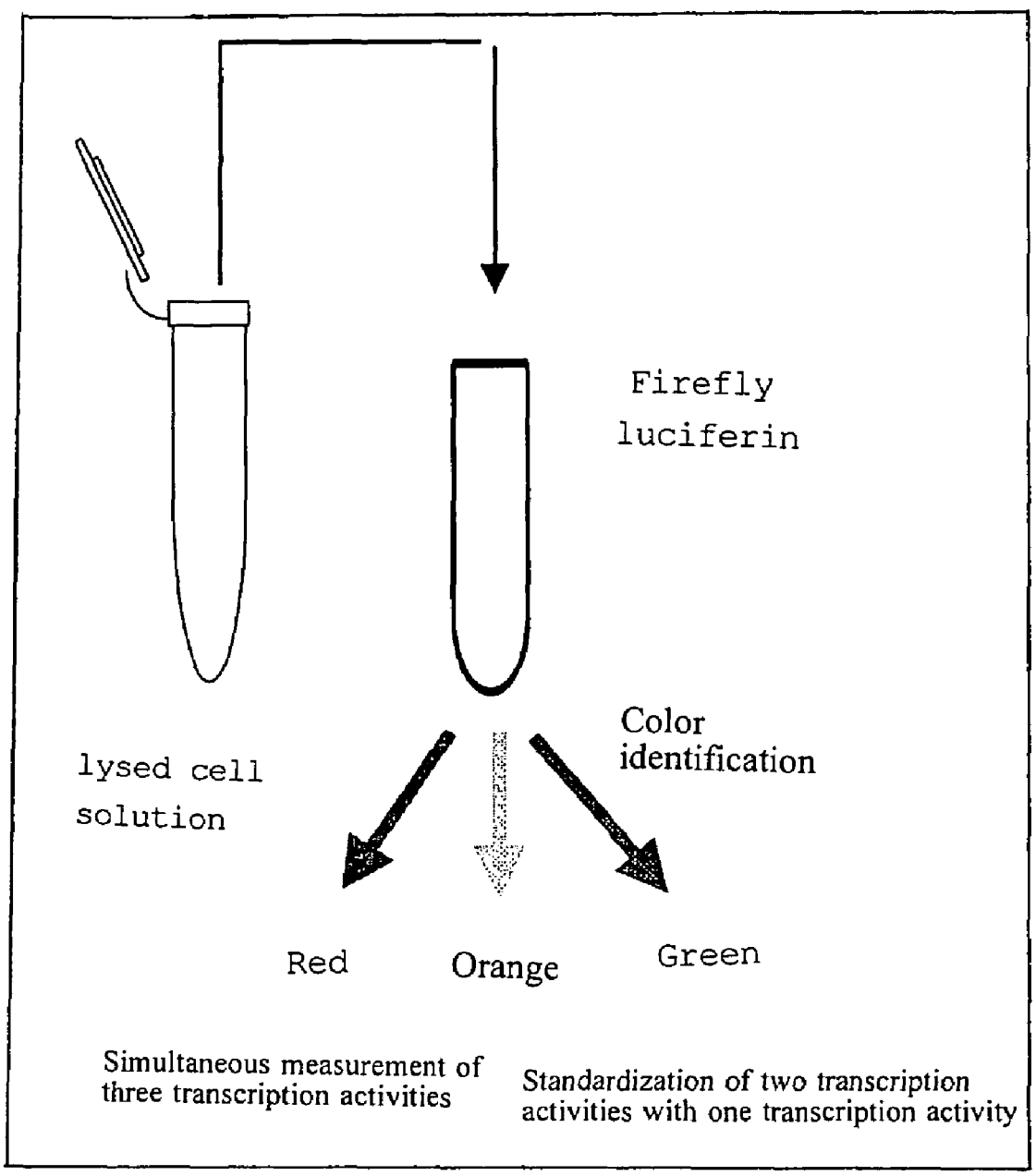
FIG. 19 shows an outline of a method for detecting the expression of three genes by one substrate, a firefly luciferin. In the method of the present embodiment, determination is performed by transmitting three transcription activities by red, orange and green color lights and identifying the respective colors.

Furthermore, for the quantification of each emitted light color by a simple apparatus, it is preferable to be capable of separate by a filter (s) different emitted light colors of at least one, preferably at least two luciferases whose luminescence wavelengths used in the invention are not changed by the determining condition (e.g., pH) and the other luciferase for standardizing the above luciferases. For example, as shown in FIG. 5, the red-/green-emitting luciferases from the rail road worm is preferable because they can be easily separated using the filter. Furthermore, the combination of the red-/green-emitting luciferases from the rail road worm with the luciferase (maximum luminescence wavelength: 474 to 480 nm) derived from *Renilla* or the-dinoflagellate is particularly preferable because the emitted lights can be easily separated using two filters as shown in FIG. 10. The lights emitted from the red-emitting luciferases from the rail road worm and the orange-/green-emitting luciferases from *Rhagophthalmus ohba* can be mutually separated using two filters (FIG. 19).

Figure 2:
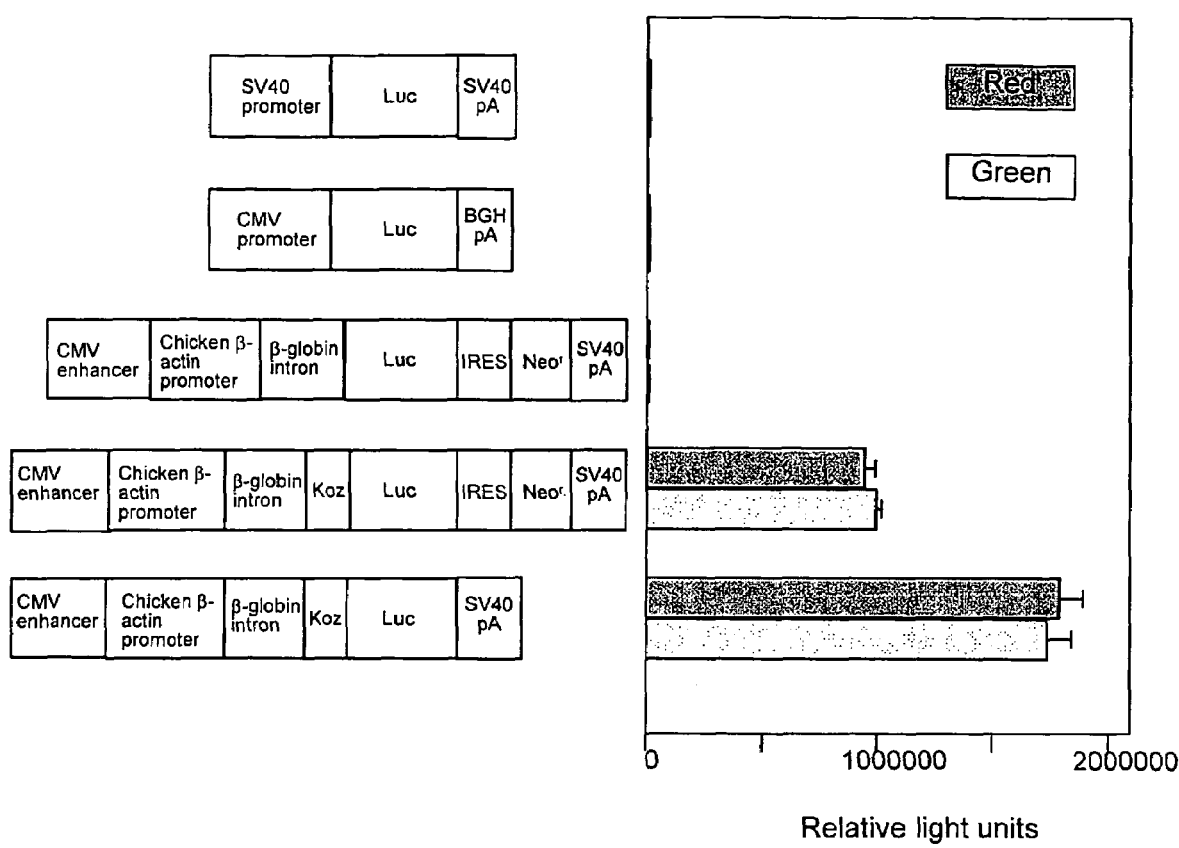
FIG. 2 shows a structure of an expression vector for mammalian cells and luminescence activity in Hela cells.

The luciferases from the rail road worm as in the above have been known to express in *Escherichia coli*, but no expression thereof in the mammalian cells, particularly human cells has been known. In fact, even when the expression of the luciferases (red-emitting, green-emitting) was attempted in the human cells, the expression could not be induced using an SV40 or CMV promoter alone which is a representative expression promoter in the mammalian cells as shown in FIG. 2 and Example 1. In the case of *Rhagophthalmus ohba* luciferases, an expression level is too low to apply practically in the sequence known publicity, but the mutants of the present invention have the expression levels of 44 times (green) and 57 times (orange) compared to wild-type luciferase, and have significant practicability. In the preferable embodiment of the invention, an expressed amount of the wild-type is insufficient because the expressed amount of the luciferase with particular color is evaluated in luminescence spectra using the filter(s).

Gene sequences of the luciferases (red-emitting, green-emitting) from the rail road worm are disclosed in US 2002/0119542-A1. A red-emitting luciferase gene (having an error) in US 2002/0119542-A1 is shown in SEQ ID NO:5. Correct nucleotide sequences of the luciferases from the rail road worm are shown in SEQ ID NO:1 (green-emitting luciferase gene) and SEQ ID NO:3 (red-emitting luciferase gene), and correct amino acid sequences are shown in SEQ ID NO:2 (green-emitting luciferase gene) and SEQ ID NO:4 (red-emitting luciferase gene).

As the luciferase gene of the present invention, intact wild-type or mutant luciferase genes can be used, and it is possible to use DNA capable of hybridizing with the luciferase gene under a stringent condition and DNA encoding a polypeptide having one or more amino acid substitutions, additions, deletions or insertions in the luciferase and having a luciferase activity as the luciferase gene.

In one preferable embodiment, the present inventor has found by examining various expression systems that it is important for stable expression of the luciferase in the mammalian cells to introduce an element for promoting efficiency of the translation and/or an element for stabilization of mRNA into a gene construct. As the element for promoting the efficiency of the translation, Kozak sequence (Ko) and the like are exemplified. As the element for the stabilization of mRNA, β-globin intron II and the like are exemplified. To stably express the luciferase in the mammalian cells, in particular, a partial structure of (globin intron II)-(Kozak sequence)-(red-/green-emitting luciferase) is preferable. It has been also confirmed that it is preferable for stable expression of the luciferase in the mammalian cells to change the codon usage (bias of codon use frequency) for the insects to that for the mammals and change the cDNA sequence such that no additional transcription factor is bound.

In one preferable embodiment, the gene construct of the invention can contain a luciferase gene, a promoter, the element for promoting the efficiency of the translation and/or the element for the stabilization of mRNA upstream of the gene, and further can contain an enhancer, IRES, SV40 pA, a drug resistant gene (Neo$^r$, etc.) and the like.

Examples of the preferable gene construct of the present invention will be shown below.

(1) (CMV enhancer)-(chicken β-actin promoter)-(β-globin intron II)-(Kozak sequence)-(red/green-emitting luciferase)-(SV40 poly A sequence)

(2) (CMV enhancer)-(chicken β-actin promoter)-(β-globin intron II)-(Kozak sequence)-(red-/green-emitting luciferase)-(IRES)-(Neo gene)-(SV40 poly A sequence)

The gene construct of the invention may be directly introduced into the mammalian cells, but it is preferable to incorporate in a vector (e.g., including a plasmid and a viral vector) to introduce into the mammalian cells. When multiple luciferases are incorporated expressibly in a gene construct, one gene construct or expression vector may be introduced into the mammalian cells, and when one luciferase is incorporated in one gene construct, multiple gene constructs or expression vectors may be simultaneously or sequentially introduced into the mammalian cells according to the standard method.

As combination of genes desirably determined simultaneously by the system of the present invention, clock genes (Per gene, Clock gene, BMAL gene, etc.)
cancer genes (oncogene, tumor suppressing gene, mitosis marker gene, etc.)
genes involved in diseases (pathology corresponding gene, life and death sensitive apoptosis gene, hormone gene, etc.)
constantly expressed genes (actin gene, GAPDH (glyceraldehyde phosphate dehydrogenase) gene, monkey-derived SV40 virus gene, etc) and the like are exemplified.

The following application can be performed in the present invention.

(1) Primary screening: It is important to simultaneously obtain 3 or more information on the assumption that many specimens are exhaustively analyzed. Obviously multiple combinations are thought. Considering drug discovery, it is necessary to evaluate not only positive points but also negative toxic points for effects of the drug. Furthermore, changes of two genes at a transcriptional level reflect a status of a cell itself, and thus, it is preferable to use a constantly expressed promoter which indicates the status of the cell as a control. Therefore, in the drug discovery screening, the following combinations are exemplified.

In tables 1 and 2, red-/blue-/green-emitting luciferases are only exemplified, and it goes without saying that the other luciferases including the orange-emitting luciferase or the combinations thereof can be used. In particular, the combination of red-/orange-/green-emitting luciferases from the rail road worm and *Rhagophthalmus ohba* is particularly preferable because they can be simultaneously determined with the firefly luciferin.

The luciferases with various color can be optionally selected.

TABLE 1

Drug discovery screening

| | |
|---|---|
| Subject promoter + green-emitting luciferase | Evaluation of drug effect |
| Toxicity evaluation promoter (apoptosis-related) + blue-emitting luciferase | Evaluation of drug safety |
| Constantly expressed promoter + red-emitting luciferase | Evaluation of cell condition |

Green-/red-emitting: standardization of drug effect
Blue-/red-emitting: standardization of safety In this case, the toxicity evaluation and the constant expression are controls of the promoter subjected to the drug evaluation, and thus it is also useful to construct in one vector. A cell itself in which this vector has been incorporated is a basic cell for screening.

TABLE 2

Search of target promoter sequence

| | |
|---|---|
| Unspecified promoter (sequence group whose effect is unknown on promoter library) + Green-emitting luciferase | Evaluation of drug effect |
| Pseudopromoter sequence (random sequence or nonsense sequence) + Blue-emitting luciferase | Evaluation of drug safety |
| Constantly expressed promoter + red-emitting luciferase | Evaluation of cell condition |

Green-/red-emitting: standardization of promoter effect
Blue-/red-emitting: standardization of pseudo information In this case, the pseudopromoter and the constantly expressed promoter are controls of the promoter subjected to the screening, and thus it is also useful (not essential) to construct in one vector. A cell itself in which this vector has been incorporated is a basic cell for screening.

The combination of -/orange-/green-emitting can accomplish the screenings represented in Tables 1 and 2 using one substrate. That is, the blue-emitting luciferase is substituted with the orange-emitting luciferase. In this case, the determination can be performed using one substrate, and the determining method is simpler. For determining the blue-emitting luciferase, it is necessary to lyse cells, but the firefly luciferin permeates into living cells with a concentration gradient and emits the light, and thus it is possible to determine three emitted lights in the living cells. Therefore, this method is characterized in that the screening can be performed without lysing the cells.

Meanwhile, the combination of red-/orange-/green-/blue-emitting has an advantage that an external factor such as environmental disruptors can be simultaneously evaluated, and can determine a change of transcription activities of multiple genes in the cell affected by the external factor. For example, monitoring of the expression of receptor which directly captures the external factor is included.

TABLE 3

| | |
|---|---|
| Unspecified promoter (sequence group whose effect is unknown on promoter library) + Green-emitting luciferase | Evaluation of external factor effect |
| Pseudopromoter sequence (random sequence or nonsense sequence) + Blue-emitting luciferase | Evaluation of external factor safety |
| Promoter sequence of accepting protein of external factor + Orange-emitting luciferase | Evaluation of accepting process of external factor |
| Constantly expressed promoter + red-emitting luciferase | Evaluation of cell condition |

Green-/red-emitting: standardization of promoter effect,
Blue-/red-emitting: standardization of pseudo information,
Orange-/red-emitting: standardization of external factor acceptance,
Green-/orange-emitting: evaluation of acceptance and activation In this case, a protein which accepts the external factor, a protein affected thereby, and further the safety of the cell itself can be evaluated, and the information which the external factor gives to the cell can be precisely evaluated by standardizing them with the control of the protein of the constantly expressed promoter. Thus, it is also useful (not essential) to construct in one vector. A cell itself in which this vector has been incorporated is a basic cell for screening.

Examples of the primary screening are shown in FIG. 11.

(2) Secondary screening: It is important to obtain 3 or more information on the assumption that the focused drug effects and promoter signals are evaluated. In the drug discovery, multiple effects of the drug are often assumed. It is also important to know a gene which indicates the change of cell condition, transient effects of the drug (e.g., toxicity, shock response, etc.), and actual effects. For example, as shown in Tables 3 and 4, evaluation systems of clock-related drug effects can be exemplified.

TABLE 3

Evaluation system of clock-related drug effects

| | |
|---|---|
| Drug detection promoter (e.g., toxicity, shock response, etc.) + Green-emitting luciferase | Evaluation of transient effect of drug |
| Diurnally varying promoter (sequence of BMAL or Per gene) + Blue-emitting luciferase | Evaluation of biological clock |
| Drug corresponding promoter + Red-emitting luciferase | Evaluation of intracellular effects of drug |

Blue-/green-/red-emitting: temporal axis evaluation of drug

TABLE 4

Evaluation system of clock-related drug effects

| | |
|---|---|
| Drug detection promoter (e.g., toxicity, shock response, etc.) + Green-emitting luciferase | Evaluation of transient effect of drug |
| Diurnally varying promoter (sequence of BMAL or Per gene) + Orange-emitting luciferase | Evaluation of biological clock |
| Drug corresponding promoter + Red-emitting luciferase | Evaluation of intracellular effects of drug | orange-/green-/red-emitting: temporal axis evaluation of drug

In particular, as in the above, it is possible to determine three emitted lights in the living cells using one substrate. Therefore, the method is characterized in that the drug effect can be evaluated according to the temporal axis without lysing the cells.

A series of operations is performed for the same cells, and thus the drug effect on the combination (history) of the multiple operations can be evaluated.

Figure 12:
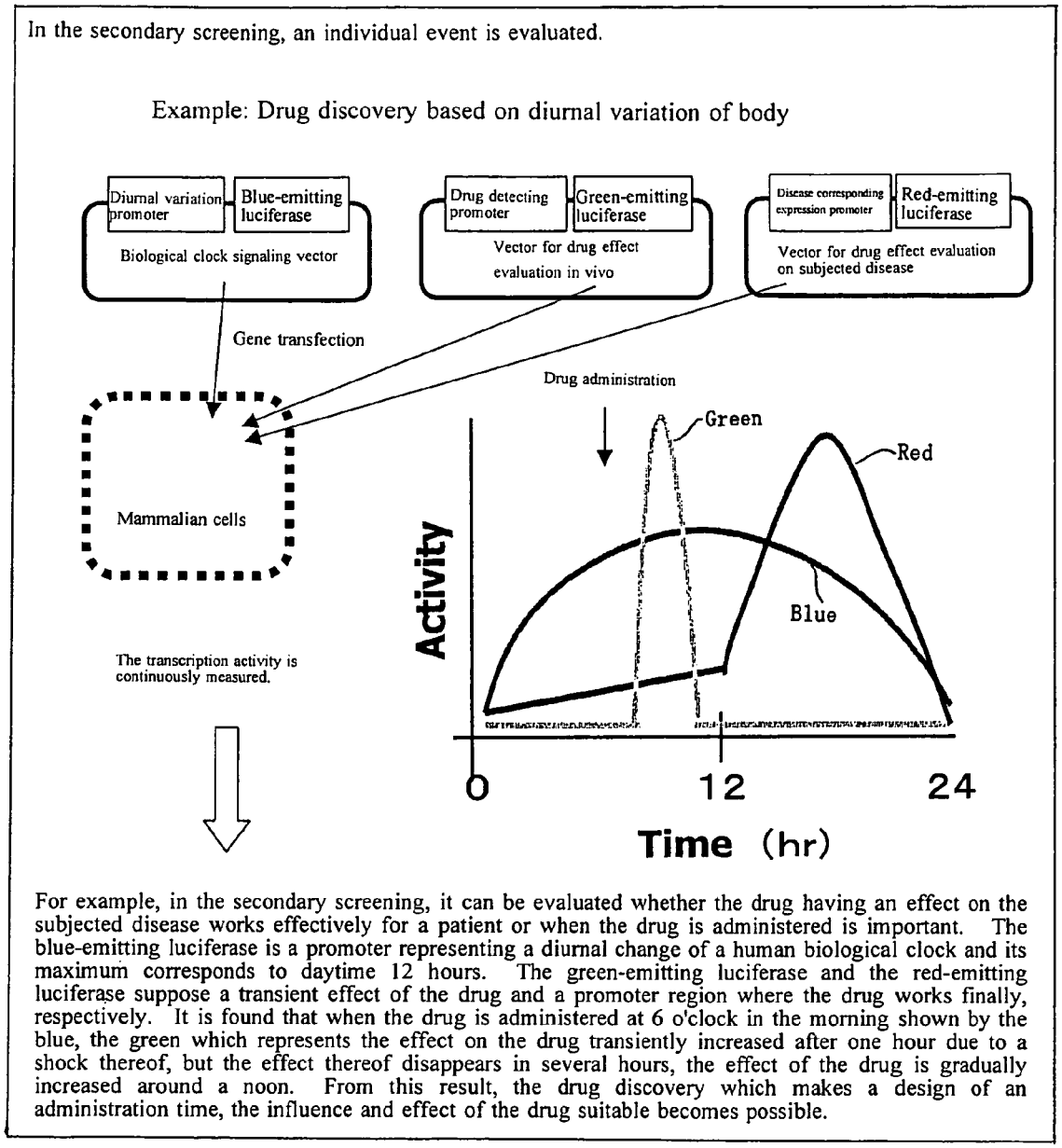
FIG. 12 shows an example in which an individual event is evaluated by a secondary screening.

An example of the secondary screening is shown in FIG. 12.

As in the above, by preferably simultaneously evaluating expressed amounts of 2 or more, particularly 3 or more or 4 or more promoters, when actions for one promoter are evaluated, it is possible to standardize an activity, toxicity and the like or standardize pseudo information.

Furthermore, when a phenomenon where the expressions of multiple genes are intricately related in the mammal is elucidated, the system of the present invention is extremely useful.

In the particularly preferable embodiment of the invention, the method/system for simultaneously quantifying three or four gene transcription activities using the red-emitting luciferase gene, the green-emitting luciferase gene from the rail road worm, the green-emitting luciferase gene, the orange-emitting luciferase gene from *Rhagophthalmus ohba*, and the blue-emitting luciferase gene is provided. By the use of this system, it is possible to simultaneously determine multiple transcription activities in the cells. It is possible to utilize them for the treatment/examination of pathology and the new drug development.

At that time, color identification is performed, and the multiple transcription activities in the cells can be simultaneously determined by determining the luminescence activity using the filters specified for the red-, green-, orange- and blue-emitting. Much information can be simultaneously elicited for the change in the cells, whose information has been conventionally difficult to obtain from change information of one transcription activity, and can be utilized for the treatment of various diseases and the new drug development.

In the present invention, the mammalian cells having two luciferase genes under the control of distinct promoters (1) wherein a first luciferase gene is under the control of the constantly expressed promoter and a second luciferase gene is under the control of the toxicity assessing promoter or (2) wherein the first luciferase gene is under the control of the constantly expressed promoter and the second luciferase gene is under the pseudopromoter according to claim 14 are useful as intermediate cells for producing the mammalian cells for drug screening by further introducing the gene construct in which one or more luciferase genes are incorporated under the control of promoters subjected to the evaluation in these mammalian cells.

BEST MODE FOR CARRYING OUT THE INVENTION

The present invention will be illustrated in more detail with reference to the following Examples, but it goes without saying that the invention is not limited to the Examples.

EXAMPLE 1

A green-emitting luciferase gene and a red-emitting luciferase gene (SEQ ID NO:1, 3) from a rail road worm are expressed in *Escherichia coli*, but the expression thereof can not be induced in mammalian cells using an SV40 or CMV promoter alone which is a representative expression promoter in mammals. Thus, a construct in which Kozak sequence and β-globin intron II which stabilize the gene expression were inserted, and further chicken β-actin promoter and CMV enhancer were selected was ligated to the red- or green-emitting luciferase gene to make a gene structure, and an enzyme activity was determined. (FIG. 2). This was compared with a gene structure in which the luciferase gene had been inserted downstream of the SV40 promoter, CMV promoter or CAG promoter. Cultured fibroblast cells, NIH3T3 cells were transfected with each gene using Lipofectamine, and a luminescence activity after 24 hours in the cells was determined (FIG. 2). For determining the luminescence activity, a luminescent substrate mixed solution (supplied from Toyo B-Net Co., Ltd.) and AB-2000 were used as a substrate and as a luminescence determining apparatus supplied from ATTO Corporation, respectively. To 50 μL of a cell extract solution, 50 μL of PicaGene was added. As a result, the highest activity was obtained in the cells into which the (CMV enhancer)-(chicken β-action promoter)-(β-globin intron II)-(Kozak sequence)-(red-/green-emitting luciferase)-(SV40 poly A sequence) gene had been introduced. The secondarily highest activity was obtained in the cells into which the construct in which (IRES)-(Neo gene)-(SV40 poly A sequence) had been inserted in place of (SV40 poly A sequence) had been introduced. However, the SV40 promoter or the CMV promoter alone elicited almost no activity. But, the activity elicited by the (CMV enhancer)-(chicken β-action promoter)-(β-globin intron II)-(red-/green-emitting luciferase)-(IRES)-(Neo gene)-(SV40 poly A sequence) gene was about 500/1, and the activity elicited by the (CMV promoter)-(β-globin intron II)-(Kozak sequence)-(red-/green-emitting luciferase)-(SV40 poly A sequence) gene was about 10/1 based on the activity elicited by the (CMV enhancer)-(chicken β-action promoter)-(β-globin intron II)-(Kozak sequence)-(red-/green-emitting luciferase)-(IRES)-(Neo gene)-(SV40 poly A sequence) gene. Therefore, it has demonstrated that it is preferable to insert (β-globin intron II)-(Kozak sequence) upstream of the enzyme gene, which is a region which does not directly affect the transcription activity in order to stably express the green-emitting luciferase gene from the rail road worm and determine the gene transcription activity. This is believed to attribute to the promotion of translation efficiency due to the Kozak sequence and the stabilization of mRNA due to the β-globin intron II. It has been demonstrated that the promotion of efficiency of and the stabilization of the transcript including the luciferase gene are keys for practical application.

EXAMPLE 2

Figure 3:
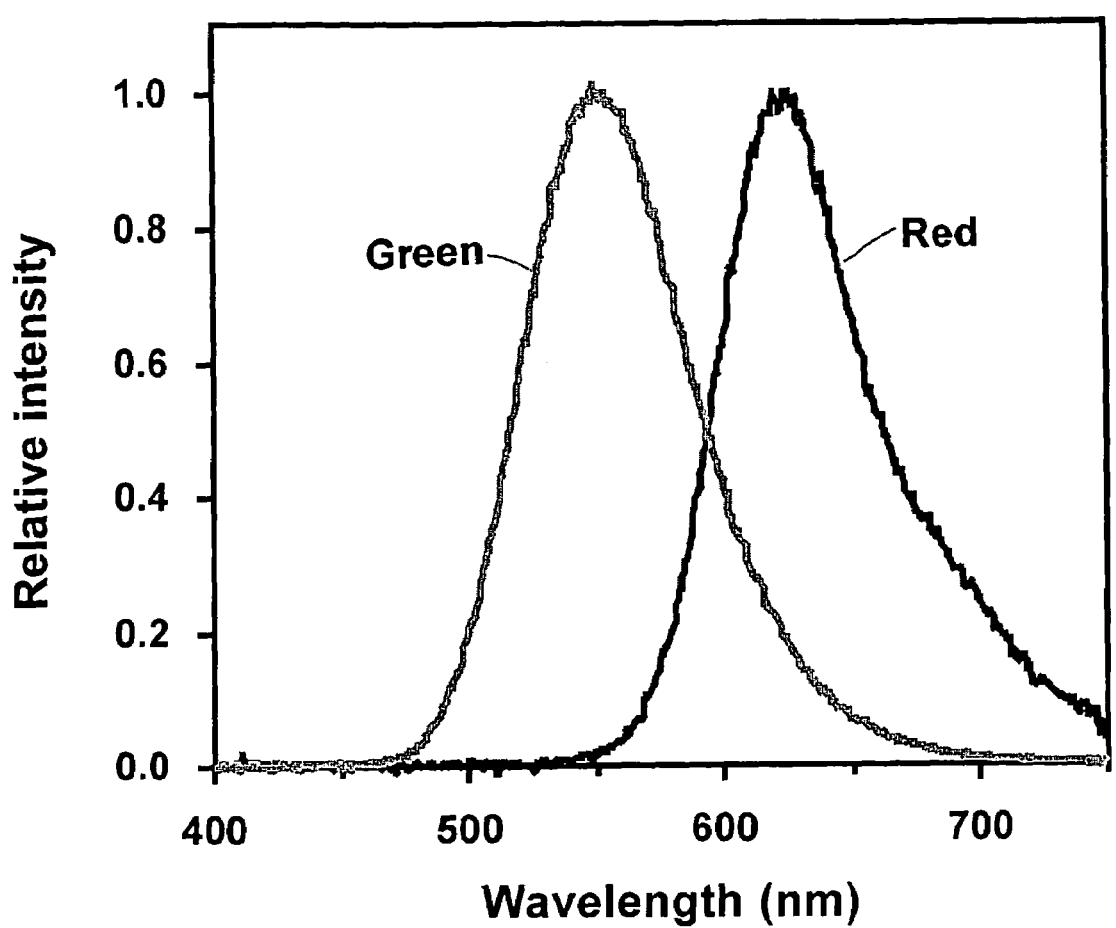
FIG. 3 shows luminescence spectra of a red-emitting luciferase and a green-emitting luciferase from a rail road worm produced in cultured mammalian cells.

Luminescence spectra of the red-emitting luciferase gene and the green-emitting luciferase gene from the rail road worm expressed in the mammalian cells were analyzed. To 15 μL of an extract solution of cells into which the (CMV enhancer)-(chicken β-action promoter)-(β-globin intron II)-(Kozak sequence)-(red-/green-emitting luciferase)-(SV40 poly A sequence) genes which exhibited the highest activity had been introduced, 15 μL of PicaGene was added, and the luminescence spectrum was determined using a weak luminescence spectrum measuring apparatus supplied from ATTO Corporation. FIG. 3 shows the luminescence spectra when the spectrum was expressed singly, the maximum luminescence wavelengths of 630 nm and 550 nm were observed in the red-emitting luciferase and the green-emitting luciferase, respectively. These spectra were not affected by pH and a surrounding solutions, and were not changed at all.

EXAMPLE 3

Figure 4:
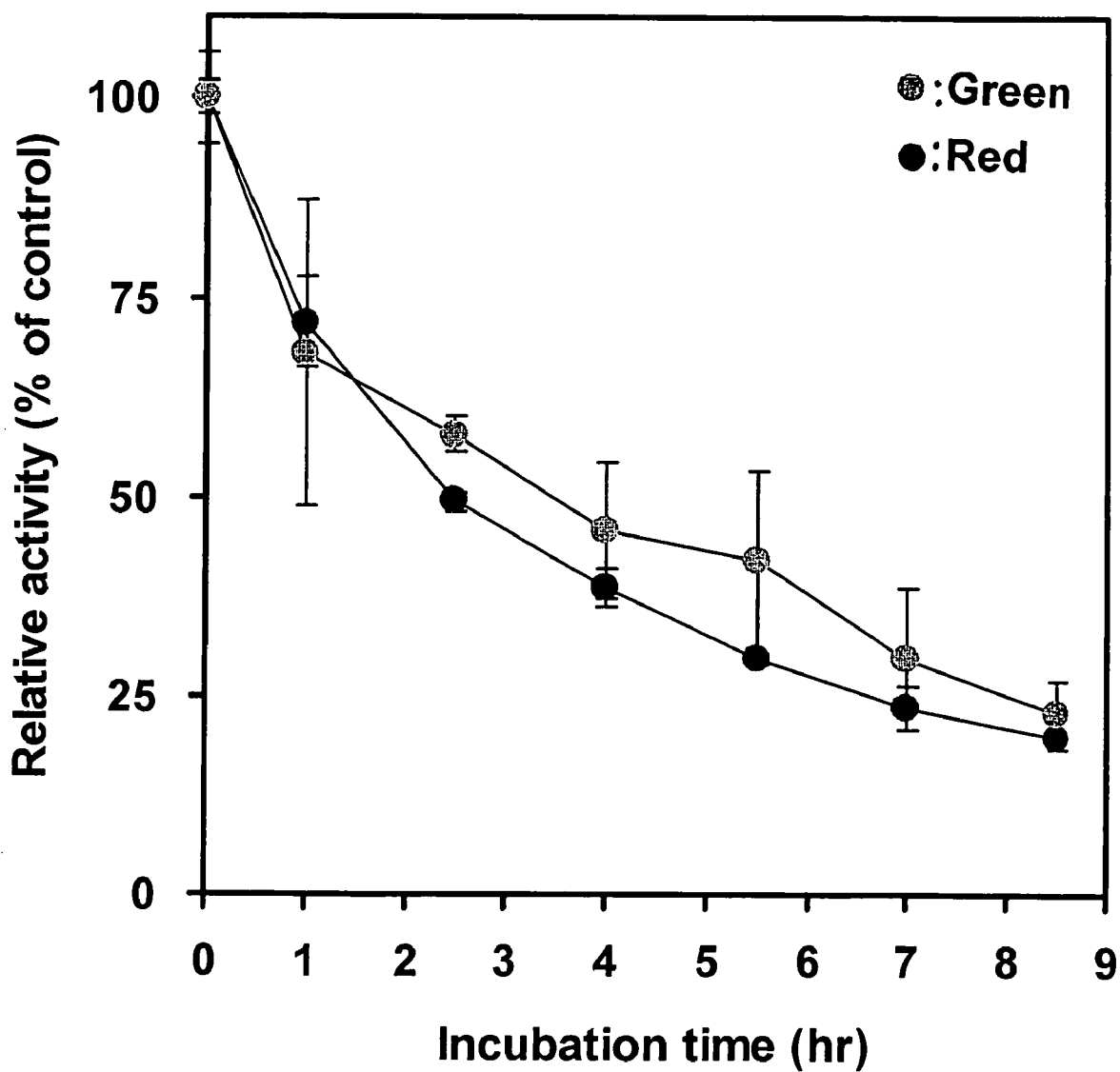
FIG. 4 shows intracellular lifespan of a red-emitting luciferase and a green-emitting luciferase from a rail road worm produced in cultured mammalian cells.

Lifespan in the cells of the red-emitting luciferase gene and the green-emitting luciferase gene from the rail road worm expressed in the mammalian cells was evaluated. The cells into which the (CMV enhancer)-(chicken β-action promoter)-(β-globin intron II)-(Kozak sequence)-(red-emitting, green-emitting luciferase)-(IRES)-(Neo gene)-(SV40 poly A sequence) genes had been introduced were used. Cultured fibroblast cells, NIH3T3 cells were transfected with the above luciferase gene to be expressed in the cells by a lipofection method. Forty-eight hours after the transfection, the medium was replaced with a medium containing 100 μM of a protein synthesis inhibitor, cycloheximide, and the cells were cultured for 30 min. Subsequently, the luminescence activity was determined with time by the same method as that in Example 1. As a result, for both red and green-emitting luciferases, the activity was reduced in the similar time course, and a half life of each enzyme in the cells was about 3.5 hours (FIG. 4).

EXAMPLE 4

The red-emitting luciferase gene and the green-emitting luciferase gene from the rail road worm, the (CMV enhancer)-(chicken β-action promoter)-(β-globin intron II)-(Kozak sequence)-(red-/green-emitting luciferase)-(SV40 poly A sequence) genes were co-expressed in the cultured fibroblast cells NIH3T3. The luminescence spectrum of the red-emitting luciferase gene and the green-emitting luciferase gene from the rail road worm in a cell extract solution obtained by lysing the co-expressing cells was determined by the same technique as that in Example 2. FIG. 5 shows the luminescence spectrum of the co-expressing cells. Two peaks were observed because the red-emitting luciferase and the green-emitting luciferase emit lights. This is a result of simultaneously determining two gene transcription activities. When these luminescence activities is determined by a luminometer using a photomultiplier, a total sum of the luminescence activities of two red and green-emitting luciferase genes from the rail road is observed. Thus, to determine only the luminescence activity of the green-emitting luciferase, the light of the red-emitting luciferase was cut off. Evaluating from the luminescence spectrum, a cut off filter of light wavelengths represented by a dot line in FIG. 5 was selected. By the use of this filter, 8% of the green-emitting luciferase activity and 76% of red-emitting luciferase activity can be detected, and by converting it is possible to evaluate emitted light intensities from the red- and green-emitting luciferases and abundance thereof.

EXAMPLE 5

Figure 6:
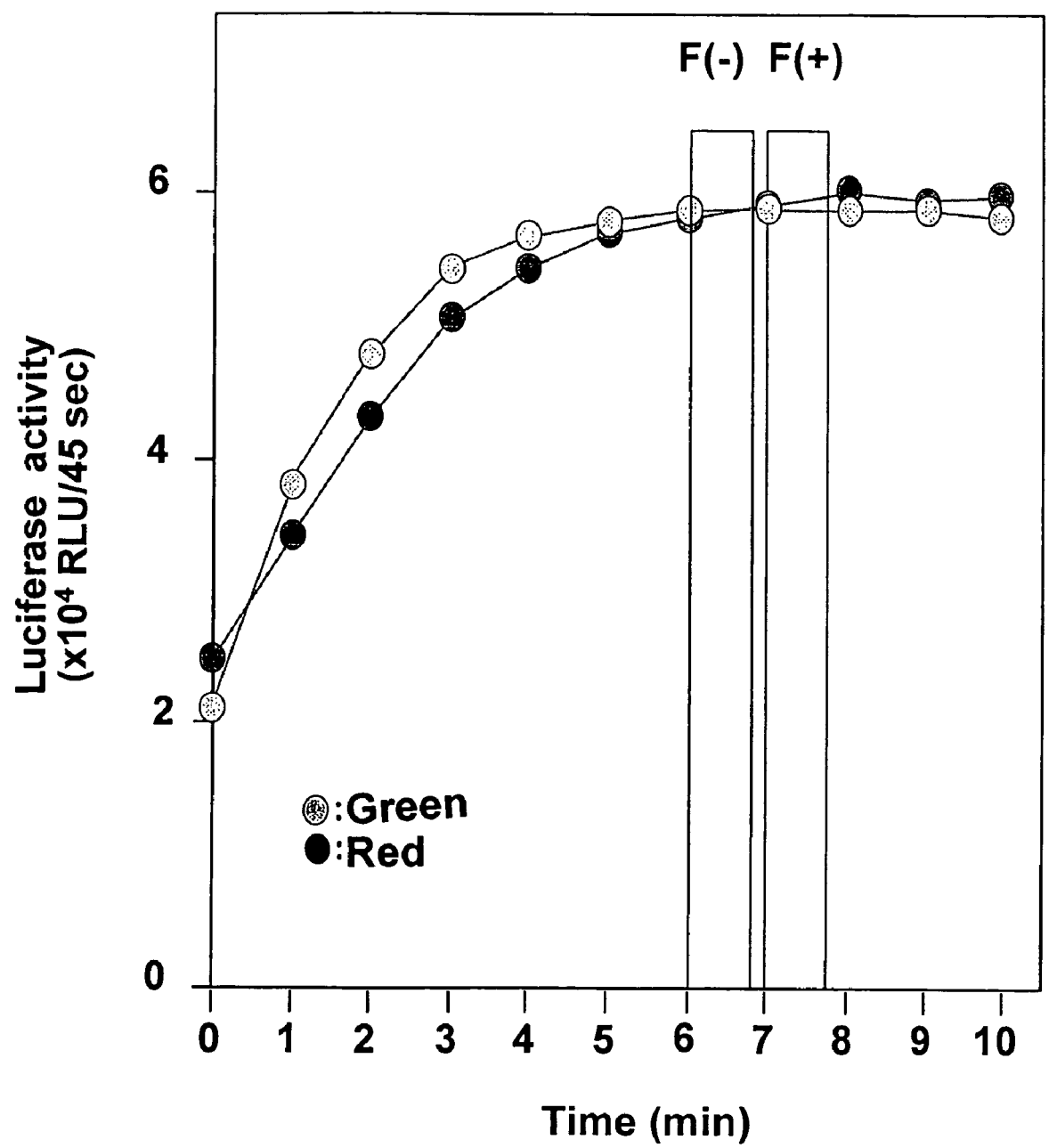
FIG. 6 shows luminescence reaction curves and luminescence activity determining time of a red-emitting luciferase and a green-emitting luciferase.

To 50 μL of a cell extract solution containing the red-emitting luciferase and the green-emitting luciferase, 50 μL of PicaGene was added, and the luminescence activity was measured with one min intervals using a dish type luminometer AB2500 supplied from ATTO Corporation to yield luminescence reaction curves as shown in FIG. 6. The activity was not stabilized within 5 min after the start of the reaction, but both activities were stabilized after 6 min. Thus, when the luminescence activity in the cells in which the red-emitting luciferase gene and the green-emitting luciferase gene had been co-expressed was measured, the activity was measured at a time zone at which the luminescence reaction was stable. A measuring procedure is as follows: 1) the emitted light intensity is measured without a filter (color filter R54 type supplied from Hoya Corporation) (luminescence activities of red- and green-emitting luciferases); 2) the filter (color filter R54 type supplied from Hoya Corporation) determined in Example 4 is inserted in the luminometer, the emitted light intensity is measured to make it the luminance activity of the green-emitting luciferase; and 3) the luminescence activity of the red-emitting luciferase is calculated by converting a transmittance of the filter (color filter R54 type supplied from Hoya Corporation).

EXAMPLE 6

Figure 7:
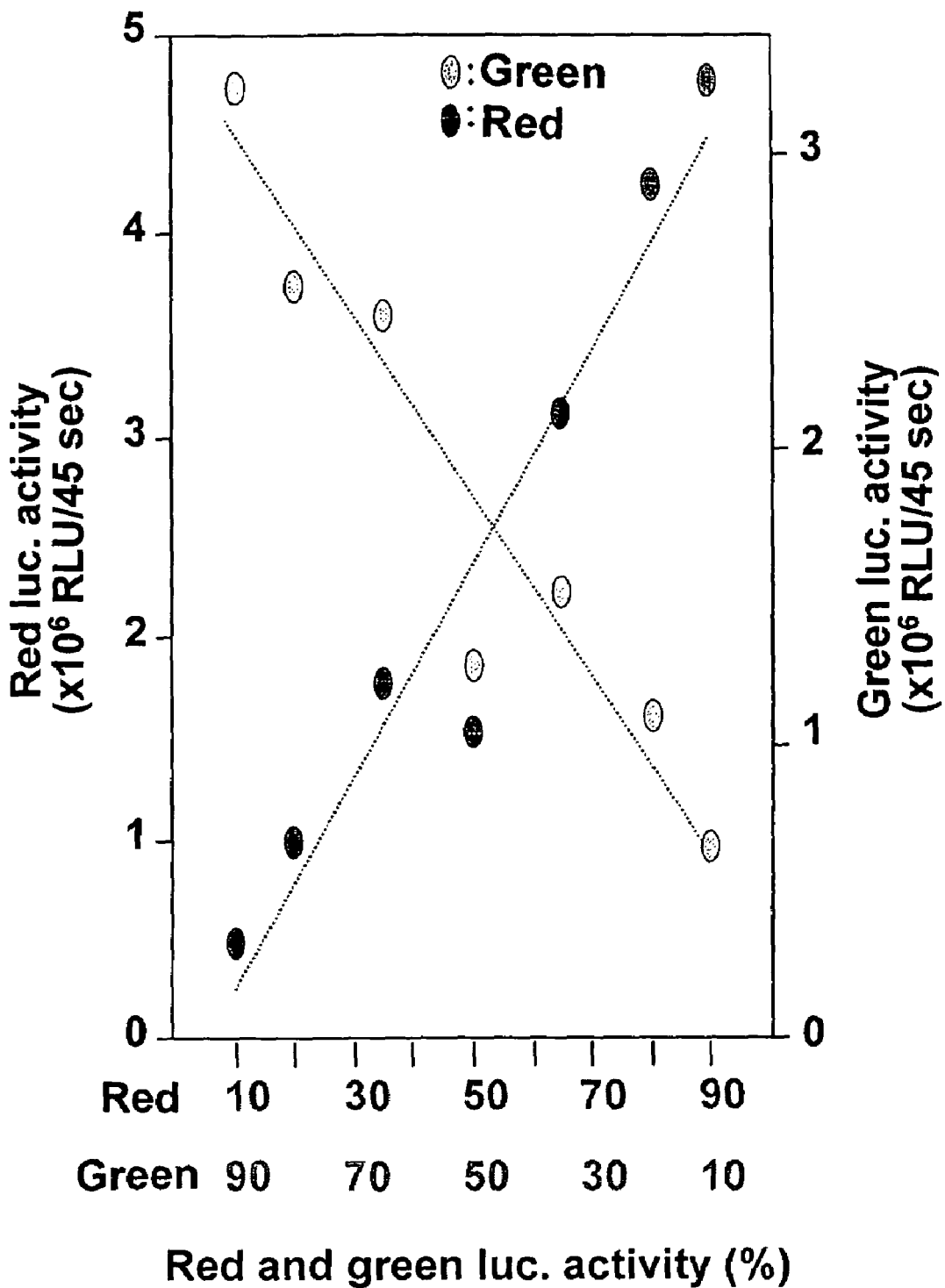
FIG. 7 shows an abundance ratio and luminescence activity of a red-emitting luciferase and a green-emitting luciferase (in the case of using the filter in FIG. 5).

It was examined in a model experiment whether the red-emitting luciferase and the green-emitting luciferase at different abundance ratio can be quantified by the procedure determined in Example 5. In FIG. 7, for samples in which the abundance ratio of the red-emitting luciferase and the green-emitting luciferase had been changed, 1) total intensities of emitted light were measured; 2) only the green-emitting luciferase was measured, and 3) the amounts of the red-emitting and green-emitting luciferases were quantified. As a result, it has been demonstrated that the luminescence activity is changed in a linear relationship with the abundance ratio thereof. This indicates that the amounts of the red-emitting luciferase and the green-emitting luciferase which have shown different expressed amounts in the cells can be quantified by the luminometer to which the color filter (color filter R54 type supplied from Hoya Corporation) was inserted.

EXAMPLE 7

Figure 8:
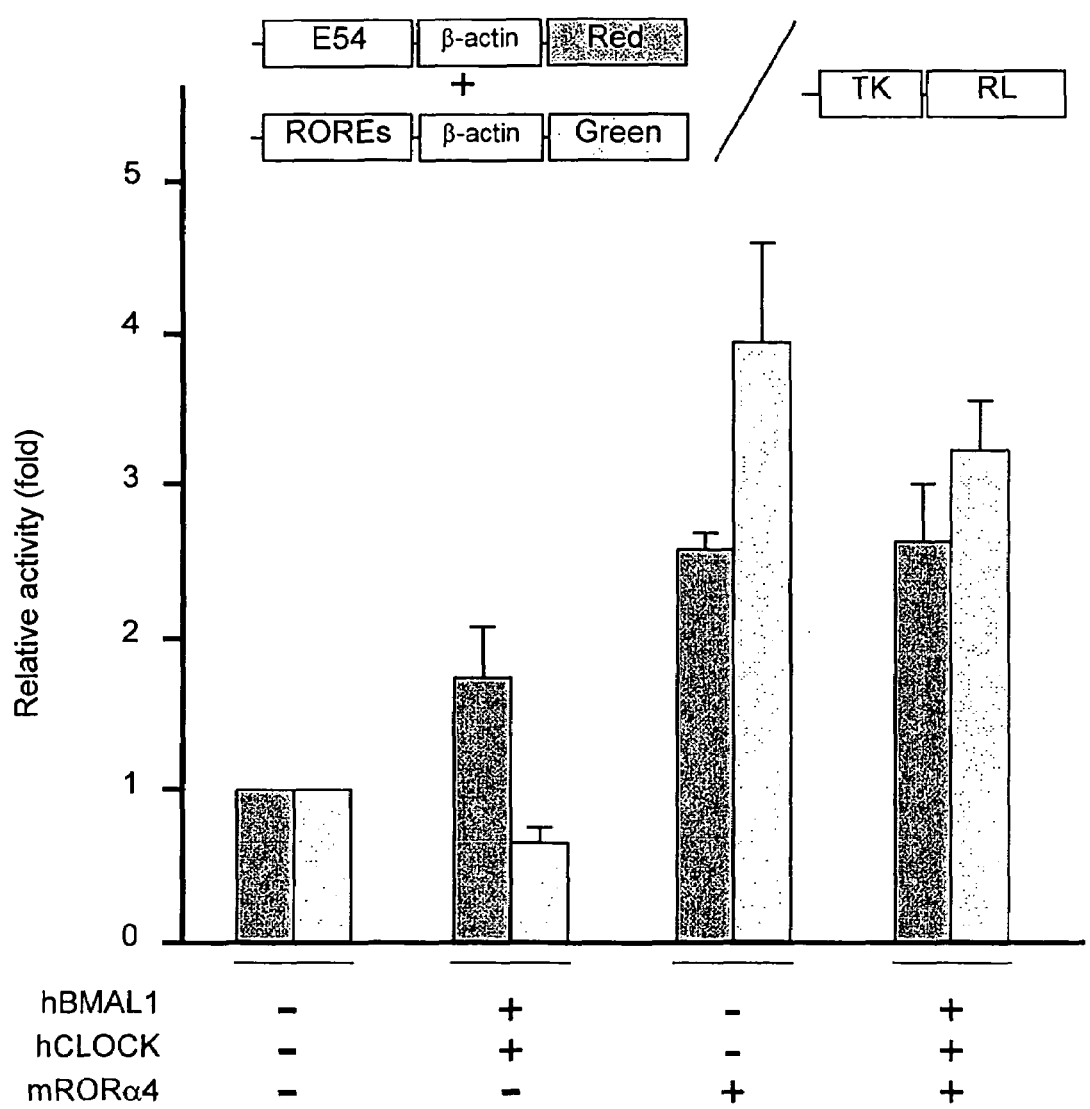
FIG. 8 shows a result of an actual multiple transcription activity determination, i.e., simultaneously determining two transcription activities by lights from a red-emitting luciferase and a green-emitting luciferase, determining the transcription activity of a standard gene by the light from a blue-emitting luciferase, and standardizing the two transcription activities.

To examine an availability of the present system, the gene transcription activities of two clock genes were measured, and standardized using simultaneously a promoter which exhibited the constant gene transcription activity as the third gene transcription activity. Specifically, the NIH3T3 cells were co-transfected with an (E54), an element linking an E-box 3, 4, 5 in mouse Per promoter-(chicken β-action promoter)-(β-globin intron II)-(Kozak sequence)-(red-emitting luciferase)-(SV40 poly A sequence) gene and an REV-ERV/ROR element 1,2 (RORE) in mouse BMAL1 promoter-(chicken β-action promoter)-(β-globin intron II)-(Kozak sequence)-(green-emitting luciferase)-(SV40 poly A sequence) gene, and a blue-emitting luciferase vector for the standardization (phRL-TK, Promega) together with human BMAL1, human CLOCK, and mouse ROR-4 expression vector. After 24 hours, the cells were lysed, and luciferase luminescence wavelengths in the cells were analyzed using a spectrometer. As a result, the luminescence wavelengths from these two luciferases were detected, and these showed the same luminescence spectrum as that when the individual luciferase alone was expressed. Thus, the luminescence activity of the red- and green-emitting luciferases was measured. The transcription activities obtained by further standardizing these activity values with the activity value of the blue-emitting luciferase are shown in FIG. 8. In separate experiments, it has been known that when BMAL1 and CLOCK proteins are expressed in the cells, the element (E54) promoter linking the E-box 3, 4, 5 is activated and an (RORα) promoter is inactivated whereas when the mouse ROR-4 is expressed in the cells, the (RORα) promoter is highly activated. The activities of the red- and green-emitting luciferases simultaneously measured in the present experiment quantitatively show the transcription activity difference of (E54) promoter and (RORα) promoter.

EXAMPLE 8

Figure 9:
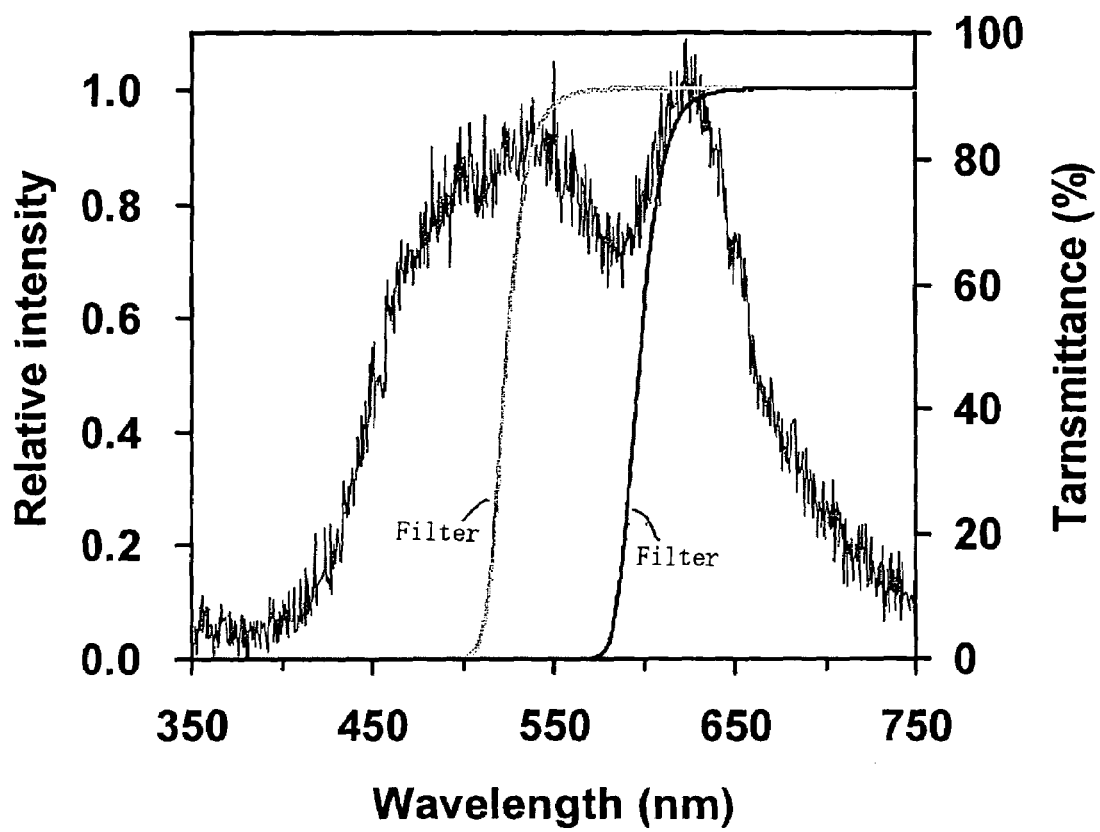
FIG. 9 shows a simultaneous luminescence spectrum of a red-emitting luciferase, a green-emitting luciferase and a blue-emitting luciferase produced in cultured mammalian cells and property of filters used for color identification (transmittance of lights).

The red-emitting luciferase gene and the green-emitting luciferase gene from the rail road worm, (CMV enhancer)-(chicken β-action promoter)-(β-globin intron II)-(Kozak sequence)-(red-/green-emitting luciferase)-(SV40 poly A sequence) genes and the blue-emitting luciferase vector (phRL-TK, Promega) were co-expressed in the cultured fibroblast cells NIH3T3. The co-expressing cells were lysed, and the luminescence spectrum of the red-emitting luciferase and the green-emitting luciferase from the rail road worm and the blue-emitting luciferase from *Renilla* in a cell extract solution was measured by the same technique as that in Example 2. FIG. 9 shows the luminescence spectrum of the co-expressing cells. Three peaks emitted from the red-, green- and blue-emitting-luciferases were observed, and heights of the peak reflect heights of respective promoter activities. The transcription activities of three genes can be evaluated by converting to the intensity of emitted red, green or blue light using a an emitted light intensity determining apparatus with filters capable of identifying the emitted light colors.

EXAMPLE 9

The NIH3T3 cells were co-transfected with the red-emitting luciferase gene and the green-emitting luciferase gene from the rail road worm, (CMV enhancer)-(chicken β-action promoter)-(β-globin intron II)-(Kozak sequence)-(red-/green-emitting luciferase)-(SV40 poly A sequence) genes by lipofection. After culturing for 16 hours, the medium was replaced with a medium containing 100 nM dexamethasone, and the cells were cultured for 2 hours. Subsequently, the medium was replaced with a medium containing 100 μM firefly luciferin, and the luminescence activity of the red- and green-emitting luciferases was continuously measured using the dish type luminometer AB2500 supplied from ATTO Corporation. FIG. 10 shows the result of continuously measuring the transcription activity. If using a continuous emitted light intensity determining apparatus which identifies the emitted light colors, it is possible to continuously measure two transcription activities.

EXAMPLE 10

Figure 13:
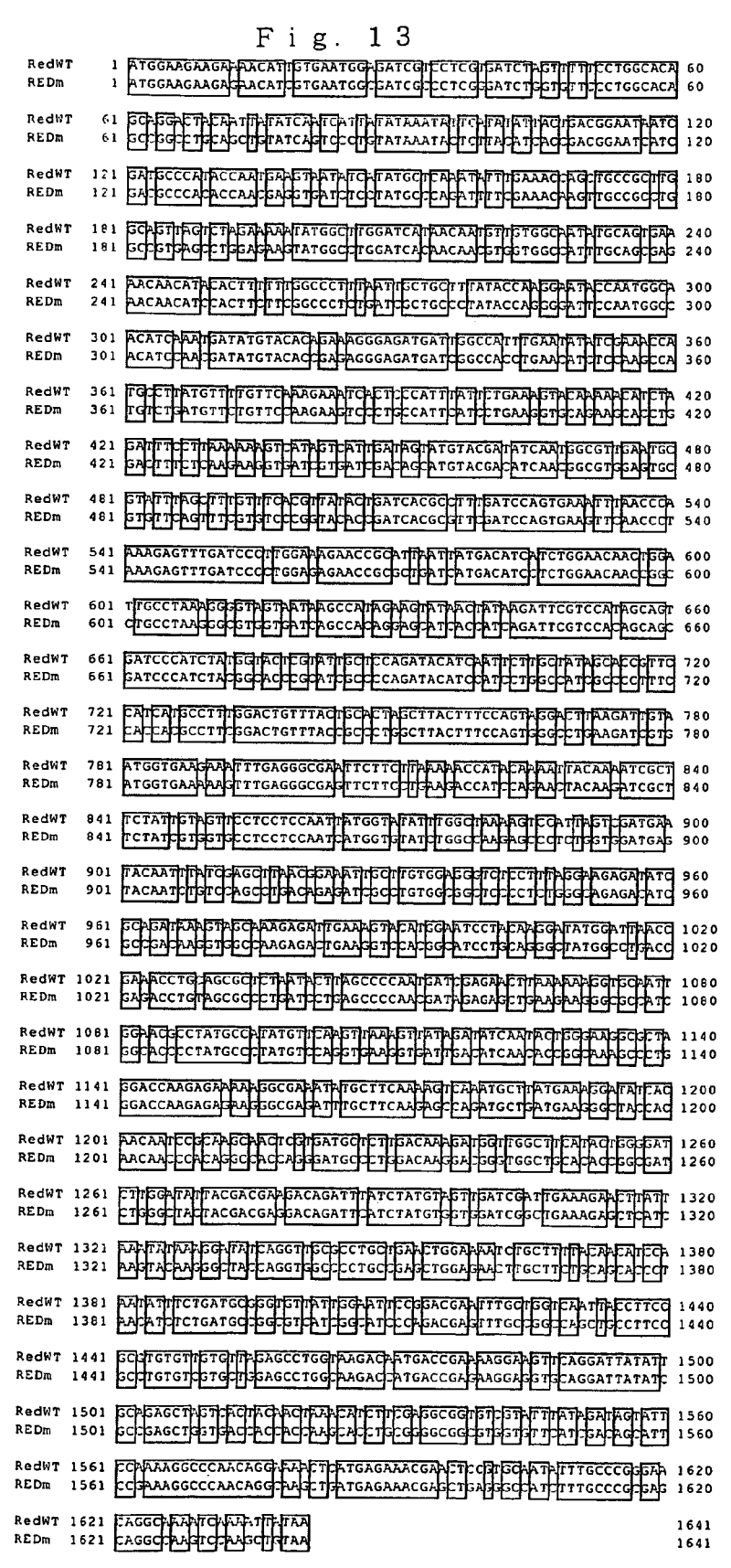
Figure 14:
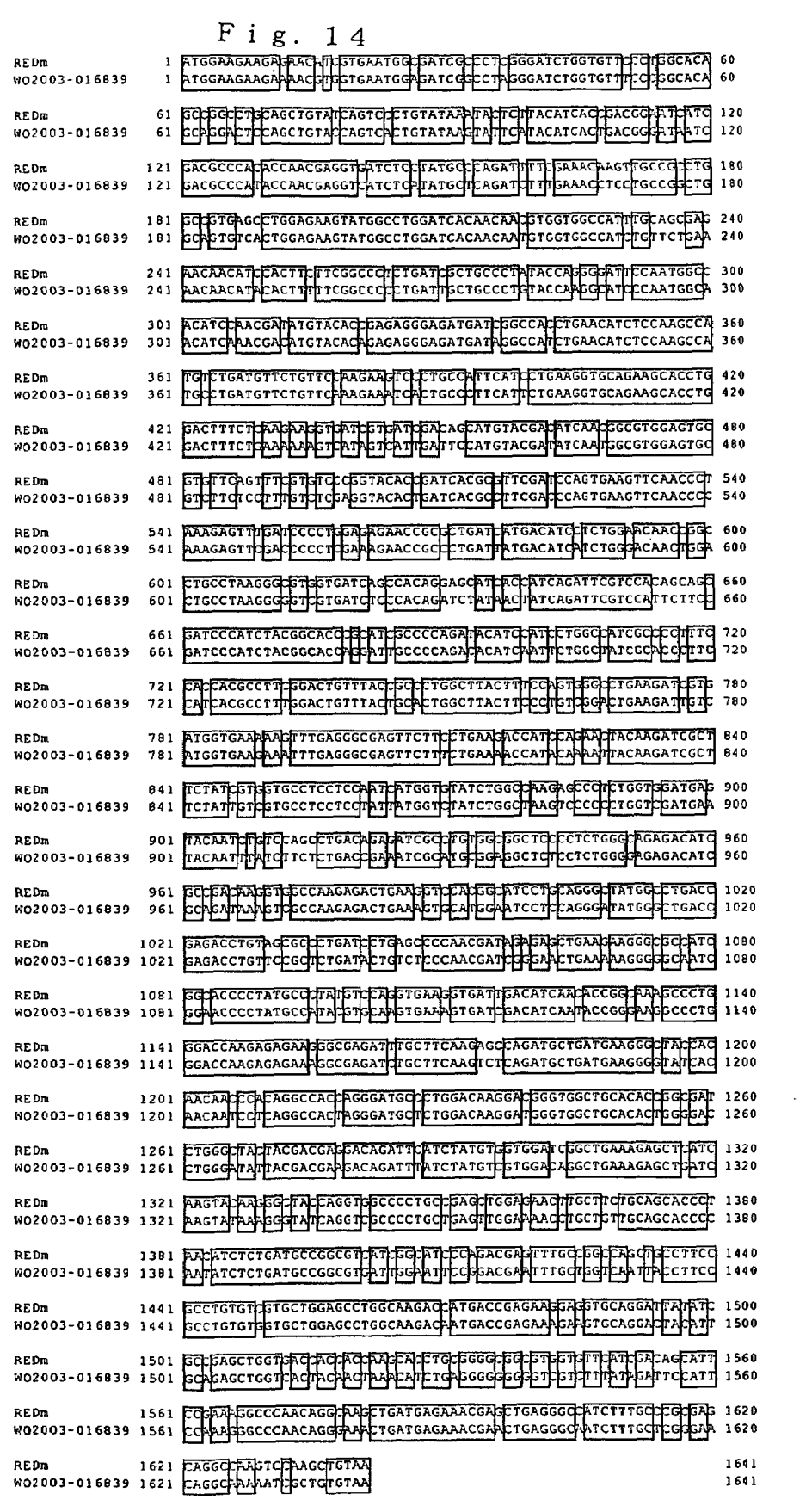

To stably express in the mammalian cells, the sequence of the red-emitting luciferase gene was designed with keeping the followings in mind. By (1) the changes of 34 transcription factor binding sites (48 DNA sequences) (Table 4); (2) the changes of 279 DNA sequences for making the codon use frequency close to the mammalian use frequency (Table 5); and (3) the changes of 15 common restriction enzyme sites (4 in 45 DNA sequences are the same as those of the transcription factor binding sites) (Table 6), the sequence of SEQ ID NO:7 was designed and a construct (SEQ ID NO:7) was artificially made. This sequence has 77.5% homology with the wild-type red-emitting luciferase gene (SEQ ID NO:3) from the rail road worm and 82.8% homology with the red-emitting luciferase mutant described in WO 2003/016839 (FIGS. 13 and 14).

TABLE 4

| Predicted transcription factor | Position number | Mutant | sequence (Italic means a mutated part) |
|---|---|---|---|
| Octamer-binding factor 1 | 89-103 | (A99T) | cagcaggactacaattatatcaatcattat ataaatattc*tt*at a ttactgacggaataatcgatgcccatacca |
| Pit1, GHF-1 pituitary specific pou domain transcription factor | 91-101 | (T96C) (A99G) | gcaggactacaattatatcaatcattatat aaata*ctcg*ta ta ttactgacggaataatcgatgcccatac |
| Myf5 myogenic bHLH protein | 164-178 | (C168A) (C171T) | caatgaagtaatatcatatgctcaaatatt tgaaac*aagt*tgcc gct tggcagttagtctagaaaaatatggcttgg |
| E2F, involved in cell cycle regulation, interacts with Rb p107 protein | 186-200 | (A195G) | aatatttgaaaccagctgccgcttggcagt tagtctaga*g*aaat a tggcttggatcataacaatgttgtggcaat |
| cellular and viral TATA box elements | 268-284 | (T276C) (T277C) | gaaaacaacatacactttttttggcccttta attgctgc*cc*tata cca aggaataccaatggcaacatcaaatgatat |
| Ikaros 3, potential regulator of lymphocyte differentiation | 281-293 | (A288G) | Acttttttggcccttttaattgctgctttat accaagg*g*atacc aatggcaacatcaaatgatatgtacacaga |
| cellular and viral CCAAT box | 332-342 | (T336C) | catcaaatgatatgtacacagaaagggaga tgat*c*ggccat tt gaatatatcgaaaccatgccttatgttt |
| Mammalian C-type LTR TATA box | 424-440 | (C426T) (T429C) | tttattctgaaagtacaaaaacatctagat tt*tct c*aaaaaagt cat agtcattgatagtatgtacgatatcaatgg |
| TCF/LEF-1, involved in the Wnt signal transduction pathway | 484-500 | (C489T) | atgtacgatatcaatggcgttgaatgcgta ttta*gt*ttgtttc acg ttatactgatcacgcctttgatccagtgaa |
| X-box-binding protein 1 | 491-505 | (T501G) | atatcaatggcgttgaatgcgtatttagct ttgtttcacgg*t*at a ctgatcacgcctttgatccagtgaaattta |
| TCF/LEF-1, involved in the Wnt signal transduction pathway | 511-527 | (C516G) (T519C) | gtatttagctttgtttcacgttatactgat cacg*c*gtt*c*gatcc agt gaaatttaacccaaaagagtttgatccctt |
| Hox-1.3, vertebrate homeobox protein | 562-578 | (A570G) (T571C) | tttaacccaaaagagtttgatcccttggaa agaaccgc*gc*taat tat gacatcatctggaacaactggattgcctaa |
| COMP1, cooperates with myogenic proteins in multicomponent complex | 593-613 | (A600C) (T601C) | gaaccgcattaattatgacatcatctggaa caactgg*cc*tgcct aaagggg tagtaataagccatagaagtataactataa |

TABLE 4-continued

| Predicted transcription factor | Position number | Mutant sequence (Italic means a mutated part) |
|---|---|---|
| Prostate-specific homeodomain protein NKX3.1 | 626-638 (A630G) | ctggattgcctaaaggggtagtaataagcc ataggagtataac tataagattcgtccatagcagtgatcccat |
| POU factor Brn-2 (N-Oct 3) | 817-833 (A822C) | aagaaatttgagggcgaattcttcttaaaa accatccaaaatta caa aatcgcttctattgtagttcctcctccaat |
| Pu.1 (Pu120) Ets-like transcription factor identified in lymphoid B-cells | 844-860 (T828C) | agggcgaattcttcttaaaaaccatacaaa actacaaaatc gc ttctattgtagttcctcctccaattatg |
| Hox-1.3, vertebrate homeobox protein | 880-896 (A888T) (T889C) | gttcctcctccaattatggtatatttggct aaaagtcctctagt cga tgaatacaatttatcgagcttaacggaaat |
| transcriptional repressor CDP | 903-919 (T907C) (A909G) | tttggctaaaagtccattagtcgatgaata caatctgtcgagc ttaacggaaattgcttgtggagggtctcct |
| complex of Lmo2 bound to Tal-1, E2A proteins, and GATA-1, half-site 2 | 951-963 (T957C) | ggaaattgcttgtggagggtctcctttagg aagagacatcgca gataaagtagcaaagagattgaaagtacat |
| TCF/LEF-1, involved in the Wnt signal transduction pathway | 967-983 (A975C) | gggtctcctttaggaagagatatcgcagat aaagtagccaagag att gaaagtacatggaatcctacaaggatatgg |
| Prostate-specific homeodomain protein NKX3.1 | 1036-1048 (T1044G) | ggatatggattaaccgaaacctgcagcgct ctaatactgagcc ccaatgatcgagaacttaaaaaaggtgcaa |
| transcriptional repressor CDP | 1049-1065 (T1053C) (C1057A) | ccgaaacctgcagcgctctaatacttagcc ccaacgatagagaa ctt aaaaaaggtgcaattggaacgcctatgcca |
| Ribonucleoprotein associated zinc finger protein MOK-2 (human) | 1066-1086 (A1071G) | ctaatacttagccccaatgatcgagaactt aaaaagggtgcaat tggaacg cctatgccatatgttcaagttaaagttata |
| Octamer-binding factor 1, POU-specific domain | 1158-1170 (A1161G) (A1164T) | tgggaaggcgctaggaccaagagaaaaagg cgagatttgcttc aaaagtcaaatgcttatgaaaggatatcac |
| Ecotropic viral integration site 1 encoded factor | 1182-1198 (A1191G) (A1194C) | aaaaggcgaaatatgcttcaaaagtcaaat gcttatgaagggct atc acaacaatccgcaagcaactcgtgatgctc |
| Nuclear factor Y (Y-box binding factor) | 1236-1250 (T1242G) | tccgcaagcaactcgtgatgctcttgacaa agatgggtggcttc a tactggggatcttggatattacgacgaaga |
| Prostate-specific homeodomain protein NKX3.1 | 1309-1321 (A1314G) | gacagatttatctatgtagttgatcgattg aaagagcttatta aatataaaggatatcaggttgcgcctgctg |
| Special AT-rich sequence-binding protein 1, predominantly expressed in thymocytes, binds to matrix attachment regions (MARs) | 1314-1330 (T1317C) (T1320C) | atttatctatgtagttgatcgattgaaaga actcatcaaatata aag gatatcaggttgcgcctgctgaactggaaa |
| Octamer-binding factor 1 | 1373-1387 (T1377C) | cgcctgctgaactggaaaatctgcttttac aacacccaaatatt t ctgatgcgggtgttattggaattccggacg |
| POU factor Brn-2 (N-Oct 3) | 1379-1395 (A1380T) | ctgaactggaaaatctgcttttacaacatc ctaatatttctgat gcg ggtgttattggaattccggacgaatttgct |
| Octamer-binding factor 1 | 1399-1413 (T1401C) | ttacaacatccaaatatttctgatgcgggt gtcattggaattcc g gacgaatttgctggtcaattaccttccgcg |
| Binding site for a Pbx1/Meis1 heterodimer | 1422-1438 (A1431G) | tgcgggtgttattggaattccggacgaatt tgctggtcagttac ctt ccgcgtgtgttgtgttagagcctggtaaga |
| GATA-binding factor 2 | 1548-1560 (A1551C) (T1554C) | aactaaacatcttcgaggcggtgtcgtatt tatcgacagtatt ccaaaaggcccaacaggaaaactcatgaga |
| Cart-1 (cartilage homeoprotein 1) | 1624-1640 (T1636C) | gaactccgtgcaatatttgcccgggaacag gcaaaatcaaaact ata a |

TABLE 5

| Amino Acid | Codon | RED complete # | RED complete % | RED-mutant # | RED-mutant % |
|---|---|---|---|---|---|
| Met | ATG | 14 | 100.0 | 14 | 100.0 |
| Trp | TGG | 1 | 100.0 | 1 | 100.0 |
| Glu | GAA | 26 | 83.9 | 3 | 9.7 |
|  | GAG | 5 | 16.1 | 28 | 90.3 |
| Phe | TTT | 19 | 76.0 | 7 | 28.0 |
|  | TTC | 6 | 24.0 | 18 | 72.0 |
| Asp | GAT | 25 | 83.3 | 16 | 53.3 |
|  | GAC | 5 | 16.7 | 14 | 46.7 |
| Cys | TGT | 3 | 33.3 | 5 | 55.6 |
|  | TGC | 6 | 66.7 | 4 | 44.4 |
| His | CAT | 12 | 80.0 | 0 | 0.0 |
|  | CAC | 3 | 20.0 | 15 | 100.0 |
| Gln | CAA | 12 | 80.0 | 0 | 0.0 |
|  | CAG | 3 | 20.0 | 15 | 100.0 |
| Asn | AAT | 13 | 65.0 | 2 | 10.0 |
|  | AAC | 7 | 35.0 | 18 | 90.0 |
| Tyr | TAT | 17 | 70.8 | 9 | 37.5 |
|  | TAC | 7 | 29.2 | 15 | 62.5 |
| Lys | AAA | 32 | 82.1 | 6 | 15.4 |
|  | AAG | 7 | 17.9 | 33 | 84.6 |
| Ile | ATT | 20 | 43.5 | 6 | 13.0 |
|  | ATC | 8 | 17.4 | 40 | 87.0 |
|  | ATA | 18 | 39.1 | 0 | 0.0 |
| *** | TAA | 1 | 100.0 | 1 | 100.0 |
|  | TAG | 0 | 0.0 | 0 | 0.0 |
|  | TGA | 0 | 0.0 | 0 | 0.0 |
| Thr | ACT | 11 | 37.9 | 0 | 0.0 |
|  | ACC | 7 | 24.1 | 21 | 72.4 |
|  | ACA | 9 | 31.0 | 8 | 27.6 |
|  | ACG | 2 | 6.9 | 0 | 0.0 |
| Pro | CCT | 11 | 35.5 | 15 | 48.4 |
|  | CCC | 3 | 9.7 | 4 | 12.9 |
|  | CCA | 14 | 45.2 | 11 | 35.5 |
|  | CCG | 3 | 9.7 | 1 | 3.2 |
| Ala | GCT | 13 | 37.1 | 3 | 8.6 |
|  | GCC | 4 | 11.4 | 30 | 85.7 |
|  | GCA | 14 | 40.0 | 0 | 0.0 |
|  | GCG | 4 | 11.4 | 2 | 5.7 |
| Gly | GGT | 7 | 17.5 | 0 | 0.0 |
|  | GGC | 9 | 22.5 | 34 | 85.0 |
|  | GGA | 20 | 50.0 | 4 | 10.0 |
|  | GGG | 4 | 10.0 | 2 | 5.0 |
| Val | GTT | 14 | 36.8 | 0 | 0.0 |
|  | GTC | 6 | 15.8 | 5 | 13.2 |
|  | GTA | 13 | 34.2 | 0 | 0.0 |
|  | GTG | 5 | 13.2 | 33 | 86.8 |
| Arg | AGA | 8 | 40.0 | 8 | 40.0 |
|  | AGG | 1 | 5.0 | 4 | 20.0 |
|  | CGT | 6 | 30.0 | 0 | 0.0 |
|  | CGC | 1 | 5.0 | 4 | 20.0 |
|  | CGA | 3 | 15.0 | 0 | 0.0 |
|  | CGG | 1 | 5.0 | 4 | 20.0 |
| Ser | AGT | 8 | 25.0 | 2 | 6.3 |
|  | AGC | 7 | 21.9 | 13 | 40.6 |
|  | TCT | 4 | 12.5 | 4 | 12.5 |
|  | TCC | 1 | 3.1 | 13 | 40.6 |
|  | TCA | 10 | 31.3 | 0 | 0.0 |
|  | TCG | 2 | 6.3 | 0 | 0.0 |
| Leu | CTT | 13 | 25.0 | 1 | 1.9 |
|  | CTC | 3 | 5.8 | 2 | 3.8 |
|  | CTA | 9 | 17.3 | 1 | 1.9 |
|  | CTG | 4 | 7.7 | 47 | 90.4 |
|  | TTA | 15 | 28.8 | 0 | 0.0 |
|  | TTG | 8 | 15.4 | 1 | 1.9 |

TABLE 6

| Restriction enzyme site | Sequence before change | Sequence after change |
|---|---|---|
| 35 BssSI | Ctggtg | Ctcgga |
| 92 SspI | Aatatt | Aatact |
| 118 ClaI | Atcgat | Atcgac |
| 146 NdeI | Catatg | Cctatg |
| 155 SspI | Aatatt | Gatttt |
| 189 XbaI | Tctaga | Cctgga |
| 282 EcoT14I | Ccaagg | Ccaggg |
| 417 XbaI | Tctaga | Cctgga |
| 460 EcoRV | Gatatc | Gacatc |
| 524 ApoI | Aaattt | Aagttc |
| 553 EcoT14I | Ccttgg | Ccctgg |
| 570 PshBI | Attaat | Gctgat |
| 769 AflIII | Cttaag | Ctgaag |
| 790 ApoI | Aaattt | Aagttt |
| 802 ApoI, EcoRI | Gaattc | Gagttc |
| 955 EcoRV | Gatatc | Gacatc |
| 1030 Aor51HI | Agcgct | Agcgcc |
| 1075 MunI | Caattg | Ccatcg |
| 1094 NdeI | Catatg | Cctatg |
| 1117 EcoRV | Gatatc | Gacatc |
| 1193 EcoRV | Gatatc | Gctacc |
| 1217 BssSI | Ctcgt | Ccagg |
| 1301 ClaI | Atcgat | Atcggc |
| 1331 EcoRV | Gatatc | Gctacc |
| 1381 SspI | Aatatt | Aacatc |
| 1406 EcoRI, ApoI | Gaattc | Gcatcc |

TABLE 6-continued

| Restriction enzyme site | Sequence before change | Sequence after change |
|---|---|---|
| 1410 AccIII | Tccgga | Cccaga |
| 1417 ApoI | Gaattt | Gagttt |
| 1605 SspI | Aatatt | Catctt |
| 1613 SmaI | Cccggg | Cccgcg |

EXAMPLE 11

Vectors in which a wild-type or mutant luciferase gene was inserted downstream of three kinds of promoters (CMV, SV40 or CAG {CAG: (CMV enhancer)-(chicken β-action promoter)-(β-globin intron II)-(Kozak sequence)} were made (wild-type: CMV-Red, CAG-Red, mutant: CMV-REDm, CAG-REDm). At that time, the vectors in which an SKL sequence known as a peroxisome transfer sequence at the C-terminus had been deleted were made (wild-type: SV40-Red(-SKL), mutant: SV40-REDm(-SKL), CAG-REDm).

Figure 15:
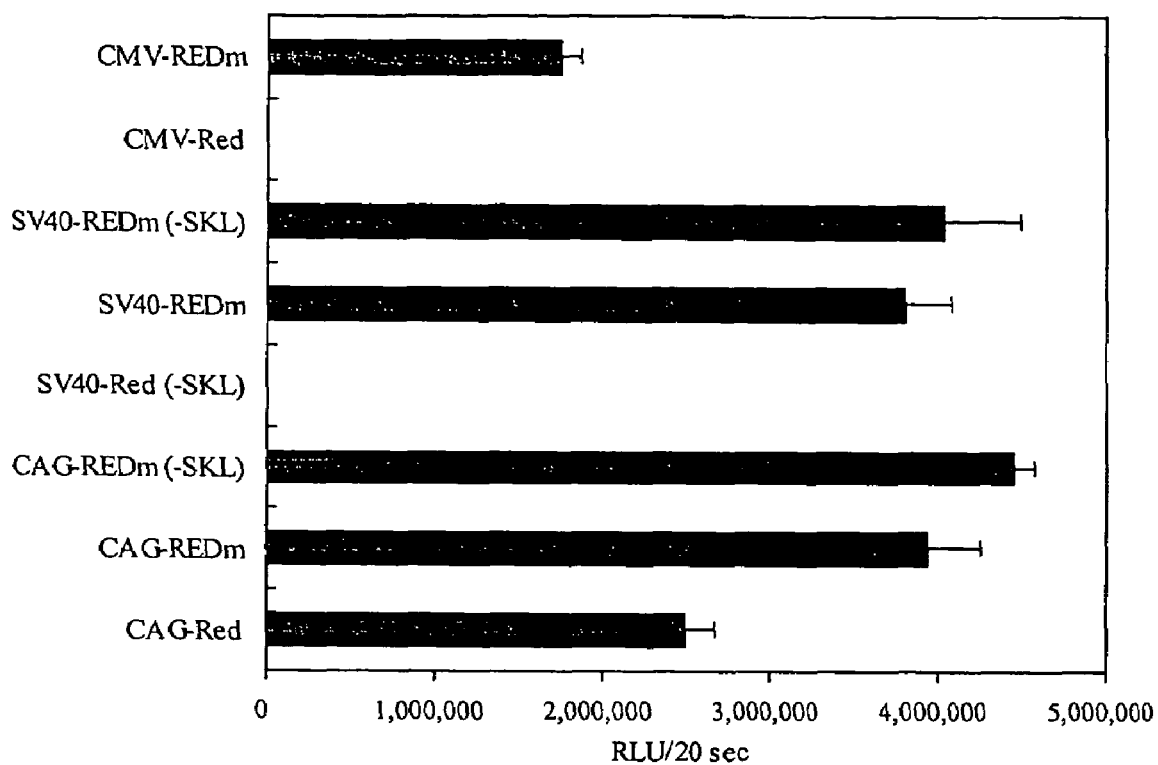
FIG. 15 shows differences in luminescence activity of a wild-type rail road worm red-emitting luciferase and a mutant rail road worm red-emitting luciferase.

The NIH3T3 cells were transfected with each gene using Lipofectamine, and the luminescence activity in the cells after 24 hours was measured (FIG. 15). A luminescent substrate mixed solution (Toyo B-Net Co., Ltd.) and AB2500 supplied from ATTO Corporation were used as the substrate and as a luminescence determining apparatus, respectively for the measurement of the luminescence activity. A sample was made by adding 50 µL of PicaGene to 50 µL of a cell extract solution. The sample containing CMV-Red or SV40-Red(-SKL) showed a value of around 1000 RLU whereas the sample containing CMV-REDm or SV40-REDm(-SKL) showed a value of $2\times10^7$ to $4\times10^7$ RLU. As shown in FIG. 15, the high activity was observed in the sample containing CAG-Red, but in the sample containing its mutant, the activity was increased by about two times. The SKL sequence was believed to be involved in activity increase, but the activity in the sample containing SKL was increased by only several %. From these results, it has been demonstrated that CAG and REDM are useful as reporter genes for analysis of the expression of mammalian genes. By the technique in Example 10, it is possible to stably express the luciferase from rail road worm in the mammalian cells. Therefore, by the similar procedure, the sequence of the green-emitting luciferase gene from rail road worm was modified (SEQ ID NO:16). In the modified sequence, 16 transcription factor binding sites were modified in the wild-type, and it has 76% homology with the wild type.

EXAMPLE 12

Figure 16:
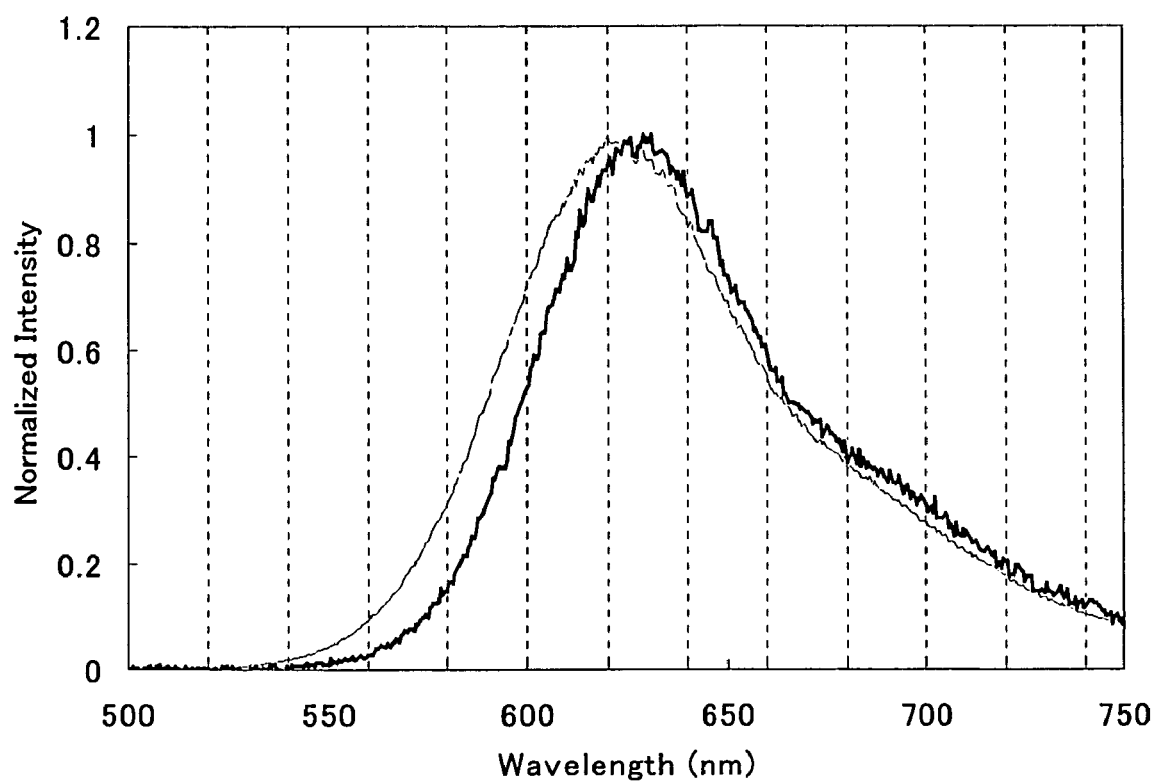
FIG. 16 shows luminescence spectra of a mutant (SEQ ID NO:7) introduced and produced in mammalian cells (mouse NIH3T3 cells, a thick line) and a rail road wild-type (SEQ ID NO:3) produced in insect silk worm cells (a thin line).
Figure 18:
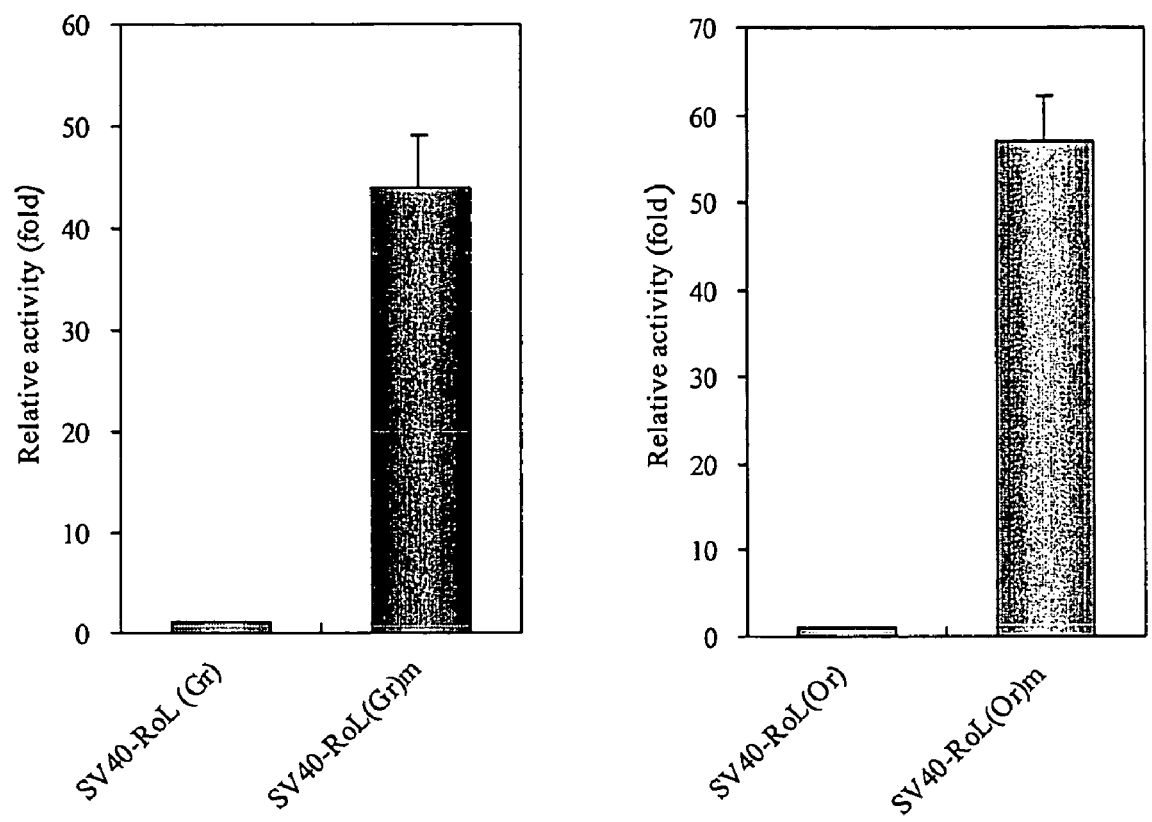
FIG. 18 shows difference in luminescence activity of *Rhagophthalmus ohba* green-emitting luciferase wild-type and mutant and *Rhagophthalmus ohba* orange-emitting luciferase wild type and mutant.

The luminescence spectrum of the red-emitting luciferase gene derived from the rail road worm, expressed in the mammalian cells was analyzed. To 15 µL of an extract solution of the cells (NIH3T3 derived from a mouse, Rat-1 derived from a rat, A543 cells from human) transfected with the CMV-REDm gene whose activity was the highest, 15 µL of PicaGene was added, and the luminescence spectrum was measured using a weak luminescence spectrum determining apparatus supplied from ATTO Corporation. As a reference, the luminescence spectrum in an extract solution of silk worm insect cells transfected with the gene described in SEQ ID NO:3 was also measured. FIG. 16 shows the luminescence spectra expressed in the mouse NIH3T3 cells (bold line) and silk worm insect cells (thin line). The maximum luminescence wavelength in the mouse NIH3T3 cells was 630 nm and that in the silk worm insect cells was around 622 nm. These spectra were not affected by pH and the surrounding solution, and were always displayed as the same spectra. The maximum luminescence wavelength in Rat-1 cells from the rat and A543 cells from the human was also 630 nm.

EXAMPLE 13

In order to stably express in the mammalian cells, in the sequences of wild-type *Rhagophthalmus ohba* green-emitting luciferase (the gene sequence and the amino acid sequence are shown in SEQ ID NOS:8 and 12, respectively.) and the wild-type *Rhagophthalmus ohba* orange-emitting luciferase (the gene sequence and the amino acid sequence are shown in SEQ ID NOS:9 and 13, respectively.), with keeping the followings in mind, constructs were artificially made.

1) Changes of 15 transcription factor binding sites (20 DNA sequences) (Table 7)

2) Changes of 322 DNA sequences for making the codon use frequency close to the mammalian codon usage (Table 8).

3) Changes of 30 common restriction enzyme sites (2 in 49 DNA sequence are the same as those of the transcription factor binding sites) (Table 9).

In Tables 8 and 9, RoLWT represents the wild-type *Rhagophthalmus ohba* luciferase, and RoLm represents the mutant *Rhagophthalmus ohba* luciferase.

The gene sequence of the resulting mutant *Rhagophthalmus ohba* green-emitting luciferase gene and the amino acid sequence thereof are shown in SEQ ID NOS:10 and 14, respectively. The gene sequence of the resulting mutant *Rhagophthalmus ohba* orange-emitting luciferase gene and the amino acid sequence thereof are shown in SEQ ID NOS:11 and 15, respectively.

Figure 17:
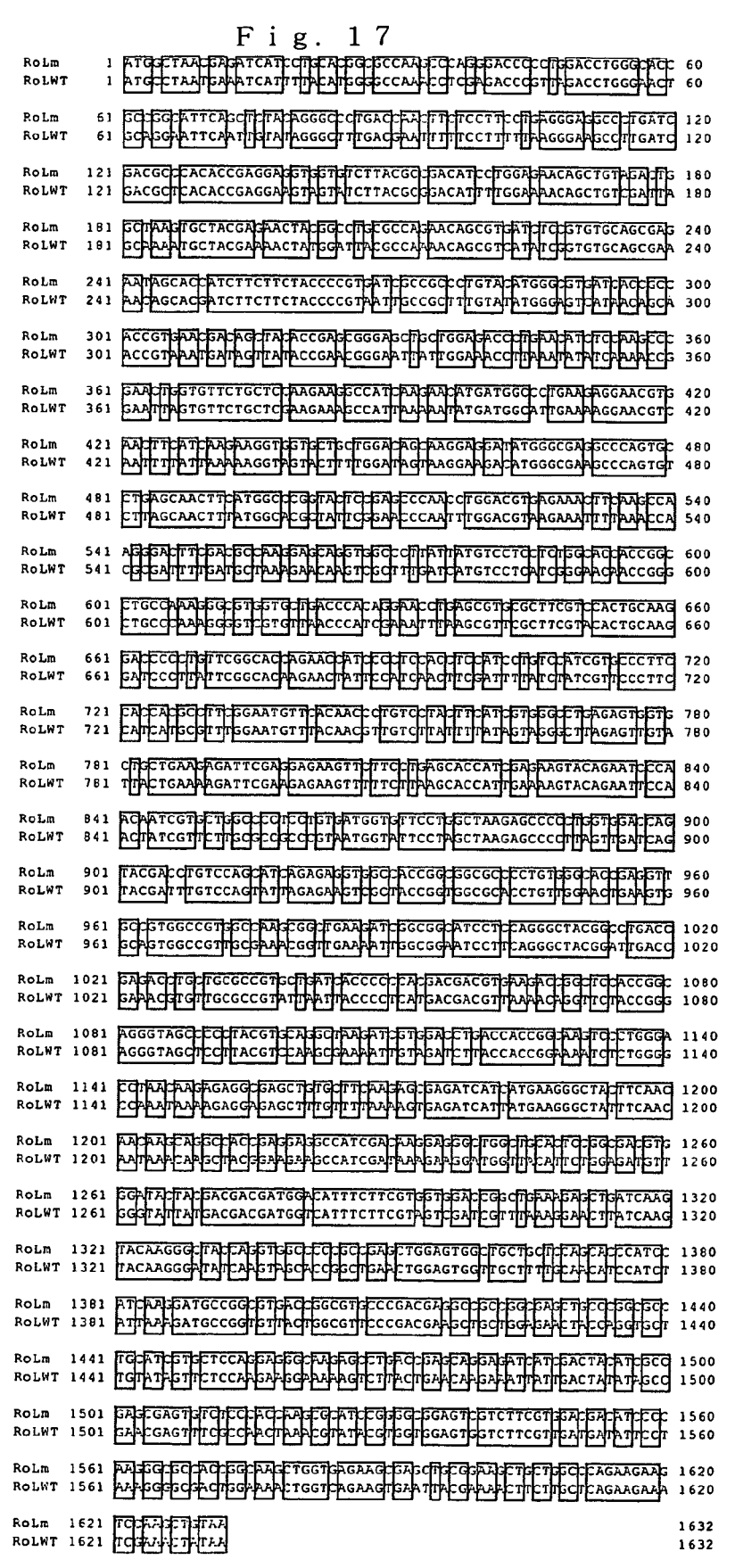

The homology between the mutant *Rhagophthalmus ohba* green-emitting luciferase gene sequence (SEQ ID NO:10) and the wild-type *Rhagophthalmus ohba* green-emitting luciferase gene sequence (SEQ ID NO:8) is 76.0% (FIG. 17)

TABLE 7

| Predicted transcription factor | Mutant number | Mutant sequence (Italic means a mutated part) | |
|---|---|---|---|
| Activator protein 4 | 64-80 | (C69T) | cccagggaccccctggacctgggcaccgcc ggcatt_cag |
| | | (G75C) | ct_ctacag agccctgaccaacttctccttcctgaggga |

TABLE 7-continued

| Predicted transcription factor | Mutant number | Mutant sequence (Italic means a mutated part) |
|---|---|---|
| RAR-related orphan receptor alpha2 | 81-97 | (A81G) cctgggcaccgccggcatccagctgtacag *g*gccctgac caacttct ccttcctgagggaggccctgatcgacgcc |
| Nuclear factor 1 | 169-187 | (C183T) gtggtgtcttacgccgacatcctggagaac agctgtaga ctggc*t*aagt gctacgagaactacggcctgcgccagaac a |
| Progesterone receptor binding site | 237-255 | (C243T) gcgccagaacagcgtgatctccgtgtgcag cgagaa*t*ag caccatcttc ttctacccgtgatcgccgccctgtacat g |
| Tumor suppressor p53 (5' half site) | 458-478 | (C462T) tcaagaaggtggtgctgctggacagcaagg agga*t*atgg gcgaggcccagt gcctgagcaacttcatggcccggtact ccg |
| Tumor suppressor p53 (5' half site) | 563-583 | (G573T) tcaagccaagggacttcgacgccaaggagc aggtggccc (C576T) t*t*at*t*atgtcct cctctggcaccaccggcctgccaaagg gcg |
| Zinc finger transcription factor ZBP-89 | 850-864 | (C858T) atcgagaagtacagaatcccaacaatcgtg ctggcccc*t* (C861T) cc*t*gtg atggtgttcctggccaagagccccctggtg |
| Nuclear factor 1 | 865-883 | (C879T) atcccaacaatcgtgctggccccccccgtg atggtgttc ctggc*t*aaga gccccctggtggaccagtacgacctgtcc a |
| Member of b-zip family, induced by ER damage/stress, binds to the ERSE in association with NF-Y | 950-964 | (G960T) gagaggtggccaccggcggcgcccctgtgg gcaccgagg t*t*gccg tggccgtggccaagcggctgaagatcggcg |
| X-box-binding protein 1 | 1252-1266 | (C1263A) gccatcgacaaggagggctggctgcactcc ggcgacgtg gg*a*tac tacgacgacgatggccacttcttcgtggtg |
| H6 homeodomain HMX3/Nkx5.1 transcription factor | 1278-1290 | (C1281A) ctccggcgacgtgggctactacgacgacga tgg*a*ca*t*tt (C1284T) cttc gtggaccggctgaaggagctgatcaag |
| Ribonucleoprotein associated zinc finger protein MOK-2 (mouse) | 1302-1322 | (G1308A) cgacgatggccacttcttcgtggtggaccg gctgaa*a*ga gctgatcaagta caagggctaccaggtggccccgccga gct |
| Winged helix protein, involved in hair keratinization and thymus epithelium differentiation | 1385-1395 | (C1389T) Agtggctgctgctccagcacccatccatca agga*t*gccg gc gtgaccggcgtgcccgacgaggccgcggc |
| NF-kappaB (p50) | (1502-1516) | (G1560A) ccgagcaggagatcatcgactacatcgccg agcg*a*gtgt (C1512T) c*t*ccca ccaagcgcatccggggcggcgtcgtcttcg |
| Winged helix protein, involved in hair keratinization and thymus epithelium differentiation | 1531-1541 | (C1536A) gagcgggtgtccccccaccaagcgcatccgg ggcgg*a*gtc gt cttcgtggacgacatccccaagggcgccac |

TABLE 8

| Amino Acid | Codon | RoLWT # | RoLWT % | RoLm # | RoLm % |
|---|---|---|---|---|---|
| Met | ATG | 10 | 1.84 | 10 | 1.84 |
| Trp | TGG | 2 | 0.37 | 2 | 0.37 |
| Glu | GAA | 31 | 5.7 | 1 | 0.18 |
|  | GAG | 5 | 0.92 | 35 | 6.43 |
| Phe | TTT | 11 | 2.02 | 0 | 0 |
|  | TTC | 13 | 2.39 | 24 | 4.41 |
| Asp | GAT | 15 | 2.76 | 3 | 0.55 |
|  | GAC | 12 | 2.21 | 24 | 4.41 |
| Cys | TGT | 5 | 0.92 | 1 | 0.18 |
|  | TGC | 5 | 0.92 | 9 | 1.65 |
| His | CAT | 8 | 1.47 | 1 | 0.18 |
|  | CAC | 2 | 0.37 | 9 | 1.65 |
| Gln | CAA | 9 | 1.65 | 0 | 0 |
|  | CAG | 4 | 0.74 | 13 | 2.39 |
| Asn | AAT | 11 | 2.02 | 1 | 0.18 |
|  | AAC | 7 | 1.29 | 17 | 3.12 |
| Tyr | TAT | 11 | 2.02 | 0 | 0 |
|  | TAC | 8 | 1.47 | 19 | 3.49 |
| Lys | AAA | 28 | 5.15 | 1 | 0.18 |
|  | AAG | 12 | 2.21 | 39 | 7.17 |

TABLE 8-continued

| Amino Acid | Codon | RoLWT # | RoLWT % | RoLm # | RoLm % |
|---|---|---|---|---|---|
| Ile | ATT | 19 | 3.49 | 2 | 0.37 |
|  | ATC | 10 | 1.84 | 34 | 6.25 |
|  | ATA | 7 | 1.29 | 0 | 0 |
| *** | TAA | 1 | 0.18 | 1 | 0.18 |
|  | TAG | 0 | 0 | 0 | 0 |
|  | TGA | 0 | 0 | 0 | 0 |
| Thr | ACT | 9 | 1.65 | 0 | 0 |
|  | ACC | 13 | 2.39 | 30 | 5.51 |
|  | ACA | 5 | 0.92 | 2 | 0.37 |
|  | ACG | 5 | 0.92 | 0 | 0 |
| Pro | CCT | 6 | 1.1 | 4 | 0.74 |
|  | CCC | 8 | 1.47 | 16 | 2.94 |
|  | CCA | 7 | 1.29 | 4 | 0.74 |
|  | CCG | 4 | 0.74 | 0 | 0 |
| Ala | GCT | 14 | 2.57 | 4 | 0.74 |
|  | GCC | 10 | 1.84 | 35 | 6.43 |
|  | GCA | 8 | 1.47 | 0 | 0 |
|  | GCG | 6 | 1.1 | 0 | 0 |
| Gly | GGT | 6 | 1.1 | 0 | 0 |
|  | GGC | 7 | 1.29 | 34 | 6.25 |
|  | GGA | 18 | 3.31 | 5 | 0.92 |
|  | GGG | 8 | 1.47 | 0 | 0 |
| Val | GTT | 14 | 2.57 | 1 | 0.18 |
|  | GTC | 10 | 1.84 | 3 | 0.55 |
|  | GTA | 17 | 3.12 | 1 | 0.18 |
|  | GTG | 6 | 1.1 | 42 | 7.72 |
| Arg | AGA | 8 | 1.47 | 9 | 1.65 |
|  | AGG | 4 | 0.74 | 7 | 1.29 |
|  | CGT | 3 | 0.55 | 0 | 0 |
|  | CGC | 4 | 0.74 | 3 | 0.55 |
|  | CGA | 5 | 0.92 | 1 | 0.18 |
|  | CGG | 2 | 0.37 | 6 | 1.1 |
| Ser | AGT | 6 | 1.1 | 0 | 0 |
|  | AGC | 8 | 1.47 | 14 | 2.57 |
|  | TCT | 7 | 1.29 | 3 | 0.55 |
|  | TCC | 3 | 0.55 | 17 | 3.12 |
|  | TCA | 3 | 0.55 | 0 | 0 |
|  | TCG | 7 | 1.29 | 0 | 0 |
| Leu | TTA | 19 | 3.49 | 0 | 0 |
|  | TTG | 16 | 2.94 | 0 | 0 |
|  | CTT | 12 | 2.21 | 1 | 0.18 |
|  | CTC | 1 | 0.18 | 4 | 0.74 |
|  | CTA | 3 | 0.55 | 0 | 0 |
|  | CTG | 6 | 1.1 | 52 | 9.56 |

TABLE 9

| Restriction enzyme site | | RoLWT | ROLm |
|---|---|---|---|
| 35 | AvaI | CTCGAG | CCAGGG |
| 35 | XhoI | CTCGAG | CCAGGG |
| 59 | PstI | CTGCAG | CCGCCG |
| 65 | ApoI | GAATTC | GCATTC |
| 65 | EcoRI | GAATTC | GCATTC |
| 70 | MunI | CAATTG | CAGCTC |
| 90 | ApoI | GAATTT | CAACTT |

TABLE 9-continued

| Restriction enzyme site | | RoLWT | ROLm |
|---|---|---|---|
| 438 | ScaI | AGTACT | GGTGCT |
| 528 | ApoI | AAATTT | AAACTT |
| 532 | DraI | TTTAAA | TTCAAG |
| 618 | HincII | GTTAAC | GCTGAC |
| 618 | HpaI | GTTAAC | GCTGAC |
| 630 | ApoI | AAATTT | GAACCT |
| 660 | BamHI | GGATCC | GGACCC |
| 744 | Psp1406I | AACGTT | AACCCT |
| 793 | BspT104I | TTCGAA | TTCGAG |
| 810 | AflII | CTTAAG | CCTGAG |
| 833 | ApoI | GAATTC | GAATCC |
| 833 | EcoRI | GAATTC | GAATCC |
| 931 | AgeI | ACCGGT | ACCGGC |
| 1038 | PshBI | ATTAAT | GCTGAT |
| 1050 | BspHI | TCATGA | CCACGA |
| 1113 | BglII | AGATCT | GGACCT |
| 1165 | DraI | TTTAAA | TTCAAG |
| 1225 | ClaI | ATCGAT | ATCGAC |
| 1273 | PshAI | GACGATGGTC | GACGATGGAC |
| 1296 | PvuI | CGATCG | GGACCG |
| 1302 | DraI | TTTAAA | GCTGAA |
| 1328 | EcoRV | GATATC | GCTACC |
| 1523 | Bst1107I | GTATAC | GCATCC |

EXAMPLE 14

Vectors in which the wild-type or mutant luciferase gene (orange- or green-emitting from *Rhagophthalmus ohba*) was inserted downstream of three kinds of the promoters SV40 were made (wild-type: SV40-RoL (Green) and SV40-RoL (orange), mutant: SV40-RoL (Green)m and SV40-RoL (Orange)m). The cultured fibroblast cells, NIH3T3 cells were transfected with each gene using Lipofectamine Plus, and the luminescence activity in the cells after 24 hours was measured. A luminescent substrate mixed solution (supplied from Toyo B-Net Co., Ltd.) and LB9506 supplied from Berthold were used as a substrate and as a luminescence determining apparatus, respectively. A sample was made by adding 50 μL of PicaGene to 50 μL of a cell extract solution. As a result, the samples containing the wild type SV40-RoL (Green) and SV40-RoL (orange) exhibited values of about $1 \times 10^6$ and $4 \times 10^5$ RLU, respectively whereas the samples containing mutant SV40-RoL (Green)m and SV40-RoL (Orange)m exhibited values of $5 \times 10^8$ and $8 \times 10^7$ RLU, respectively. Comparing the wild type with the mutant, when the value of the wild-type is made 1, the activity values were increased by about 44 times and about 57 times in the mutant green and orange luciferases, respectively. These results demonstrate that the mutant is useful as the reporter gene for the analysis of the mammalian gene expression.

EXAMPLE 15

An outline of a method for simultaneously determining the transcription activities of three genes in the mammalian cells using one substrate is shown in FIG. 19. Three gene vectors in which the promoter sequence has been inserted upstream of the red-emitting luciferase gene from the rail road worm, the green-emitting luciferase gene from *Rhagophthalmus ohba* and the orange-emitting luciferase gene from *Rhagophthalmus ohba* are co-expressed in the cultured cells. The co-expressing cells after a certain time course after the treatment of the cells are lysed. Subsequently, three transcription activities are measured by separating the luminescence activities of red-emitting luciferase from the rail road worm, the green-emitting luciferase from *Rhagophthalmus ohba* and the orange-emitting luciferase from *Rhagophthalmus ohba* in the cell extract solution using the color filters. Thus, 15 μL of PicaGene was added to 15 μL of the extract solution of the cells in which the red-emitting luciferase gene from the rail road worm, the green-emitting luciferase gene from *Rhagophthalmus ohba* and the orange-emitting luciferase gene from *Rhagophthalmus ohba* were independently expressed. Then the luminescence spectra were measured using the weak luminescence spectrum determining apparatus supplied from ATTO Corporation (FIG. 20). As a result of examining the luminescence spectra, it has been confirmed that color split is possible by selecting the color filter O-54 type supplied from Hoya Co., Ltd. for splitting the green and orange lights and selecting the color filter R-60 type supplied from Hoya Co., Ltd. for splitting the orange and red lights. The measuring procedure is as follows. (1) The emitted light intensity is measured without use of the filter (luminescence activities of the red, orange and green-emitting luciferases). (2) The color filter O-54 type is inserted in a luminometer and the emitted light intensity is measured to yield the luminescent activity of the green-emitting luciferase. (3) The color filter R-60 type is inserted in the luminometer and the emitted light intensity is measured to yield the luminescent activity of the green and orange luminescence activity. (4) The luminescence activity of the red is calculated by converting the transmittance of the filters. Further, the activities of three color luciferases are corrected. This way, it is possible to evaluate the emitted lights intensities and the abundance of the red-, green- and orange-emitting luciferases.

EXAMPLE 16

Figure 21:
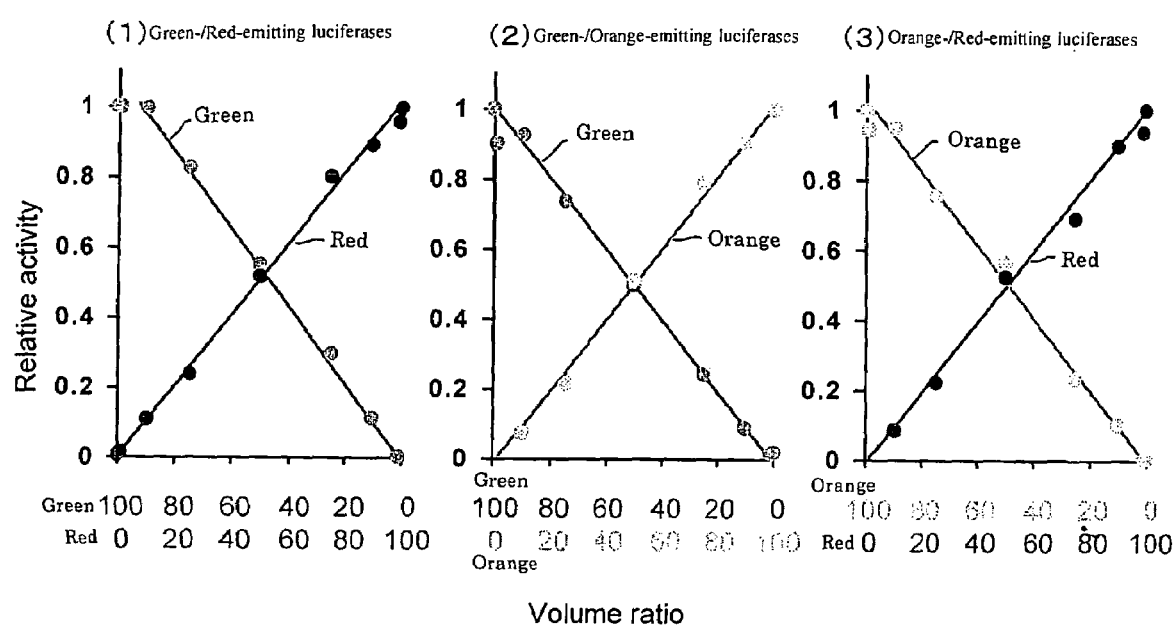
FIG. 21 shows abundance ratio and luminescence activity (when using the filter shown in FIG. 22) of two color luciferases (combinations of (A) green-red-emitting, (B) green-orange-emitting and (C) orange-red-emitting luciferases).

It has been examined in the model experiment whether two enzymes with different compositions in the red-, orange- and green-emitting luciferases whose abundance ratios are different can be quantified by the procedure determined in Example 15. In FIG. 21 for the red- and green-emitting luciferases (A), the green- and orange-emitting luciferases (B), and the orange- and red-emitting luciferases (C), the luminescence activities in samples with different abundance ratios were obtained by (1) measuring all emitted light intensities, (2) using the set filter and converting. As a result, it has been demonstrated that the luminescence activity is changed in a linear relationship with the abundance ratio. This suggests that the different amounts of the red-, orange- and green-emitting luciferases expressed in the mammalian cells can be quantified by the luminometer in which the filter has been inserted.

EXAMPLE 17

Figure 22:
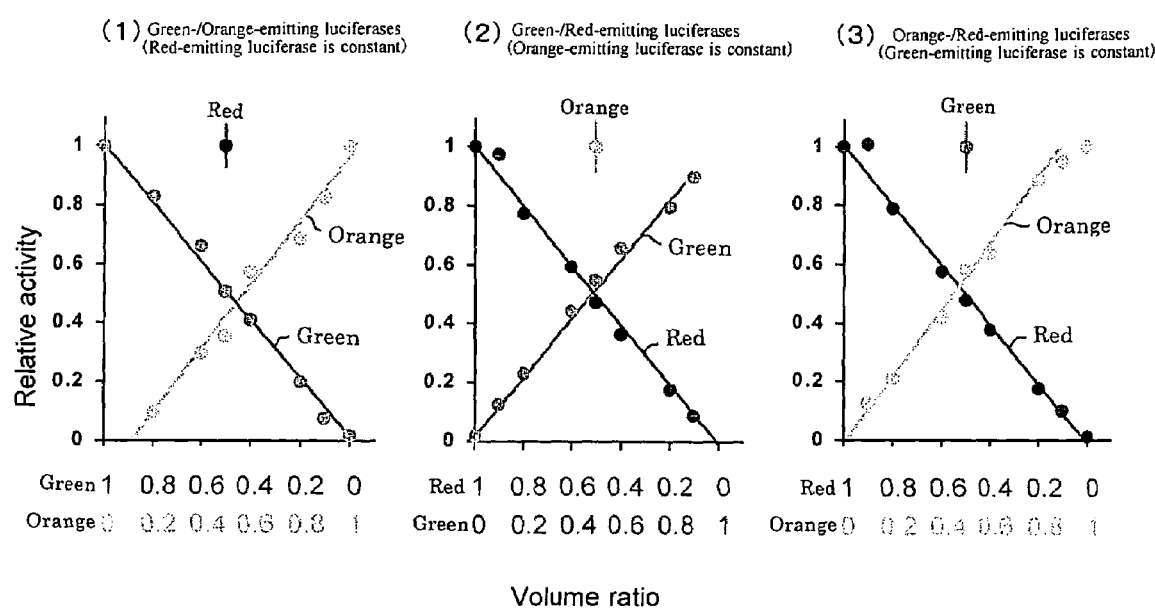
FIG. 22 shows an abundance ratio and luminescence activity (when using the filter shown in FIG. 20) of three color luciferases ((A) green-orange-emitting luciferases when a red-emitting luciferase is 1; (B) green-red-emitting luciferases when an orange-emitting luciferase is 1; and (C) orange-red-emitting luciferases when a green-emitting luciferase is 1).

It has been examined in the model experiment whether two enzymes with different compositions can be quantified by making the amount of one light-emitting enzyme constant in the red-, orange- and green-emitting luciferases whose abundance ratios are different by the procedure determined in Example 15. In FIG. 22, for the orange- and green-emitting luciferases by making the red-emitting luciferase constant (A), for the green- and red-emitting luciferases by making the orange-emitting luciferase constant (B), and for the orange- and red-emitting luciferases by making the green-emitting luciferase constant (C), the luminescence activities in samples with different abundance ratios were obtained by (1) measuring all emitted light intensities, (2) using the set filter and converting. As a result, it has been demonstrated that the luminescence activity is changed in a linear relationship with the abundance ratio. This suggests that the different amounts of the red-, orange- and green-emitting luciferases expressed in the mammalian cells can be quantified by the luminometer in which the filter has been inserted. Therefore, it has been demonstrated that it is possible to quantify the three luciferases by one substrate, and that the amounts of transcription activities of three genes can be measured.

The invention claimed is:

1. A gene construct comprising at least one luciferase gene selected from the group consisting of SEQ ID NOS: 7, 10 and 11.

2. The gene construct according to claim 1 comprising three luciferase genes stably expressible in mammalian cells wherein said three luciferase genes are SEQ ID NOS: 7, 10 and 11.

3. An expression vector containing the gene construct according to claim 1.

4. Isolated mammalian cells comprising two or more stably expressing genes of luciferases wherein said genes are selected from the group consisting of SEQ ID NOS: 7, 10 and 11.

5. The Isolated mammalian cells according to claim 4 comprising three luciferase genes under the control of different promoters wherein said three luciferase genes are SEQ ID NOS: 7, 10 and 11.

6. The Isolated mammalian cells according to claim 4 comprising two luciferase genes under the control of different promoters, wherein a first luciferase gene is under the control of a constantly expressed promoter, and a second luciferase gene is under the control of a pseudopromoter.

* * * * *

SEQUENCE LISTING

```
<160> NUMBER OF SEQ ID NOS: 65

<210> SEQ ID NO 1
<211> LENGTH: 1638
<212> TYPE: DNA
<213> ORGANISM: Wild Type Phrixothrix Green Luciferase

<400> SEQUENCE: 1
atggaagaag aaaacattag gcatggagag cgtcctcgtg atatagtcca tcctggctcg       60
gcaggacaac aattatacca atcattgtat aaatttgcat cttttcctga agcaataatc      120
gatgctcata caaatgaagt aatatcatat gctcaaatat ttgaaaccag ctgccgctta      180
gctgttagta tagaacaata tggcttgaat gaaaacaatg ttgtgggtgt atgcagtgaa      240
aacaatataa acttttttaa tcctgtcctt gctgctttat acttaggaat accagtagca      300
```

```
acatcaaatg atatgtacac agatggagag ttaactggtc atttgaatat atcaaaacca      360
actatcatgt ttagttcaaa gaaagcactc ccgcttattc tgagagtaca gcaaaatcta      420
agtttcatta aaaagtcgt agttatcgat agcatgtacg acattaatgg cgttgaatgc       480
gtatctacct ttgttgcacg ttatactgac cacacctttg atccattgtc atttacacca      540
aaagattttg atccccttga aaaaatcgca ttaattatgt catcatctgg aacaactgga      600
ttgcctaagg gtgtagtact gagccataga agtctaacta aagattcgt tcatagcagg       660
gatcccattt atggcactcg tacggttcca caaacatcaa ttctttcctt agtaccgttc      720
catcatgcct ttggaatgtt tactacatta tcttactttg tagtaggact taaggttgta      780
atgttgaaga aatttgaggg cgcacttttc ttaaaaacca tacagaatta caaaatcccc      840
actattgtag tggcccctcc agttatggtg ttttggcta aaagcccatt agtcgatcaa       900
tacgatttat cgagcttaac ggaagttgct actggaggag ctcctttagg aaaagatgtc      960
gcagaagcag tagcaaagag gttgaaatta cctggaatca tacaaggata tggattaact     1020
gaaacttgct gcgctgtaat gattacccct cataatgctg tgaaaacagg ttcaactgga     1080
agacccttgc catacattaa agctaaagtt ttagataacg ctactgggaa ggcgctagga     1140
ccaggagaaa gaggcgaaat atgctttaaa agtgaaatga ttatgaaagg atattacaac     1200
aatccggaag caactattga tactattgac aaagatggtt ggcttcattc tggagatatt     1260
ggatattacg acgaagatgg aaatttcttt atagttgatc gattgaaaga acttattaaa     1320
tacaagggat atcaggttgc gcctgctgaa ctggaaaatc tgcttttaca acatccaagt     1380
attgctgatg cgggtgttac tggagttccg gacgaatttg ctggacaatt acctgctgct     1440
tgtgttgtgt tagaatctgg caagacgctg actgaaaagg aagttcaaga ttttattgca     1500
gcacaagtca ctccaacaaa gcatcttcga ggcggtgtcg tatttgtaga cagtattccg     1560
aaaggcccta ctggaaaact catcagaaag gagctccgag aaatatttgc ccagcgagca     1620
ccaaaatcaa aattataa                                                   1638
```

<210> SEQ ID NO 2
<211> LENGTH: 545
<212> TYPE: PRT
<213> ORGANISM: Wild Type Phrixothrix Green Luciferase
<400> SEQUENCE: 2

```
Met Glu Glu Asn Ile Arg His Gly Glu Arg Pro Arg Asp Ile Val
1               5                   10                  15

His Pro Gly Ser Ala Gly Gln Gln Leu Tyr Gln Ser Leu Tyr Lys Phe
            20                  25                  30

Ala Ser Phe Pro Glu Ala Ile Ile Asp Ala His Thr Asn Glu Val Ile
        35                  40                  45

Ser Tyr Ala Gln Ile Phe Glu Thr Ser Cys Arg Leu Ala Val Ser Ile
    50                  55                  60

Glu Gln Tyr Gly Leu Asn Glu Asn Val Val Gly Val Cys Ser Glu
65                  70                  75                  80

Asn Asn Ile Asn Phe Phe Asn Pro Val Leu Ala Ala Leu Tyr Leu Gly
                85                  90                  95

Ile Pro Val Ala Thr Ser Asn Asp Met Tyr Thr Asp Gly Glu Leu Thr
            100                 105                 110

Gly His Leu Asn Ile Ser Lys Pro Thr Ile Met Phe Ser Ser Lys Lys
        115                 120                 125
```

-continued

```
Ala Leu Pro Leu Ile Leu Arg Val Gln Gln Asn Leu Ser Phe Ile Lys
        130                 135                 140

Lys Val Val Val Ile Asp Ser Met Tyr Asp Ile Asn Gly Val Glu Cys
145                 150                 155                 160

Val Ser Thr Phe Val Ala Arg Tyr Thr Asp His Thr Phe Asp Pro Leu
                165                 170                 175

Ser Phe Thr Pro Lys Asp Phe Asp Pro Leu Glu Lys Ile Ala Leu Ile
                180                 185                 190

Met Ser Ser Ser Gly Thr Thr Gly Leu Pro Lys Gly Val Val Leu Ser
                195                 200                 205

His Arg Ser Leu Thr Ile Arg Phe Val His Ser Arg Asp Pro Ile Tyr
        210                 215                 220

Gly Thr Arg Thr Val Pro Gln Thr Ser Ile Leu Ser Leu Val Pro Phe
225                 230                 235                 240

His His Ala Phe Gly Met Phe Thr Thr Leu Ser Tyr Phe Val Gly
                245                 250                 255

Leu Lys Val Val Met Leu Lys Lys Phe Glu Gly Ala Leu Phe Leu Lys
                260                 265                 270

Thr Ile Gln Asn Tyr Lys Ile Pro Thr Ile Val Val Ala Pro Pro Val
        275                 280                 285

Met Val Phe Leu Ala Lys Ser Pro Leu Val Asp Gln Tyr Asp Leu Ser
290                 295                 300

Ser Leu Thr Glu Val Ala Thr Gly Gly Ala Pro Leu Gly Lys Asp Val
305                 310                 315                 320

Ala Glu Ala Val Ala Lys Arg Leu Lys Leu Pro Gly Ile Ile Gln Gly
                325                 330                 335

Tyr Gly Leu Thr Glu Thr Cys Cys Ala Val Met Ile Thr Pro His Asn
                340                 345                 350

Ala Val Lys Thr Gly Ser Thr Gly Arg Pro Leu Pro Tyr Ile Lys Ala
                355                 360                 365

Lys Val Leu Asp Asn Ala Thr Gly Lys Ala Leu Gly Pro Gly Glu Arg
        370                 375                 380

Gly Glu Ile Cys Phe Lys Ser Glu Met Ile Met Lys Gly Tyr Tyr Asn
385                 390                 395                 400

Asn Pro Glu Ala Thr Ile Asp Thr Ile Asp Lys Asp Gly Trp Leu His
                405                 410                 415

Ser Gly Asp Ile Gly Tyr Tyr Asp Glu Asp Gly Asn Phe Phe Ile Val
                420                 425                 430

Asp Arg Leu Lys Glu Leu Ile Lys Tyr Lys Gly Tyr Gln Val Ala Pro
        435                 440                 445

Ala Glu Leu Glu Asn Leu Leu Gln His Pro Ser Ile Ala Asp Ala
        450                 455                 460

Gly Val Thr Gly Val Pro Asp Glu Phe Ala Gly Gln Leu Pro Ala Ala
465                 470                 475                 480

Cys Val Val Leu Glu Ser Gly Lys Thr Leu Thr Lys Glu Val Gln
                485                 490                 495

Asp Phe Ile Ala Ala Gln Val Thr Pro Thr Lys His Leu Arg Gly Gly
                500                 505                 510

Val Val Phe Val Asp Ser Ile Pro Lys Gly Pro Thr Gly Lys Leu Ile
                515                 520                 525
```

-continued

Arg Lys Glu Leu Arg Glu Ile Phe Ala Gln Arg Ala Pro Lys Ser Lys
    530                 535                 540

Leu
545

<210> SEQ ID NO 3
<211> LENGTH: 1641
<212> TYPE: DNA
<213> ORGANISM: Wild Type Phrixothrix Red Luciferase

<400> SEQUENCE: 3

| | | | | | | |
|---|---|---|---|---|---|---|
| atggaagaag | aaaacattgt | gaatggagat | cgtcctcgtg | atctagtttt | tcctggcaca | 60 |
| gcaggactac | aattatatca | atcattatat | aaatattcat | atattactga | cggaataatc | 120 |
| gatgcccata | ccaatgaagt | aatatcatat | gctcaaatat | ttgaaaccag | ctgccgcttg | 180 |
| gcagttagtc | tagaaaaata | tggcttggat | cataacaatg | ttgtggcaat | atgcagtgaa | 240 |
| aacaacatac | actttttttgg | cccttttaatt | gctgctttat | accaaggaat | accaatggca | 300 |
| acatcaaatg | atatgtacac | agaaagggag | atgattggcc | atttgaatat | atcgaaacca | 360 |
| tgccttatgt | tttgttcaaa | gaatcactc | ccatttattc | tgaaagtaca | aaaacatcta | 420 |
| gatttcctta | aaaagtcat | agtcattgat | agtatgtacg | atatcaatgg | cgttgaatgc | 480 |
| gtatttagct | ttgtttcacg | ttatactgat | cacgcctttg | atccagtgaa | atttaaccca | 540 |
| aaagagtttg | atcccttgga | agaaccgca | ttaattatga | catcatctgg | aacaactgga | 600 |
| ttgcctaaag | gggtagtaat | aagccataga | agtataacta | aagattcgt | ccatagcagt | 660 |
| gatcccatct | atggtactcg | tattgctcca | gatacatcaa | ttcttgctat | agcaccgttc | 720 |
| catcatgcct | ttggactgtt | tactgcacta | gcttactttc | cagtaggact | taagattgta | 780 |
| atggtgaaga | aatttgaggg | cgaattcttc | ttaaaaacca | tacaaaatta | caaaatcgct | 840 |
| tctattgtag | ttcctcctcc | aattatggta | tatttggcta | aaagtccatt | agtcgatgaa | 900 |
| tacaatttat | cgagcttaac | ggaaattgct | tgtggagggt | ctccttttagg | aagagatatc | 960 |
| gcagataaag | tagcaaagag | attgaaagta | catggaatcc | tacaaggata | tggattaacc | 1020 |
| gaaacctgca | gcgctctaat | acttagcccc | aatgatcgag | aacttaaaaa | aggtgcaatt | 1080 |
| ggaacgccta | tgccatatgt | tcaagttaaa | gttatagata | tcaatactgg | aaggcgcta | 1140 |
| ggaccaagag | aaaaaggcga | aatatgcttc | aaaagtcaaa | tgcttatgaa | aggatatcac | 1200 |
| aacaatccgc | aagcaactcg | tgatgctctt | gacaaagatg | gttggcttca | tactggggat | 1260 |
| cttggatatt | acgacgaaga | cagatttatc | tatgtagttg | atcgattgaa | agaacttatt | 1320 |
| aaatataaag | gatatcaggt | tgcgcctgct | gaactggaaa | atctgctttt | acaacatcca | 1380 |
| aatatttctg | atgcgggtgt | tattggaatt | ccggacgaat | ttgctggtca | attccttcc | 1440 |
| gcgtgtgttg | tgttagagcc | tggtaagaca | atgaccgaaa | aggaagttca | ggattatatt | 1500 |
| gcagagctag | tcactacaac | taaacatctt | cgaggcggtg | tcgtattttat | agatagtatt | 1560 |
| ccaaaaggcc | aacaggaaa | actcatgaga | aacgaactcc | gtgcaatatt | tgcccgggaa | 1620 |
| caggcaaaat | caaaattata | a | | | | 1641 |

<210> SEQ ID NO 4
<211> LENGTH: 546
<212> TYPE: PRT
<213> ORGANISM: Wild Type Phrixothrix Red Luciferase

<400> SEQUENCE: 4

```
Met Glu Glu Glu Asn Ile Val Asn Gly Asp Arg Pro Arg Asp Leu Val
1               5                   10                  15

Phe Pro Gly Thr Ala Gly Leu Gln Leu Tyr Gln Ser Leu Tyr Lys Tyr
            20                  25                  30

Ser Tyr Ile Thr Asp Gly Ile Ile Asp Ala His Thr Asn Glu Val Ile
        35                  40                  45

Ser Tyr Ala Gln Ile Phe Glu Thr Ser Cys Arg Leu Ala Val Ser Leu
    50                  55                  60

Glu Lys Tyr Gly Leu Asp His Asn Asn Val Val Ala Ile Cys Ser Glu
65                  70                  75                  80

Asn Asn Ile His Phe Phe Gly Pro Leu Ile Ala Ala Leu Tyr Gln Gly
                85                  90                  95

Ile Pro Met Ala Thr Ser Asn Asp Met Tyr Thr Glu Arg Glu Met Ile
            100                 105                 110

Gly His Leu Asn Ile Ser Lys Pro Cys Leu Met Phe Cys Ser Lys Lys
        115                 120                 125

Ser Leu Pro Phe Ile Leu Lys Val Gln Lys His Leu Asp Phe Leu Lys
    130                 135                 140

Lys Val Ile Val Ile Asp Ser Met Tyr Asp Ile Asn Gly Val Glu Cys
145                 150                 155                 160

Val Phe Ser Phe Val Ser Arg Tyr Thr Asp His Ala Phe Asp Pro Val
                165                 170                 175

Lys Phe Asn Pro Lys Glu Phe Asp Pro Leu Glu Arg Thr Ala Leu Ile
            180                 185                 190

Met Thr Ser Ser Gly Thr Thr Gly Leu Pro Lys Gly Val Val Ile Ser
        195                 200                 205

His Arg Ser Ile Thr Ile Arg Phe Val His Ser Ser Asp Pro Ile Tyr
    210                 215                 220

Gly Thr Arg Ile Ala Pro Asp Thr Ser Ile Leu Ala Ile Ala Pro Phe
225                 230                 235                 240

His His Ala Phe Gly Leu Phe Thr Ala Leu Ala Tyr Phe Pro Val Gly
                245                 250                 255

Leu Lys Ile Val Met Val Lys Phe Glu Gly Glu Phe Phe Leu Lys
            260                 265                 270

Thr Ile Gln Asn Tyr Lys Ile Ala Ser Ile Val Val Pro Pro Pro Ile
        275                 280                 285

Met Val Tyr Leu Ala Lys Ser Pro Leu Val Asp Glu Tyr Asn Leu Ser
    290                 295                 300

Ser Leu Thr Glu Ile Ala Cys Gly Gly Ser Pro Leu Gly Arg Asp Ile
305                 310                 315                 320

Ala Asp Lys Val Ala Lys Arg Leu Lys Val His Gly Ile Leu Gln Gly
                325                 330                 335

Tyr Gly Leu Thr Glu Thr Cys Ser Ala Leu Ile Leu Ser Pro Asn Asp
            340                 345                 350

Arg Glu Leu Lys Lys Gly Ala Ile Gly Thr Pro Met Pro Tyr Val Gln
        355                 360                 365

Val Lys Val Ile Asp Ile Asn Thr Gly Lys Ala Leu Gly Pro Arg Glu
    370                 375                 380

Lys Gly Glu Ile Cys Phe Lys Ser Gln Met Leu Met Lys Gly Tyr His
385                 390                 395                 400

Asn Asn Pro Gln Ala Thr Arg Asp Ala Leu Asp Lys Asp Gly Trp Leu
                405                 410                 415
```

```
His Thr Gly Asp Leu Gly Tyr Tyr Asp Glu Asp Arg Phe Ile Tyr Val
                420                 425                 430

Val Asp Arg Leu Lys Glu Leu Ile Lys Tyr Lys Gly Tyr Gln Val Ala
            435                 440                 445

Pro Ala Glu Leu Glu Asn Leu Leu Leu Gln His Pro Asn Ile Ser Asp
        450                 455                 460

Ala Gly Val Ile Gly Ile Pro Asp Glu Phe Ala Gly Gln Leu Pro Ser
465                 470                 475                 480

Ala Cys Val Val Leu Glu Pro Gly Lys Thr Met Thr Glu Lys Glu Val
                485                 490                 495

Gln Asp Tyr Ile Ala Glu Leu Val Thr Thr Lys His Leu Arg Gly
                500                 505                 510

Gly Val Val Phe Ile Asp Ser Ile Pro Lys Gly Pro Thr Gly Lys Leu
                515                 520                 525

Met Arg Asn Glu Leu Arg Ala Ile Phe Ala Arg Glu Gln Ala Lys Ser
            530                 535                 540

Lys Leu
545

<210> SEQ ID NO 5
<211> LENGTH: 1760
<212> TYPE: DNA
<213> ORGANISM: Phrixothrix Red Luciferase of US2002-0119542-A1

<400> SEQUENCE: 5
gtgacagttt agttcagtag aagatttttt tgagatcaaa atggaagaag aaaacgttgt      60
gaatggagat cgtcctcgtg atctagtttt tcctggcaca gcaggactac aattatatca    120
atcattatat aaatattcat atattactga cggaataatc gatgcccata ccaatgaagt    180
aatatcatat gctcaaatat ttgaaaccag ctgccgcttg cagttagtc tagaaaaata     240 tggcttggat cataacaatg ttgtggcaat atgcagtgaa acaacatac acttttttgg     300 cccctttaatt gctgctttat accaaggaat accaatggca acatcaaatg atatgtacac    360
agaaagggag atgattggcc atttgaatat atcgaaacca tgccttatgt tttgttcaaa    420
gaaatcactc ccatttattc tgaaagtaca aaaacatcta gatttcctta aagagtcat    480 agtcattgat agtatgtacg atatcaatgg cgttgaatgc gtatttagct ttgattcacg    540
taatactgat cacgcctttg atccagtgaa atttaaccca aaagagtttg atcccttgga    600
aagaaccgca ttaattatga catcatctgg aacaactgga ttgcctaaag gggtagtaat    660
aagccataga agtataacta agattcgt ccatagcagt gatcccatct atggtactcg      720
tattgctcca gatacatcaa ttcttgctat agcaccgttc catcatgcct ttggactgtt    780
tactgcacta gcttactttc agtaggact taagattgta atggtgaaga atttgaggg      840 cgaattcttc ttaaaaacca tacaaaatta caaaatcgct tctattgtag ttcctcctcc    900
aattatggta tatttggcta aaagtccatt agtcgatgaa tacaattgct cgagcttaac    960
ggaaattgct agtggaggct ctcctttagg aagagatatc gcagataaag tagcaaagag   1020
attgaaagta catggaatcc tacaaggata tggattaacc gaaacctgca gcgctctaat   1080
acttagcccc aatgatcgag aacttaaaaa aggtgcaatt ggaacgccta tgccatatgt   1140
tcaagttaaa gttatagata tcaatactgg gaaggcgcta ggaccaagag aaaaaggcga   1200
aatatgcttc aaagtcaaa tgcttatgaa aggatatcac aacaatccgc aagcaactcg     1260
tgatgctctt gacaaagatg gttggcttca tactggggat cttggatatt acgacgaaga   1320
```

-continued

| | |
|---|---|
| cagatttatc tatgtagttg atcgattgaa agaacttatt aaatataaag gatatcaggt | 1380 |
| tgcgcctgct gaactggaaa atctgctttt acaacatcca aatatttctg atgcgggtgt | 1440 |
| tattgaattc cggacgaatt tgctggtcaa ttacctttcc gcgtgtgttg tgttagagcc | 1500 |
| tggtaagaca atgaccgaaa aggaagttca ggattatatt gcagagctag tcactacaac | 1560 |
| taaacatctt cgaggcggtg tcgtatttat agatagtatt ccaaaaggcc aacaggaaa | 1620 |
| actcatgaga aacgaactcc gagcaatatt tgcccgggaa caggcaaaat caaaattata | 1680 |
| agctcaatat attgctttag ttataaaatg tatgtaatca aattttagaa cctaatacat | 1740 |
| tcattgagag cctaaaaaaa | 1760 |

<210> SEQ ID NO 6
<211> LENGTH: 1641
<212> TYPE: DNA
<213> ORGANISM: Phrixothrix Red Luciferase of WO2003/016839

<400> SEQUENCE: 6

| | |
|---|---|
| atggaagaag aaaacgtggt gaatggagat cggcctaggg atctggtgtt tcccggcaca | 60 |
| gcaggactcc agctgtacca gtcactgtat aagtattcat acatcactga cgggataatc | 120 |
| gacgcccata ccaacgaggt catctcatat gctcagatct ttgaaacctc ctgccggctg | 180 |
| gcagtgtcac tggagaagta tggcctggat cacaacaatg tggtggccat ctgttctgaa | 240 |
| aacaacatac actttttcgg ccccctgatt gctgccctgt accaaggcat cccaatggca | 300 |
| acatcaaacg acatgtacac agagagggag atgataggcc atctgaacat ctccaagcca | 360 |
| tgcctgatgt tctgttcaaa gaaatcactg cccttcattc tgaaggtgca gaagcacctg | 420 |
| gactttctga aaaagtcat agtcattgat tccatgtacg atatcaatgg cgtggagtgc | 480 |
| gtcttctcct ttgtctcgag gtacactgat cacgccttcg acccagtgaa gttcaacccc | 540 |
| aaagagttcg accccctcga agaaccgcc tgattatga catcatctgg gacaactgga | 600 |
| ctgcctaagg gggtcgtgat ctcccacaga tctataacta tcagattcgt ccattcttcc | 660 |
| gatcccatct acggcaccag gattgcccca gacacatcaa ttctggctat cgcacccttc | 720 |
| catcacgcct ttggactgtt tactgcactg gcttacttcc ctgtcggact gaagattgtc | 780 |
| atggtgaaga aatttgaggg cgagttcttt ctgaaaacca tacaaaatta caagatcgct | 840 |
| tctattgtcg tgcctcctcc tattatggtc tatctggcta agtccccct ggtcgatgaa | 900 |
| tacaatttat cttctctgac cgaaatcgca tgcggaggct ctcctctggg agagacatc | 960 |
| gcagataaag tcgccaagag actgaaagtg catggaatcc tccagggata tgggctgacc | 1020 |
| gagacctgtt ccgctctgat actgtctccc aacgatcggg aactgaaaaa ggggggcaatc | 1080 |
| ggaacccta tgccatacgt gcaagtgaaa gtgatcgaca tcaataccgg aaggccctg | 1140 |
| ggaccaagag agaaaggcga gatctgcttc aagtctcaga tgctgatgaa ggggtatcac | 1200 |
| aacaatcctc aggccactag ggatgctctg gacaaggatg gtggctgca cactggggac | 1260 |
| ctgggatatt acgacgaaga cagatttatc tatgtcgtgg acaggctgaa agagctgatc | 1320 |
| aagtataaag ggtatcaggt cgcccctgct gagttggaaa acctgctgtt gcagcacccc | 1380 |
| aatatctctg atgccggcgt gattggaatt ccggacgaat tgctggtca attaccttcc | 1440 |
| gcctgtgtgg tgctggagcc tggcaagaca atgaccgaga agaagtgca ggactacatt | 1500 |
| gcagagctgg tcactacaac taaacatctg agggggggggg tcgtctttat agattccatt | 1560 |
| ccaaagggcc aacagggaa actgatgaga aacgaactga gggcaatctt tgctcgggaa | 1620 |
| caggcaaaaa tcgctgtgta a | 1641 |

<210> SEQ ID NO 7
<211> LENGTH: 1641
<212> TYPE: DNA
<213> ORGANISM: Mutant Phrixothrix Red Luciferase of the Invention

<400> SEQUENCE: 7

| | | | | | | |
|---|---|---|---|---|---|---|
| atggaagaag | agaacatcgt | gaatggcgat | cgccctcggg | atctggtgtt | ccctggcaca | 60 |
| gccggcctgc | agctgtatca | gtccctgtat | aaatactctt | acatcaccga | cggaatcatc | 120 |
| gacgcccaca | ccaacgaggt | gatctcctat | gcccagattt | cgaaacaag | ttgccgcctg | 180 |
| gccgtgagcc | tggagaagta | tggcctggat | acaacaacg | tggtggccat | ttgcagcgag | 240 |
| aacaacatcc | acttcttcgg | ccctctgatc | gctgccctat | accaggggat | tccaatggcc | 300 |
| acatccaacg | atatgtacac | cgagagggag | atgatcggcc | acctgaacat | ctccaagcca | 360 |
| tgtctgatgt | tctgttccaa | gaagtccctg | ccattcatcc | tgaaggtgca | gaagcacctg | 420 |
| gactttctca | gaaggtgat | cgtgatcgac | agcatgtacg | acatcaacgg | cgtggagtgc | 480 |
| gtgttcagtt | tcgtgtcccg | gtacaccgat | cacgcgttcg | atccagtgaa | gttcaaccct | 540 |
| aaagagtttg | atcccctgga | gagaaccgcg | ctgatcatga | catcctctgg | aacaaccggc | 600 |
| ctgcctaagg | gcgtggtgat | cagccacagg | agcatcacca | tcagattcgt | ccacagcagc | 660 |
| gatcccatct | acggcacccg | catcgcccca | gatacatcca | tcctggccat | cgccccttc | 720 |
| caccacgcct | tcggactgtt | taccgccctg | gcttactttc | agtgggcct | gaagatcgtg | 780 |
| atggtgaaaa | agtttgaggg | cgagttcttc | ctgaagacca | tccagaacta | caagatcgct | 840 |
| tctatcgtgg | tgcctcctcc | aatcatggtg | tatctggcca | gagccctct | ggtggatgag | 900 |
| tacaatctgt | ccagcctgac | agagatcgcc | tgtggcggct | cccctctggg | cagagacatc | 960 |
| gccgacaagg | tggccaagag | actgaaggtc | acggcatcc | tgcagggcta | tggcctgacc | 1020 |
| gagacctgta | gcgccctgat | cctgagccc | aacgatagag | agctgaagaa | gggcgccatc | 1080 |
| ggcacccta | tgccctatgt | ccaggtgaag | gtgattgaca | tcaacaccgg | caaagccctg | 1140 |
| ggaccaagag | agaagggcga | gatttgcttc | aagagccaga | tgctgatgaa | gggctaccac | 1200 |
| aacaacccac | aggccaccag | ggatgccctg | gacaaggacg | gtggctgca | caccggcgat | 1260 |
| ctgggctact | acgacgagga | cagattcatc | tatgtggtgg | atcggctgaa | agagctcatc | 1320 |
| aagtacaagg | ctaccaggt | ggcccctgcc | gagctggaga | cttgcttct | gcagcaccct | 1380 |
| aacatctctg | atgccggcgt | catcggcatc | ccagacgagt | ttgccggcca | gctgccttcc | 1440 |
| gcctgtgtcg | tgctggagcc | tggcaagacc | atgaccgaga | aggaggtgca | ggattatatc | 1500 |
| gccgagctgg | tgaccaccac | caagcacctg | cggggcggcg | tggtgttcat | cgacagcatt | 1560 |
| ccgaaaggcc | aacaggcaa | gctgatgaga | acgagctga | gggccatctt | tgcccgcgag | 1620 |
| caggccaagt | ccaagctgta | a | | | | 1641 |

<210> SEQ ID NO 8
<211> LENGTH: 1632
<212> TYPE: DNA
<213> ORGANISM: Wild Type Rhagophthalmus ohbai Green Luciferase

<400> SEQUENCE: 8

| | | | | | | |
|---|---|---|---|---|---|---|
| atgcctaatg | aaatcatttt | acatggggcc | aaacctcgag | acccgttaga | cctgggaact | 60 |
| gcaggaattc | aattgtatag | ggctttgacg | aatttttcct | ttttaaggga | agccttgatc | 120 |
| gacgctcaca | ccgaggaagt | agtatcttac | gcggacattt | tggaaaacag | ctgtcgatta | 180 |
| gcaaaatgct | acgaaaacta | tggattacgc | caaaacagcg | tcatatcggt | gtgcagcgaa | 240 |

```
aacagcacga tcttcttcta ccccgtaatt gccgctttgt atatgggagt cataacagca    300
accgtaaatg atagttatac cgaacgggaa ttattggaaa ccttaaatat atcaaaaccg    360
gaattagtgt tctgctcgaa gaaagccatt aaaaatatga tggcattgaa aaggaacgtc    420
aatttattta aaaaggtagt acttttggat agtaaggaag acatgggcga agcccagtgt    480
cttagcaact ttatggcacg ctattcgaaa cccaatttgg acgtaagaaa ttttaaacca    540
cgcgattttg atgctaaaga acaagtcgct ttgatcatgt cctcatcggg aacaaccggg    600
ctgcccaaag gggtcgtgtt aacccatcga aatttaagcg ttcgcttcgt acactgcaag    660
gatcccttat tcggcacaag aactattcca tcaacttcga ttttatctat cgttcccttc    720
catcatgcgt ttggaatgtt tacaacgttg tcttatttta tagtagggct tagagttgta    780
ttactgaaaa gattcgaaga gaagtttttc ttaagcacca ttgaaaagta cagaattcca    840
actatcgttc ttgcgccgcc cgtaatggta ttcctagcta agagccccctt agttgatcag    900 tacgatttgt ccagtattag agaagtcgct accggtggcg cacctgttgg aactgaagtg    960
gcagtggccg ttgcgaaacg gttgaaaatt ggcggaatcc ttcagggcta cggattgacc   1020
gaaacgtgtt gcgccgtatt aattacccct catgacgacg ttaaaacagg ttctaccggg   1080
agggtagctc cttacgtcca agcgaaaatt gtagatctta ccaccggaaa atctctgggg   1140
ccaaataaaa gaggagagct ttgttttaaa agtgagatca ttatgaaggg ctatttcaac   1200
aataaacaag ctacggaaga agccatcgat aaagaaggat ggttacattc tggagatgtt   1260
gggtattatg acgacgatgg tcatttcttc gtagtcgatc gtttaaagga acttatcaag   1320
tacaagggat atcaagtagc accggctgaa ctggagtggt tgcttttgca acatccatct   1380
attaaagatg ccggtgttac tggcgttccc gacgaagctg ctggagaact accaggtgct   1440
tgtatagttc tccaagaagg aaaaagtctt actgaacaag aaattattga ctatatagcc   1500
gaacgagttt cgccaactaa acgtatacgt ggtggagtgg tcttcgttga tgatattcct   1560 aaagggcga ctggaaaact ggtcagaagt gaattacgaa aacttcttgc tcagaagaaa   1620
tcgaaactat aa                                                       1632

<210> SEQ ID NO 9
<211> LENGTH: 1632
<212> TYPE: DNA
<213> ORGANISM: Wild Type Rhagophthalmus ohbai Orange Luciferase

<400> SEQUENCE: 9
atgcctaatg aaatcatttt acatggggcc aaacctcgag acccgttaga cctgggaact     60
gcaggaattc aattgtatag ggctttgacg aattttttcct ttttaaggga agccttgatc    120
gacgctcaca ccgaggaagt agtatcttac gcggacattt tggaaaacag ctgtcgatta    180
gcaaaatgct acgaaaacta tggattacgc caaaacagcg tcatatcggt gtgcagcgaa    240
aacagcacga tcttcttcta ccccgtaatt gccgctttgt atatgggagt cataacagca    300
accgtaaatg atagttatac cgaacgggaa ttattggaaa ccttaaatat atcaaaaccg    360
gaattagtgt tctgctcgaa gaaagccatt aaaaatatga tggcattgaa aaggaacgtc    420
aatttattta aaaaggtagt acttttggat agtaaggaag acatgggcga agcccagtgt    480
cttagcaact ttatggcacg ctattcgaaa cccaatttgg acgtaagaaa ttttaaacca    540
cgcgattttg atgctaaaga acaagtcgct ttgatcatgt cctcatcggg aacaaccggg    600
ctgcccaaag gggtcgtgtt aacccatcga aatttaagcg ttcgcttcgt acactgcaag    660
gatcccttat tcggcaatag aactattcca tcaacttcga ttttatctat cgttcccttc    720
```

-continued

```
catcatgcgt ttggaatgtt tacaacgttg tcttatttta tagtagggct tagagttgta      780
ttactgaaaa gattcgaaga gaagtttttc ttaagcacca ttgaaaagta cagaattcca      840
actatcgttc ttgcgccgcc cgtaatggta ttcctagcta agagccccctt agttgatcag     900 tacgatttgt ccagtattag agaagtcgct accggtggcg cacctgttgg aactgaagtg     960
gcagtggccg ttgcgaaacg gttgaaaatt ggcggaatcc ttcagggcta cggattgacc    1020
gaaacgtgtt gcgccgtatt aattacccct catgacgacg ttaaaacagg ttctaccggg    1080
agggtagctc cttacgtcca agcgaaaatt gtagatctta ccaccggaaa atctctgggg    1140
ccaaataaaa gaggagagct ttgttttaaa agtgagatca ttatgaaggg ctatttcaac    1200
aataaacaag ctacggaaga agccatcgat aaagaaggat ggttacattc tggagatgtt    1260
gggtattatg acgacgatgg tcatttcttc gtagtcgatc gtttaaagga acttatcaag    1320
tacaagggat atcaagtagc accggctgaa ctggagtggt tgcttttgca acatccatct    1380
attaaagatg ccggtgttac tggcgttccc gacgaagctg ctggagaact accaggtgct    1440
tgtatagttc tccaagaagg aaaaagtctt actgaacaag aaattattga ctatatagcc    1500
gaacgagttt cgccaactaa acgtatacgt ggtggagtgg tcttcgttga tgatattcct    1560
aaaggggcga ctggaaaact ggtcagaagt gaattacgaa aacttcttgc tcagaagaaa    1620
tcgaaactat aa                                                        1632

<210> SEQ ID NO 10
<211> LENGTH: 1632
<212> TYPE: DNA
<213> ORGANISM: Mutant Rhagophthalmus ohbai Green Luciferase of the
      Invention

<400> SEQUENCE: 10
atggctaacg agatcatcct gcacggcgcc aagcccaggg accccctgga cctgggcacc       60
gccggcattc agctctacag ggccctgacc aacttctcct tcctgaggga ggccctgatc      120
gacgcccaca ccgaggaggt ggtgtcttac gccgacatcc tggagaacag ctgtagactg      180
gctaagtgct acgagaacta cggcctgcgc cagaacagcg tgatctccgt gtgcagcgag      240
aatagcacca tcttcttcta ccccgtgatc gccgccctgt acatgggcgt gatcaccgcc      300
accgtgaacg cagctacac cgagcgggag ctgctggaga ccctgaacat ctccaagccc      360
gaactggtgt tctgctccaa gaaggccatc aagaacatga tggccctgaa gaggaacgtg      420
aacttcatca agaaggtggt gctgctggac agcaaggagg atatgggcga ggcccagtgc      480
ctgagcaact tcatggcccg gtactccgag cccaacctgg acgtgagaaa cttcaagcca      540
agggacttcg acgccaagga gcaggtggcc cttattatgt cctcctctgg caccaccggc      600
ctgccaaagg gcgtggtgct gacccacagg aacctgagcg tgcgcttcgt ccactgcaag      660 gacccctgt tcggcaccag aaccatcccc tccacctcca tcctgtccat cgtgcccttc      720
caccacgcct tcggaatgtt cacaaccctg tcctacttca tcgtgggcct gagagtggtg      780
ctgctgaaga gattcgagga gaagttcttc ctgagcacca tcgagaagta cagaatccca      840
acaatcgtgc tggcccctcc tgtgatggtg ttcctggcta agagccccct ggtggaccag      900
tacgacctgt ccagcatcag agaggtggcc accggcggcg ccctgtgggg caccgaggtt      960
gccgtggccg tggccaagcg gctgaagatc ggcggcatcc tccagggcta cggcctgacc    1020
gagacctgct gcgccgtgct gatcaccccc cacgacgacg tgaagaccgg ctccaccggc    1080
agggtagccc cctacgtgca ggctaagatc gtggacctga ccaccggcaa gtccctggga    1140
```

```
cctaacaaga gaggcgagct gtgcttcaag agcgagatca tcatgaaggg ctacttcaac   1200
aacaagcagg ccaccgagga ggccatcgac aaggagggct ggctgcactc cggcgacgtg   1260
ggatactacg acgacgatgg acatttcttc gtggtggacc ggctgaaaga gctgatcaag   1320
tacaagggct accaggtggc ccccgccgag ctggagtggc tgctgctcca gcacccatcc   1380
atcaaggatg ccggcgtgac cggcgtgccc gacgaggccg ccggcgagct gcccggcgcc   1440
tgcatcgtgc tccaggaggg caagagcctg accgagcagg agatcatcga ctacatcgcc   1500
gagcgagtgt ctcccaccaa gcgcatccgg ggcggagtcg tcttcgtgga cgacatcccc   1560
aagggcgcca ccggcaagct ggtgagaagc gagctgcgga agctgctggc ccagaagaag   1620
tccaagctgt aa                                                       1632
```

<210> SEQ ID NO 11
<211> LENGTH: 1632
<212> TYPE: DNA
<213> ORGANISM: Mutant Rhagophthalmus ohbai Orange Luciferase of the
      Invention

<400> SEQUENCE: 11

```
atggctaacg agatcatcct gcacggcgcc aagcccaggg acccctggg cctgggcacc      60 gccggcattc agctctacag ggccctgacc aacttctcct tcctgaggga ggccctgatc    120
gacgcccaca ccgaggaggt ggtgtcttac gccgacatcc tggagaacag ctgtagactg    180
gctaagtgct acgagaacta cggcctgcgc cagaacagcg tgatctccgt gtgcagcgag    240
aatagcacca tcttcttcta ccccgtgatc gccgccctgt acatgggcgt gatcaccgcc    300
accgtgaacg acagctacac cgagcgggag ctgctggaga ccctgaacat ctccaagccc    360
gaactggtgt tctgctccaa gaaggccatc aagaacatga tggccctgaa gaggaacgtg    420
aacttcatca gaaggtggt gctgctggac agcaaggagg atatgggcga ggcccagtgc    480
ctgagcaact tcatggcccg gtactccgag cccaacctgg acgtgagaaa cttcaagcca    540
agggacttcg acgccaagga gcaggtggcc cttattatgt cctcctctgg caccaccggc    600
ctgccaaagg gcgtggtgct gacccacagg aacctgagcg tgcgcttcgt ccactgcaag    660
gaccccctgt cggcaacag aaccatcccc tccacctcca tcctgtccat cgtgcccttc    720
caccacgcct tcggaatgtt cacaaccctg tcctacttca tcgtgggcct gagagtggtg    780
ctgctgaaga gattcgagga gaagttcttc ctgagcacca tcgagaagta cagaatccca    840
acaatcgtgc tggcccctcc tgtgatggtg ttcctggcta agagccccct ggtggaccag    900
tacgacctgt ccagcatcag agaggtggcc accggcggcg cccctgtggg caccgaggtt    960
gccgtggccg tggccaagcg gctgaagatc ggcggcatcc tccagggcta cggcctgacc   1020
gagacctgct gcgccgtgct gatcaccccc cacgacgacg tgaagaccgg ctccaccggc   1080
agggtagccc cctacgtgca ggctaagatc gtggacctga ccaccggcaa gtccctggga   1140
cctaacaaga gaggcgagct gtgcttcaag agcgagatca tcatgaaggg ctacttcaac   1200
aacaagcagg ccaccgagga ggccatcgac aaggagggct ggctgcactc cggcgacgtg   1260
ggatactacg acgacgatgg acatttcttc gtggtggacc ggctgaaaga gctgatcaag   1320
tacaagggct accaggtggc ccccgccgag ctggagtggc tgctgctcca gcacccatcc   1380
atcaaggatg ccggcgtgac cggcgtgccc gacgaggccg ccggcgagct gcccggcgcc   1440
tgcatcgtgc tccaggaggg caagagcctg accgagcagg agatcatcga ctacatcgcc   1500
gagcgagtgt ctcccaccaa gcgcatccgg ggcggagtcg tcttcgtgga cgacatcccc   1560
```

```
aagggcgcca ccggcaagct ggtgagaagc gagctgcgga agctgctggc ccagaagaag    1620
tccaagctgt aa                                                       1632
```

<210> SEQ ID NO 12
<211> LENGTH: 543
<212> TYPE: PRT
<213> ORGANISM: Wild Type Rhagophthalmus ohbai Green Luciferase

<400> SEQUENCE: 12

```
Met Pro Asn Glu Ile Ile Leu His Gly Ala Lys Pro Arg Asp Pro Leu
1               5                   10                  15

Asp Leu Gly Thr Ala Gly Ile Gln Leu Tyr Arg Ala Leu Thr Asn Phe
            20                  25                  30

Ser Phe Leu Arg Glu Ala Leu Ile Asp Ala His Thr Glu Glu Val Val
        35                  40                  45

Ser Tyr Ala Asp Ile Leu Glu Asn Ser Cys Arg Leu Ala Lys Cys Tyr
    50                  55                  60

Glu Asn Tyr Gly Leu Arg Gln Asn Ser Val Ile Ser Val Cys Ser Glu
65                  70                  75                  80

Asn Ser Thr Ile Phe Phe Tyr Pro Val Ile Ala Ala Leu Tyr Met Gly
                85                  90                  95

Val Ile Thr Ala Thr Val Asn Asp Ser Tyr Thr Glu Arg Glu Leu Leu
            100                 105                 110

Glu Thr Leu Asn Ile Ser Lys Pro Glu Leu Val Phe Cys Ser Lys Lys
        115                 120                 125

Ala Ile Lys Asn Met Met Ala Leu Lys Arg Asn Val Asn Phe Ile Lys
    130                 135                 140

Lys Val Leu Leu Asp Ser Lys Glu Asp Met Gly Glu Ala Gln Cys
145                 150                 155                 160

Leu Ser Asn Phe Met Ala Arg Tyr Ser Glu Pro Asn Leu Asp Val Arg
                165                 170                 175

Asn Phe Lys Pro Arg Asp Phe Asp Ala Lys Glu Gln Val Ala Leu Ile
            180                 185                 190

Met Ser Ser Ser Gly Thr Thr Gly Leu Pro Lys Gly Val Val Leu Thr
        195                 200                 205

His Arg Asn Leu Ser Val Arg Phe Val His Cys Lys Asp Pro Leu Phe
    210                 215                 220

Gly Thr Arg Thr Ile Pro Ser Thr Ser Ile Leu Ser Ile Val Pro Phe
225                 230                 235                 240

His His Ala Phe Gly Met Phe Thr Thr Leu Ser Tyr Phe Ile Val Gly
                245                 250                 255

Leu Arg Val Val Leu Leu Lys Arg Phe Glu Glu Lys Phe Phe Leu Ser
            260                 265                 270

Thr Ile Glu Lys Tyr Arg Ile Pro Thr Ile Val Leu Ala Pro Pro Val
        275                 280                 285

Met Val Phe Leu Ala Lys Ser Pro Leu Val Asp Gln Tyr Asp Leu Ser
    290                 295                 300

Ser Ile Arg Glu Val Ala Thr Gly Gly Ala Pro Val Gly Thr Glu Val
305                 310                 315                 320

Ala Val Ala Val Ala Lys Arg Leu Lys Ile Gly Gly Ile Leu Gln Gly
                325                 330                 335

Tyr Gly Leu Thr Glu Thr Cys Cys Ala Val Leu Ile Thr Pro His Asp
            340                 345                 350
```

```
Asp Val Lys Thr Gly Ser Thr Gly Arg Val Ala Pro Tyr Val Gln Ala
            355                 360                 365

Lys Ile Val Asp Leu Thr Thr Gly Lys Ser Leu Gly Pro Asn Lys Arg
        370                 375                 380

Gly Glu Leu Cys Phe Lys Ser Glu Ile Ile Met Lys Gly Tyr Phe Asn
385                 390                 395                 400

Asn Lys Gln Ala Thr Glu Glu Ala Ile Asp Lys Glu Gly Trp Leu His
                405                 410                 415

Ser Gly Asp Val Gly Tyr Tyr Asp Asp Gly His Phe Phe Val Val
            420                 425                 430

Asp Arg Leu Lys Glu Leu Ile Lys Tyr Lys Gly Tyr Gln Val Ala Pro
            435                 440                 445

Ala Glu Leu Glu Trp Leu Leu Leu Gln His Pro Ser Ile Lys Asp Ala
        450                 455                 460

Gly Val Thr Gly Val Pro Asp Glu Ala Ala Gly Glu Leu Pro Gly Ala
465                 470                 475                 480

Cys Ile Val Leu Gln Glu Gly Lys Ser Leu Thr Gln Glu Ile Ile
                485                 490                 495

Asp Tyr Ile Ala Glu Arg Val Ser Pro Thr Lys Arg Ile Arg Gly Gly
            500                 505                 510

Val Val Phe Val Asp Asp Ile Pro Lys Gly Ala Thr Gly Lys Leu Val
            515                 520                 525

Arg Ser Glu Leu Arg Lys Leu Leu Ala Gln Lys Lys Ser Lys Leu
        530                 535                 540

<210> SEQ ID NO 13
<211> LENGTH: 543
<212> TYPE: PRT
<213> ORGANISM: Wild Type Rhagophthalmus ohbai Orange Luciferase

<400> SEQUENCE: 13

Met Pro Asn Glu Ile Ile Leu His Gly Ala Lys Pro Arg Asp Pro Leu
1               5                   10                  15

Asp Leu Gly Thr Ala Gly Ile Gln Leu Tyr Arg Ala Leu Thr Asn Phe
            20                  25                  30

Ser Phe Leu Arg Glu Ala Leu Ile Asp Ala His Thr Glu Glu Val Val
        35                  40                  45

Ser Tyr Ala Asp Ile Leu Glu Asn Ser Cys Arg Leu Ala Lys Cys Tyr
    50                  55                  60

Glu Asn Tyr Gly Leu Arg Gln Asn Ser Val Ile Ser Val Cys Ser Glu
65                  70                  75                  80

Asn Ser Thr Ile Phe Phe Tyr Pro Val Ile Ala Ala Leu Tyr Met Gly
                85                  90                  95

Val Ile Thr Ala Thr Val Asn Asp Ser Tyr Thr Glu Arg Glu Leu Leu
            100                 105                 110

Glu Thr Leu Asn Ile Ser Lys Pro Glu Leu Val Phe Cys Ser Lys Lys
        115                 120                 125

Ala Ile Lys Asn Met Met Ala Leu Lys Arg Asn Val Asn Phe Ile Lys
    130                 135                 140

Lys Val Val Leu Leu Asp Ser Lys Glu Asp Met Gly Glu Ala Gln Cys
145                 150                 155                 160

Leu Ser Asn Phe Met Ala Arg Tyr Ser Glu Pro Asn Leu Asp Val Arg
                165                 170                 175

Asn Phe Lys Pro Arg Asp Phe Asp Ala Lys Glu Gln Val Ala Leu Ile
            180                 185                 190
```

```
Met Ser Ser Ser Gly Thr Thr Gly Leu Pro Lys Gly Val Val Leu Thr
        195                 200                 205

His Arg Asn Leu Ser Val Arg Phe Val His Cys Lys Asp Pro Leu Phe
    210                 215                 220

Gly Asn Arg Thr Ile Pro Ser Thr Ser Ile Leu Ser Ile Val Pro Phe
225                 230                 235                 240

His His Ala Phe Gly Met Phe Thr Thr Leu Ser Tyr Phe Ile Val Gly
                245                 250                 255

Leu Arg Val Val Leu Leu Lys Arg Phe Glu Lys Phe Phe Leu Ser
        260                 265                 270

Thr Ile Glu Lys Tyr Arg Ile Pro Thr Ile Val Leu Ala Pro Pro Val
    275                 280                 285

Met Val Phe Leu Ala Lys Ser Pro Leu Val Asp Gln Tyr Asp Leu Ser
    290                 295                 300

Ser Ile Arg Glu Val Ala Thr Gly Gly Ala Pro Val Gly Thr Glu Val
305                 310                 315                 320

Ala Val Ala Val Ala Lys Arg Leu Lys Ile Gly Gly Ile Leu Gln Gly
                325                 330                 335

Tyr Gly Leu Thr Glu Thr Cys Cys Ala Val Leu Ile Thr Pro His Asp
                340                 345                 350

Asp Val Lys Thr Gly Ser Thr Gly Arg Val Ala Pro Tyr Val Gln Ala
        355                 360                 365

Lys Ile Val Asp Leu Thr Thr Gly Lys Ser Leu Gly Pro Asn Lys Arg
    370                 375                 380

Gly Glu Leu Cys Phe Lys Ser Glu Ile Ile Met Lys Gly Tyr Phe Asn
385                 390                 395                 400

Asn Lys Gln Ala Thr Glu Glu Ala Ile Asp Lys Glu Gly Trp Leu His
                405                 410                 415

Ser Gly Asp Val Gly Tyr Tyr Asp Asp Asp Gly His Phe Phe Val Val
                420                 425                 430

Asp Arg Leu Lys Glu Leu Ile Lys Tyr Lys Gly Tyr Gln Val Ala Pro
        435                 440                 445

Ala Glu Leu Glu Trp Leu Leu Leu Gln His Pro Ser Ile Lys Asp Ala
        450                 455                 460

Gly Val Thr Gly Val Pro Asp Glu Ala Ala Gly Glu Leu Pro Gly Ala
465                 470                 475                 480

Cys Ile Val Leu Gln Glu Gly Lys Ser Leu Thr Glu Gln Glu Ile Ile
                485                 490                 495

Asp Tyr Ile Ala Glu Arg Val Ser Pro Thr Lys Arg Ile Arg Gly Gly
                500                 505                 510

Val Val Phe Val Asp Asp Ile Pro Lys Gly Ala Thr Gly Lys Leu Val
        515                 520                 525

Arg Ser Glu Leu Arg Lys Leu Leu Ala Gln Lys Lys Ser Lys Leu
530                 535                 540

<210> SEQ ID NO 14
<211> LENGTH: 543
<212> TYPE: PRT
<213> ORGANISM: Mutant Rhagophthalmus ohbai Green Luciferase of the
      Invention
```

<400> SEQUENCE: 14

```
Met Ala Asn Glu Ile Ile Leu His Gly Ala Lys Pro Arg Asp Pro Leu
1               5                   10                  15

Asp Leu Gly Thr Ala Gly Ile Gln Leu Tyr Arg Ala Leu Thr Asn Phe
            20                  25                  30

Ser Phe Leu Arg Glu Ala Leu Ile Asp Ala His Thr Glu Glu Val Val
        35                  40                  45

Ser Tyr Ala Asp Ile Leu Glu Asn Ser Cys Arg Leu Ala Lys Cys Tyr
    50                  55                  60

Glu Asn Tyr Gly Leu Arg Gln Asn Ser Val Ile Ser Val Cys Ser Glu
65                  70                  75                  80

Asn Ser Thr Ile Phe Phe Tyr Pro Val Ile Ala Ala Leu Tyr Met Gly
                85                  90                  95

Val Ile Thr Ala Thr Val Asn Asp Ser Tyr Thr Glu Arg Glu Leu Leu
            100                 105                 110

Glu Thr Leu Asn Ile Ser Lys Pro Glu Leu Val Phe Cys Ser Lys Lys
        115                 120                 125

Ala Ile Lys Asn Met Met Ala Leu Lys Arg Asn Val Asn Phe Ile Lys
    130                 135                 140

Lys Val Leu Leu Asp Ser Lys Glu Asp Met Gly Glu Ala Gln Cys
145                 150                 155                 160

Leu Ser Asn Phe Met Ala Arg Tyr Ser Glu Pro Asn Leu Asp Val Arg
                165                 170                 175

Asn Phe Lys Pro Arg Asp Phe Asp Ala Lys Glu Gln Val Ala Leu Ile
            180                 185                 190

Met Ser Ser Ser Gly Thr Thr Gly Leu Pro Lys Gly Val Val Leu Thr
        195                 200                 205

His Arg Asn Leu Ser Val Arg Phe Val His Cys Lys Asp Pro Leu Phe
    210                 215                 220

Gly Thr Arg Thr Ile Pro Ser Thr Ser Ile Leu Ser Ile Val Pro Phe
225                 230                 235                 240

His His Ala Phe Gly Met Phe Thr Thr Leu Ser Tyr Phe Ile Val Gly
                245                 250                 255

Leu Arg Val Val Leu Leu Lys Arg Phe Glu Glu Lys Phe Phe Leu Ser
            260                 265                 270

Thr Ile Glu Lys Tyr Arg Ile Pro Thr Ile Val Leu Ala Pro Pro Val
        275                 280                 285

Met Val Phe Leu Ala Lys Ser Pro Leu Val Asp Gln Tyr Asp Leu Ser
    290                 295                 300

Ser Ile Arg Glu Val Ala Thr Gly Gly Ala Pro Val Gly Thr Glu Val
305                 310                 315                 320

Ala Val Ala Val Ala Lys Arg Leu Lys Ile Gly Gly Ile Leu Gln Gly
                325                 330                 335

Tyr Gly Leu Thr Glu Thr Cys Cys Ala Val Leu Ile Thr Pro His Asp
            340                 345                 350

Asp Val Lys Thr Gly Ser Thr Gly Arg Val Ala Pro Tyr Val Gln Ala
        355                 360                 365

Lys Ile Val Asp Leu Thr Thr Gly Lys Ser Leu Gly Pro Asn Lys Arg
    370                 375                 380

Gly Glu Leu Cys Phe Lys Ser Glu Ile Ile Met Lys Gly Tyr Phe Asn
385                 390                 395                 400

Asn Lys Gln Ala Thr Glu Glu Ala Ile Asp Lys Glu Gly Trp Leu His
                405                 410                 415
```

```
Ser Gly Asp Val Gly Tyr Tyr Asp Asp Gly His Phe Phe Val Val
            420                 425                 430

Asp Arg Leu Lys Glu Leu Ile Lys Tyr Lys Gly Tyr Gln Val Ala Pro
        435                 440                 445

Ala Glu Leu Glu Trp Leu Leu Leu Gln His Pro Ser Ile Lys Asp Ala
    450                 455                 460

Gly Val Thr Gly Val Pro Asp Glu Ala Ala Gly Glu Leu Pro Gly Ala
465                 470                 475                 480

Cys Ile Val Leu Gln Glu Gly Lys Ser Leu Thr Gln Glu Ile Ile
            485                 490                 495

Asp Tyr Ile Ala Glu Arg Val Ser Pro Thr Lys Arg Ile Arg Gly Gly
            500                 505                 510

Val Val Phe Val Asp Asp Ile Pro Lys Gly Ala Thr Gly Lys Leu Val
            515                 520                 525

Arg Ser Glu Leu Arg Lys Leu Leu Ala Gln Lys Lys Ser Lys Leu
            530                 535                 540

<210> SEQ ID NO 15
<211> LENGTH: 543
<212> TYPE: PRT
<213> ORGANISM: Mutant Rhagophthalmus ohbai Orange Luciferase of the
      Invention

<400> SEQUENCE: 15

Met Ala Asn Glu Ile Ile Leu His Gly Ala Lys Pro Arg Asp Pro Leu
1               5                   10                  15

Asp Leu Gly Thr Ala Gly Ile Gln Leu Tyr Arg Ala Leu Thr Asn Phe
            20                  25                  30

Ser Phe Leu Arg Glu Ala Leu Ile Asp Ala His Thr Glu Glu Val Val
        35                  40                  45

Ser Tyr Ala Asp Ile Leu Glu Asn Ser Cys Arg Leu Ala Lys Cys Tyr
    50                  55                  60

Glu Asn Tyr Gly Leu Arg Gln Asn Ser Val Ile Ser Val Cys Ser Glu
65                  70                  75                  80

Asn Ser Thr Ile Phe Phe Tyr Pro Val Ile Ala Ala Leu Tyr Met Gly
            85                  90                  95

Val Ile Thr Ala Thr Val Asn Asp Ser Tyr Thr Glu Arg Glu Leu Leu
            100                 105                 110

Glu Thr Leu Asn Ile Ser Lys Pro Glu Leu Val Phe Cys Ser Lys Lys
        115                 120                 125

Ala Ile Lys Asn Met Met Ala Leu Lys Arg Asn Val Asn Phe Ile Lys
    130                 135                 140

Lys Val Val Leu Leu Asp Ser Lys Glu Asp Met Gly Glu Ala Gln Cys
145                 150                 155                 160

Leu Ser Asn Phe Met Ala Arg Tyr Ser Glu Pro Asn Leu Asp Val Arg
            165                 170                 175

Asn Phe Lys Pro Arg Asp Phe Asp Ala Lys Glu Gln Val Ala Leu Ile
            180                 185                 190

Met Ser Ser Ser Gly Thr Thr Gly Leu Pro Lys Gly Val Val Leu Thr
        195                 200                 205

His Arg Asn Leu Ser Val Arg Phe Val His Cys Lys Asp Pro Leu Phe
    210                 215                 220

Gly Asn Arg Thr Ile Pro Ser Thr Ser Ile Leu Ser Ile Val Pro Phe
225                 230                 235                 240
```

-continued

```
His His Ala Phe Gly Met Phe Thr Thr Leu Ser Tyr Phe Ile Val Gly
                245                 250                 255

Leu Arg Val Val Leu Leu Lys Arg Phe Glu Glu Lys Phe Phe Leu Ser
            260                 265                 270

Thr Ile Glu Lys Tyr Arg Ile Pro Thr Ile Val Leu Ala Pro Pro Val
        275                 280                 285

Met Val Phe Leu Ala Lys Ser Pro Leu Val Asp Gln Tyr Asp Leu Ser
    290                 295                 300

Ser Ile Arg Glu Val Ala Thr Gly Gly Ala Pro Val Gly Thr Glu Val
305                 310                 315                 320

Ala Val Ala Val Ala Lys Arg Leu Lys Ile Gly Ile Leu Gln Gly
                325                 330                 335

Tyr Gly Leu Thr Glu Thr Cys Cys Ala Val Leu Ile Thr Pro His Asp
            340                 345                 350

Asp Val Lys Thr Gly Ser Thr Gly Arg Val Ala Pro Tyr Val Gln Ala
        355                 360                 365

Lys Ile Val Asp Leu Thr Thr Gly Lys Ser Leu Gly Pro Asn Lys Arg
    370                 375                 380

Gly Glu Leu Cys Phe Lys Ser Glu Ile Ile Met Lys Gly Tyr Phe Asn
385                 390                 395                 400

Asn Lys Gln Ala Thr Glu Glu Ala Ile Asp Lys Glu Gly Trp Leu His
                405                 410                 415

Ser Gly Asp Val Gly Tyr Tyr Asp Asp Asp Gly His Phe Phe Val Val
            420                 425                 430

Asp Arg Leu Lys Glu Leu Ile Lys Tyr Lys Gly Tyr Gln Val Ala Pro
        435                 440                 445

Ala Glu Leu Glu Trp Leu Leu Leu Gln His Pro Ser Ile Lys Asp Ala
    450                 455                 460

Gly Val Thr Gly Val Pro Asp Glu Ala Ala Gly Glu Leu Pro Gly Ala
465                 470                 475                 480

Cys Ile Val Leu Gln Glu Gly Lys Ser Leu Thr Gln Glu Ile Ile
                485                 490                 495

Asp Tyr Ile Ala Glu Arg Val Ser Pro Thr Lys Arg Ile Arg Gly Gly
            500                 505                 510

Val Val Phe Val Asp Asp Ile Pro Lys Gly Ala Thr Gly Lys Leu Val
        515                 520                 525

Arg Ser Glu Leu Arg Lys Leu Leu Ala Gln Lys Lys Ser Lys Leu
    530                 535                 540
```

<210> SEQ ID NO 16
<211> LENGTH: 1638
<212> TYPE: DNA
<213> ORGANISM: Mutant Phrixothrix Green Luciferase

<400> SEQUENCE: 16

```
atggaagaag agaacatcag gcacggcgag cgccctcggg acatcgtcca ccctggctcc    60
gccggccagc agctgtacca gtccctgtac aagttcgcct ccttccctga ggccatcatc   120
gacgcccaca ccaacgaggt gatctcctac gcccagattt tcgaaaccag ctgccgcctg   180
gccgtgagca tcgagcagta cggcctgaac gagaacaacg tggtgggcgt ctgtagcgag   240
aacaacatca acttcttcaa ccctgtgctg gccgccctgt acctcggcat cccagtggcc   300
acctccaacg atatgtacac cgatggcgag ctgaccggcc acctgaacat ctccaagcca   360
accatcatgt tcagctccaa gaaggccctg cccctgatcc tgagagtgca gcagaacctg   420
```

-continued

```
agcttcatca agaaggtggt ggtgatcgac agcatgtacg acatcaacgg cgtggagtgc      480
gtgtctacct tcgttgcccg gtacaccgac cacaccttcg acccactgtc cttcacccca      540
aaggacttcg acccctgga gaagatcgcc ctgatcatgt catcctccgg caccaccggc      600
ctgcctaagg gcgtggtgct gagccacaga agcctgacca tcagattcgt ccacagcagg      660
gaccccatct acggcacccg caccgtgccc cagacctcca tcctgtccct ggtgccattt      720
caccacgcct tcggcatgtt caccaccctg tcctacttcg tggtgggcct gaaggtggtg      780
atgctgaaga agttcgaggg cgccctcttc ctgaagacca tccagaacta caagatccct      840
acaatcgtgg tggcccctcc agtgatggtg ttcctggcta agagcccact ggtggatcag      900
tacgatctgt ccagcctcac cgaggtggct accggcggcg ctcctctggg caaggatgtg      960
gccgaggctg tggccaagag attgaagctg cctggcatca tccagggcta cggcctgacc     1020
gagacctgct gcgctgtgat gatcacccct cacaacgctg tgaagaccgg ctccaccggc     1080 agaccctgc catacatcaa ggctaaggtg ctggataacg ctaccggcaa agccctggga     1140
ccaggcgaga gaggcgagat ttgcttcaag agcgagatga tcatgaaggg ctactacaac     1200
aaccctgagg ccaccatcga caccatcgac aaggatggct ggctgcactc tggcgacatc     1260
ggctactacg acgaggatgg caacttcttc atcgtggatc ggctgaaaga gctgatcaag     1320
tacaagggct accaggtggc ccctgctgag ctggagaact tgcttctgca gcacccaagc     1380
atcgctgatg ccggcgtgac cggcgtgccc gacgagttcg ctggccagct gcctgctgct     1440
tgtgtcgtgc tggagtctgg caagacattg accgagaagg aggtgcaaga tttcatcgcc     1500
gcccaggtga ccccaactaa gcacctgcgg ggcggcgtgg tgttcgtgga cagcatccct     1560
aaaggcccta ccggcaagct gatcagaaag gagctgcggg agattttcgc ccagagagcc     1620
ccaaagtcca agctgtaa                                                   1638
```

<210> SEQ ID NO 17  
<211> LENGTH: 75  
<212> TYPE: DNA  
<213> ORGANISM: Phrixothrix Red Luciferase

<400> SEQUENCE: 17

```
cagcaggact acaattatat caatcattat ataaatattc ttatattact gacggaataa      60
tcgatgccca tacca                                                        75
```

<210> SEQ ID NO 18  
<211> LENGTH: 71  
<212> TYPE: DNA  
<213> ORGANISM: Phrixothrix Red Luciferase

<400> SEQUENCE: 18

```
gcaggactac aattatatca atcattatat aaatactcgt atattactga cggaataatc      60
gatgcccata c                                                           71
```

<210> SEQ ID NO 19  
<211> LENGTH: 77  
<212> TYPE: DNA  
<213> ORGANISM: Phrixothrix Red Luciferase

<400> SEQUENCE: 19

```
caatgaagta atatcatatg ctcaaatatt tgaaacaagt tgccgcttgg cagttagtct      60
agaaaaatat ggcttgg                                                     77
```

<210> SEQ ID NO 20
<211> LENGTH: 75
<212> TYPE: DNA
<213> ORGANISM: Phrixothrix Red Luciferase

<400> SEQUENCE: 20
aatatttgaa accagctgcc gcttggcagt tagtctagag aaatatggct tggatcataa    60
caatgttgtg gcaat                                                    75

<210> SEQ ID NO 21
<211> LENGTH: 77
<212> TYPE: DNA
<213> ORGANISM: Phrixothrix Red Luciferase

<400> SEQUENCE: 21
gaaaacaaca tacactttttt tggccctttta attgctgccc tataccaagg aataccaatg    60
gcaacatcaa atgatat                                                  77

<210> SEQ ID NO 22
<211> LENGTH: 73
<212> TYPE: DNA
<213> ORGANISM: Phrixothrix Red Luciferase

<400> SEQUENCE: 22
acttttttgg cccttttaatt gctgctttat accaagggat accaatggca acatcaaatg    60
atatgtacac aga                                                      73

<210> SEQ ID NO 23
<211> LENGTH: 71
<212> TYPE: DNA
<213> ORGANISM: Phrixothrix Red Luciferase

<400> SEQUENCE: 23
catcaaatga tatgtacaca gaaagggaga tgatcggcca tttgaatata tcgaaccat    60 gccttatgtt t                                                        71

<210> SEQ ID NO 24
<211> LENGTH: 77
<212> TYPE: DNA
<213> ORGANISM: Phrixothrix Red Luciferase

<400> SEQUENCE: 24
tttattctga agtacaaaa acatctagat tttctcaaaa aagtcatagt cattgatagt    60
atgtacgata tcaatgg                                                  77

<210> SEQ ID NO 25
<211> LENGTH: 77
<212> TYPE: DNA
<213> ORGANISM: Phrixothrix Red Luciferase

<400> SEQUENCE: 25
atgtacgata tcaatggcgt tgaatgcgta tttagttttg tttcacgtta tactgatcac    60
gcctttgatc cagtgaa                                                  77

<210> SEQ ID NO 26
<211> LENGTH: 75
<212> TYPE: DNA
<213> ORGANISM: Phrixothrix Red Luciferase

```
<400> SEQUENCE: 26
atatcaatgg cgttgaatgc gtatttagct ttgtttcacg gtatactgat cacgcctttg      60
atccagtgaa attta                                                      75

<210> SEQ ID NO 27
<211> LENGTH: 77
<212> TYPE: DNA
<213> ORGANISM: Phrixothrix Red Luciferase

<400> SEQUENCE: 27
gtatttagct ttgtttcacg ttatactgat cacgcgttcg atccagtgaa atttaaccca      60
aaagagtttg atccctt                                                    77

<210> SEQ ID NO 28
<211> LENGTH: 77
<212> TYPE: DNA
<213> ORGANISM: Phrixothrix Red Luciferase

<400> SEQUENCE: 28
tttaacccaa aagagtttga tcccttggaa agaaccgcgc taattatgac atcatctgga      60
acaactggat tgcctaa                                                    77

<210> SEQ ID NO 29
<211> LENGTH: 81
<212> TYPE: DNA
<213> ORGANISM: Phrixothrix Red Luciferase

<400> SEQUENCE: 29
gaaccgcatt aattatgaca tcatctggaa caactggcct gcctaaaggg gtagtaataa      60
gccatagaag tataactata a                                               81

<210> SEQ ID NO 30
<211> LENGTH: 73
<212> TYPE: DNA
<213> ORGANISM: Phrixothrix Red Luciferase

<400> SEQUENCE: 30
ctggattgcc taaaggggta gtaataagcc ataggagtat aactataaga ttcgtccata      60
gcagtgatcc cat                                                        73

<210> SEQ ID NO 31
<211> LENGTH: 77
<212> TYPE: DNA
<213> ORGANISM: Phrixothrix Red Luciferase

<400> SEQUENCE: 31
aagaaatttg agggcgaatt cttcttaaaa accatccaaa attacaaaat cgcttctatt      60
gtagttcctc ctccaat                                                    77

<210> SEQ ID NO 32
<211> LENGTH: 71
<212> TYPE: DNA
<213> ORGANISM: Phrixothrix Red Luciferase

<400> SEQUENCE: 32
agggcgaatt cttcttaaaa accatacaaa actacaaaat cgcttctatt gtagttcctc      60
ctccaattat g                                                          71
```

<210> SEQ ID NO 33
<211> LENGTH: 77
<212> TYPE: DNA
<213> ORGANISM: Phrixothrix Red Luciferase

<400> SEQUENCE: 33
gttcctcctc caattatggt atatttggct aaaagtcctc tagtcgatga atacaattta    60
tcgagcttaa cggaaat                                                   77

<210> SEQ ID NO 34
<211> LENGTH: 73
<212> TYPE: DNA
<213> ORGANISM: Phrixothrix Red Luciferase

<400> SEQUENCE: 34
tttggctaaa agtccattag tcgatgaata caatctgtcg agcttaacgg aaattgcttg    60
tggagggtct cct                                                       73

<210> SEQ ID NO 35
<211> LENGTH: 73
<212> TYPE: DNA
<213> ORGANISM: Phrixothrix Red Luciferase

<400> SEQUENCE: 35
ggaaattgct tgtggagggt ctcctttagg aagagacatc gcagataaag tagcaaagag    60
attgaaagta cat                                                       73

<210> SEQ ID NO 36
<211> LENGTH: 77
<212> TYPE: DNA
<213> ORGANISM: Phrixothrix Red Luciferase

<400> SEQUENCE: 36
gggtctcctt taggaagaga tatcgcagat aaagtagcca agagattgaa agtacatgga    60
atcctacaag gatatgg                                                   77

<210> SEQ ID NO 37
<211> LENGTH: 73
<212> TYPE: DNA
<213> ORGANISM: Phrixothrix Red Luciferase

<400> SEQUENCE: 37
ggatatggat taaccgaaac ctgcagcgct ctaatactga gccccaatga tcgagaactt    60
aaaaaaggtg caa                                                       73

<210> SEQ ID NO 38
<211> LENGTH: 77
<212> TYPE: DNA
<213> ORGANISM: Phrixothrix Red Luciferase

<400> SEQUENCE: 38
ccgaaacctg cagcgctcta atacttagcc ccaacgatag agaacttaaa aaaggtgcaa    60
ttggaacgcc tatgcca                                                   77

<210> SEQ ID NO 39
<211> LENGTH: 81
<212> TYPE: DNA
<213> ORGANISM: Phrixothrix Red Luciferase

<400> SEQUENCE: 39
ctaatactta gccccaatga tcgagaactt aaaaagggtg caattggaac gcctatgcca    60
tatgttcaag ttaaagttat a    81

<210> SEQ ID NO 40
<211> LENGTH: 73
<212> TYPE: DNA
<213> ORGANISM: Phrixothrix Red Luciferase

<400> SEQUENCE: 40
tgggaaggcg ctaggaccaa gagaaaaagg cgagatttgc ttcaaaagtc aaatgcttat    60
gaaaggatat cac    73

<210> SEQ ID NO 41
<211> LENGTH: 77
<212> TYPE: DNA
<213> ORGANISM: Phrixothrix Red Luciferase

<400> SEQUENCE: 41
aaaaggcgaa atatgcttca aaagtcaaat gcttatgaag ggctatcaca acaatccgca    60
agcaactcgt gatgctc    77

<210> SEQ ID NO 42
<211> LENGTH: 75
<212> TYPE: DNA
<213> ORGANISM: Phrixothrix Red Luciferase

<400> SEQUENCE: 42
tccgcaagca actcgtgatg ctcttgacaa agatgggtgg cttcatactg gggatcttgg    60
atattacgac gaaga    75

<210> SEQ ID NO 43
<211> LENGTH: 73
<212> TYPE: DNA
<213> ORGANISM: Phrixothrix Red Luciferase

<400> SEQUENCE: 43
gacagattta tctatgtagt tgatcgattg aaagagctta ttaaatataa aggatatcag    60
gttgcgcctg ctg    73

<210> SEQ ID NO 44
<211> LENGTH: 77
<212> TYPE: DNA
<213> ORGANISM: Phrixothrix Red Luciferase

<400> SEQUENCE: 44
atttatctat gtagttgatc gattgaaaga actcatcaaa tataaggat atcaggttgc    60 gcctgctgaa ctggaaa    77

<210> SEQ ID NO 45
<211> LENGTH: 75
<212> TYPE: DNA
<213> ORGANISM: Phrixothrix Red Luciferase

<400> SEQUENCE: 45
cgcctgctga actggaaaat ctgcttttac aacacccaaa tatttctgat gcgggtgtta    60
ttggaattcc ggacg    75

<210> SEQ ID NO 46
<211> LENGTH: 77
<212> TYPE: DNA
<213> ORGANISM: Phrixothrix Red Luciferase

<400> SEQUENCE: 46
ctgaactgga aaatctgctt ttacaacatc ctaatatttc tgatgcgggt gttattggaa    60
ttccggacga atttgct                                                  77

<210> SEQ ID NO 47
<211> LENGTH: 75
<212> TYPE: DNA
<213> ORGANISM: Phrixothrix Red Luciferase

<400> SEQUENCE: 47
ttacaacatc caaatatttc tgatgcgggt gtcattggaa ttccggacga atttgctggt    60
caattacctt ccgcg                                                    75

<210> SEQ ID NO 48
<211> LENGTH: 77
<212> TYPE: DNA
<213> ORGANISM: Phrixothrix Red Luciferase

<400> SEQUENCE: 48
tgcgggtgtt attggaattc cggacgaatt tgctggtcag ttaccttccg cgtgtgttgt    60
gttagagcct ggtaaga                                                  77

<210> SEQ ID NO 49
<211> LENGTH: 73
<212> TYPE: DNA
<213> ORGANISM: Phrixothrix Red Luciferase

<400> SEQUENCE: 49
aactaaacat cttcgaggcg gtgtcgtatt tatcgacagt attccaaaag gcccaacagg    60
aaaactcatg aga                                                      73

<210> SEQ ID NO 50
<211> LENGTH: 48
<212> TYPE: DNA
<213> ORGANISM: Phrixothrix Red Luciferase

<400> SEQUENCE: 50
gaactccgtg caatatttgc ccgggaacag gcaaaatcaa aactataa                48

<210> SEQ ID NO 51
<211> LENGTH: 77
<212> TYPE: DNA
<213> ORGANISM: Rhagophthalmus ohbai Green Luciferase

<400> SEQUENCE: 51
cccagggacc ccctggacct gggcaccgcc ggcattcagc tctacagagc cctgaccaac    60
ttctccttcc tgaggga                                                  77

<210> SEQ ID NO 52
<211> LENGTH: 77
<212> TYPE: DNA
<213> ORGANISM: Rhagophthalmus ohbai Green Luciferase

```
<400> SEQUENCE: 52
cctgggcacc gccggcatcc agctgtacag ggccctgacc aacttctcct tcctgaggga    60
ggccctgatc gacgccc                                                   77

<210> SEQ ID NO 53
<211> LENGTH: 79
<212> TYPE: DNA
<213> ORGANISM: Rhagophthalmus ohbai Green Luciferase

<400> SEQUENCE: 53
gtggtgtctt acgccgacat cctggagaac agctgtagac tggctaagtg ctacgagaac    60
tacggcctgc gccagaaca                                                 79

<210> SEQ ID NO 54
<211> LENGTH: 79
<212> TYPE: DNA
<213> ORGANISM: Rhagophthalmus ohbai Green Luciferase

<400> SEQUENCE: 54
gcgccagaac agcgtgatct ccgtgtgcag cgagaatagc accatcttct tctacccgt     60 gatcgccgcc ctgtacatg                                                 79

<210> SEQ ID NO 55
<211> LENGTH: 81
<212> TYPE: DNA
<213> ORGANISM: Rhagophthalmus ohbai Green Luciferase

<400> SEQUENCE: 55
tcaagaaggt ggtgctgctg acagcaagg aggatatggg cgaggcccag tgcctgagca     60
acttcatggc ccggtactcc g                                              81

<210> SEQ ID NO 56
<211> LENGTH: 81
<212> TYPE: DNA
<213> ORGANISM: Rhagophthalmus ohbai Green Luciferase

<400> SEQUENCE: 56
tcaagccaag ggacttcgac gccaaggagc aggtggccct tattatgtcc tcctctggca    60
ccaccggcct gccaaagggc g                                              81

<210> SEQ ID NO 57
<211> LENGTH: 75
<212> TYPE: DNA
<213> ORGANISM: Rhagophthalmus ohbai Green Luciferase

<400> SEQUENCE: 57
atcgagaagt acagaatccc aacaatcgtg ctggcccctc ctgtgatggt gttcctggcc    60
aagagccccc tggtg                                                     75

<210> SEQ ID NO 58
<211> LENGTH: 79
<212> TYPE: DNA
<213> ORGANISM: Rhagophthalmus ohbai Green Luciferase

<400> SEQUENCE: 58
atcccaacaa tcgtgctggc ccccccgtg atggtgttcc tggctaagag ccccctggtg     60
gaccagtacg acctgtcca                                                 79
```

<210> SEQ ID NO 59
<211> LENGTH: 75
<212> TYPE: DNA
<213> ORGANISM: Rhagophthalmus ohbai Green Luciferase

<400> SEQUENCE: 59
gagaggtggc caccggcggc gccCctgtgg gcaccgaggt tgccgtggcc gtggccaagc    60
ggctgaagat cggcg    75

<210> SEQ ID NO 60
<211> LENGTH: 75
<212> TYPE: DNA
<213> ORGANISM: Rhagophthalmus ohbai Green Luciferase

<400> SEQUENCE: 60
gccatcgaca aggagggctg gctgcactcc ggcgacgtgg gatactacga cgacgatggc    60
cacttcttcg tggtg    75

<210> SEQ ID NO 61
<211> LENGTH: 73
<212> TYPE: DNA
<213> ORGANISM: Rhagophthalmus ohbai Green Luciferase

<400> SEQUENCE: 61
ctccggcgac gtgggctact acgacgacga tggacatttc ttcgtggtgg accggctgaa    60
ggagctgatc aag    73

<210> SEQ ID NO 62
<211> LENGTH: 81
<212> TYPE: DNA
<213> ORGANISM: Rhagophthalmus ohbai Green Luciferase

<400> SEQUENCE: 62
cgacgatggc cacttcttcg tggtggaccg gctgaaagag ctgatcaagt acaagggcta    60
ccaggtggcc ccgccgagc t    81

<210> SEQ ID NO 63
<211> LENGTH: 71
<212> TYPE: DNA
<213> ORGANISM: Rhagophthalmus ohbai Green Luciferase

<400> SEQUENCE: 63
agtggctgct gctccagcac ccatccatca aggatgccgg cgtgaccggc gtgcccgacg    60
aggccgccgg c    71

<210> SEQ ID NO 64
<211> LENGTH: 75
<212> TYPE: DNA
<213> ORGANISM: Rhagophthalmus ohbai Green Luciferase

<400> SEQUENCE: 64
ccgagcagga gatcatcgac tacatcgccg agcgagtgtc tcccaccaag cgcatccggg    60
gcggcgtcgt cttcg    75

<210> SEQ ID NO 65
<211> LENGTH: 71
<212> TYPE: DNA
<213> ORGANISM: Rhagophthalmus ohbai Green Luciferase

```
-continued

<400> SEQUENCE: 65
gagcgggtgt cccccaccaa gcgcatccgg ggcggagtcg tcttcgtgga cgacatcccc      60
aagggcgcca c                                                          71
```